(12) United States Patent
Hatterer et al.

(10) Patent No.: US 12,122,850 B2
(45) Date of Patent: Oct. 22, 2024

(54) BISPECIFIC GPC3XCD28 AND GPC3XCD3 ANTIBODIES AND THEIR COMBINATION FOR TARGETED KILLING OF GPC3 POSITIVE MALIGNANT CELLS

(71) Applicant: LamKap Bio gamma AG, Pfaeffikon (CH)

(72) Inventors: Eric Hatterer, Valleiry (FR); Anja Seckinger, Lachen (CH); Dirk Hose, Pfaeffikon (CH)

(73) Assignee: LamKap Bio gamma AG, Pfaeffikon Sz (CH)

( * ) Notice: Subject to any disclaimer, the term of this patent is extended or adjusted under 35 U.S.C. 154(b) by 0 days.

(21) Appl. No.: 18/183,840

(22) Filed: Mar. 14, 2023

(65) Prior Publication Data

US 2023/0287146 A1 Sep. 14, 2023

Related U.S. Application Data

(60) Provisional application No. 63/328,586, filed on Apr. 7, 2022, provisional application No. 63/319,709, filed on Mar. 14, 2022.

(51) Int. Cl.
C07K 16/46 (2006.01)
A61P 35/00 (2006.01)

(52) U.S. Cl.
CPC ............ *C07K 16/468* (2013.01); *A61P 35/00* (2018.01); *C07K 2317/31* (2013.01); *C07K 2317/565* (2013.01); *C07K 2317/71* (2013.01)

(58) Field of Classification Search
CPC .............. C07K 16/468; C07K 2317/31; C07K 2317/565; C07K 2317/71; A61P 35/00
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 5,013,556 A | 5/1991 | Woodle et al. |
| 5,030,719 A | 7/1991 | Umemoto et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,693,761 A | 12/1997 | Queen et al. |
| 5,693,792 A | 12/1997 | Torii et al. |
| 5,714,350 A | 2/1998 | Co et al. |
| 5,777,085 A | 7/1998 | Co et al. |
| 5,834,597 A | 11/1998 | Tso et al. |
| 5,843,597 A | 12/1998 | Getz |
| 5,859,205 A | 1/1999 | Adair et al. |
| 5,885,573 A | 3/1999 | Bluestone et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,025,477 A | 2/2000 | Calenoff |
| 6,075,181 A | 6/2000 | Kucherlapati et al. |
| 6,113,901 A | 9/2000 | Bluestone |
| 6,143,297 A | 11/2000 | Bluestone |
| 6,150,584 A | 11/2000 | Kucherlapati et al. |
| 6,172,197 B1 | 1/2001 | McCafferty et al. |
| 6,406,696 B1 | 6/2002 | Bluestone |
| 6,491,913 B2 | 12/2002 | Hopwood et al. |
| 6,491,916 B1 | 12/2002 | Bluestone et al. |

(Continued)

FOREIGN PATENT DOCUMENTS

| | | |
|---|---|---|
| CN | 1298020 A | 6/2001 |
| CN | 1421459 A | 6/2003 |

(Continued)

OTHER PUBLICATIONS

U.S. Appl. No. 18/180,116 (Unpublished). CD28 Bispecific Antibodies for Targeted T Cell Activation. (Year: 2023).*
U.S. Appl. No. 18/491,130 (Unpublished). PD-L1XCD28 Bispecific Antibodies for Immune Checkpoint-Dependent T Cell Activation. (Year: 2023).*
Adair et al., "Humanization of the Murine Anti-human CD3 Monoclonal Antibody OKT3," Hum. Antibod. Hybridomas, 5(1-2):41-47, 1994.
Alegre et al., "An Anti-Murine CD3 Monoclonal Antibody with a Low Affinity for Fey Receptors Suppresses Transplantation Responses While Minimizing Acute Toxicity and Immunogenicity," The Journal of Immunology, 155:1544-1555 (1995).

(Continued)

*Primary Examiner* — Brad Duffy
*Assistant Examiner* — Elizabeth A Shupe
(74) *Attorney, Agent, or Firm* — COOLEY LLP; Cynthia A. Kozakiewicz; Taylor D. Canady

(57) ABSTRACT

The present invention relates to GPC3×CD3 bispecific antibodies, GPC3×CD28 bispecific antibodies and the combination of two, agonistic and fully human KA-bodies with one targeting GPC3×CD3 and the other targeting GPC3× CD28, and both not competing for the binding to GPC3. The present invention also relates to the use of the bispecific antibodies for the treatment of GPC3 positive malignancies.

34 Claims, 13 Drawing Sheets

Specification includes a Sequence Listing.

(56) References Cited

U.S. PATENT DOCUMENTS

| | | |
|---|---|---|
| 6,521,404 B1 | 2/2003 | Griffiths et al. |
| 6,528,624 B1 | 3/2003 | Idusogie et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,750,325 B1 | 6/2004 | Jolliffe et al. |
| 7,041,289 B1 | 5/2006 | Bach et al. |
| 7,728,114 B2 | 6/2010 | Mach et al. |
| 8,551,478 B2 | 10/2013 | Mach et al. |
| 9,850,304 B2 | 12/2017 | Mach et al. |
| 10,759,858 B2 | 9/2020 | Mach et al. |
| 11,203,646 B2 * | 12/2021 | Fischer ............... C07K 16/464 |
| 2003/0108548 A1 | 6/2003 | Bluestone et al. |
| 2003/0124119 A1 | 7/2003 | Yamazaki et al. |
| 2003/0138417 A1 | 7/2003 | Kaisheva et al. |
| 2003/0216551 A1 | 11/2003 | Delovitch |
| 2003/0235583 A1 | 12/2003 | Sturis et al. |
| 2004/0037826 A1 | 2/2004 | Michelsen et al. |
| 2006/0002933 A1 | 1/2006 | Bluestone et al. |
| 2006/0165691 A1 | 7/2006 | Bolt et al. |
| 2006/0165692 A1 | 7/2006 | Bolt et al. |
| 2006/0165693 A1 | 7/2006 | Bolt et al. |
| 2006/0177896 A1 | 8/2006 | Mach et al. |
| 2006/0275292 A1 | 12/2006 | Delovitch |
| 2006/0275305 A1 | 12/2006 | Bryant |
| 2006/0292142 A1 | 12/2006 | Bluestone et al. |
| 2007/0065437 A1 | 3/2007 | Elson et al. |
| 2007/0077246 A1 | 4/2007 | Koenig et al. |
| 2007/0178092 A1 | 8/2007 | Bolt et al. |
| 2007/0190045 A1 | 8/2007 | Herold et al. |
| 2007/0190052 A1 | 8/2007 | Herold et al. |
| 2007/0224191 A1 | 9/2007 | Walters et al. |
| 2008/0095766 A1 | 4/2008 | Koenig et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2010/0183554 A1 | 7/2010 | Mach et al. |
| 2010/0209437 A1 | 8/2010 | Elson et al. |
| 2011/0123532 A1 | 5/2011 | Gurney et al. |
| 2012/0149876 A1 | 6/2012 | Von Kreudenstein et al. |
| 2012/0184716 A1 | 7/2012 | Fischer et al. |
| 2013/0195849 A1 | 8/2013 | Spreter Von Kreudenstein et al. |
| 2014/0193399 A1 | 7/2014 | Mach et al. |
| 2014/0242079 A1 | 8/2014 | Bacac et al. |
| 2017/0129962 A1 | 5/2017 | Regula et al. |
| 2018/0194842 A1 | 7/2018 | Mach et al. |
| 2021/0009691 A1 | 1/2021 | Mach et al. |
| 2022/0135684 A1 | 5/2022 | Desjarlais et al. |
| 2022/0195067 A1 * | 6/2022 | Buatois ............. C07K 16/3007 |
| 2023/0295348 A1 | 9/2023 | Fischer et al. |
| 2024/0002544 A1 | 1/2024 | Majocchi et al. |

FOREIGN PATENT DOCUMENTS

| | | |
|---|---|---|
| EP | 1475100 A1 | 11/2004 |
| GB | 2380127 A | 4/2003 |
| JP | H05320072 A | 12/1993 |
| JP | 2004292455 A | 10/2004 |
| RU | 2179862 C1 | 2/2002 |
| WO | WO-9100360 A1 | 1/1991 |
| WO | WO-9201047 A1 | 1/1992 |
| WO | WO-9220373 A1 | 11/1992 |
| WO | WO-9308829 A1 | 5/1993 |
| WO | WO-9402602 A1 | 2/1994 |
| WO | WO-9411026 A2 | 5/1994 |
| WO | WO-9428027 A1 | 12/1994 |
| WO | WO-9522618 A1 | 8/1995 |
| WO | WO-9627011 A1 | 9/1996 |
| WO | WO-9633735 A1 | 10/1996 |
| WO | WO-9634096 A1 | 10/1996 |
| WO | WO-9744362 A1 | 11/1997 |
| WO | WO-9856418 A1 | 12/1998 |
| WO | WO-9953049 A1 | 10/1999 |
| WO | WO-03026692 A2 | 4/2003 |
| WO | WO-2004052397 A1 | 6/2004 |
| WO | WO-2004071439 A2 | 8/2004 |
| WO | WO-2004075913 A1 | 9/2004 |
| WO | WO-2004106380 A2 | 12/2004 |
| WO | WO-2005048935 A2 | 6/2005 |
| WO | WO-2005099755 A2 | 10/2005 |
| WO | WO-2005118635 A2 | 12/2005 |
| WO | WO-2006028936 A2 | 3/2006 |
| WO | WO-2006050949 A2 | 5/2006 |
| WO | WO-2007033230 A2 | 3/2007 |
| WO | WO-2007117600 A2 | 10/2007 |
| WO | WO-2007145941 A2 | 12/2007 |
| WO | WO-2007147090 A2 | 12/2007 |
| WO | WO-2008079713 A2 | 7/2008 |
| WO | WO-2008119567 A2 | 10/2008 |
| WO | WO-2010135558 A1 | 11/2010 |
| WO | WO-2011084255 A2 | 7/2011 |
| WO | WO-2011131746 A2 | 10/2011 |
| WO | WO-2012023053 A2 | 2/2012 |
| WO | WO-2012117002 A1 | 9/2012 |
| WO | WO-2013088259 A2 | 6/2013 |
| WO | WO-2014087248 A2 | 6/2014 |
| WO | WO-2016036678 A1 | 3/2016 |
| WO | WO-2017159287 A1 | 9/2017 |
| WO | WO-2018209304 A1 | 11/2018 |
| WO | WO-2018215835 A1 | 11/2018 |
| WO | WO-2019016411 A1 | 1/2019 |
| WO | WO-2019234576 A1 | 12/2019 |
| WO | WO-2019246514 A1 | 12/2019 |
| WO | WO-2020127618 A1 | 6/2020 |
| WO | WO-2020127628 A1 | 6/2020 |
| WO | WO-2020132024 A1 | 6/2020 |
| WO | WO-2020132066 A1 | 6/2020 |
| WO | WO-2020198009 A1 | 10/2020 |
| WO | WO-2021053587 A1 | 3/2021 |
| WO | WO-2021110647 A1 | 6/2021 |
| WO | WO-2021155071 A1 | 8/2021 |
| WO | WO-2021259890 A1 | 12/2021 |
| WO | WO-2022025220 A1 | 2/2022 |
| WO | WO-2022040482 A1 | 2/2022 |
| WO | WO-2022130348 A1 | 6/2022 |
| WO | WO-2022200387 A1 | 9/2022 |
| WO | WO-2022200389 A1 | 9/2022 |
| WO | WO-2023170474 A1 | 9/2023 |
| WO | WO-2023174925 A1 | 9/2023 |
| WO | WO-2024084052 A1 | 4/2024 |

OTHER PUBLICATIONS

Al-Lazikani B., et al., "Standard Conformations for the Canonical Structures of Immunoglobulins," Journal of molecular biology, Nov. 1997, vol. 273 (4), pp. 927-948.

Amemiya et al., "Downregulation of TGF-β mRNA and Protein in the Muscles of Patients with Inflammatory Myopathies after Treatment with High-Dose Intravenous Immunoglobulin," Clinical Immunology, 94(2):99-104 (2000).

Baldrick, P., "Pharmaceutical excipient development: the need for preclinical guidance," Regulatory Toxicology and Pharmacology, Oct. 2000, 32(2), pp. 210-218.

Belghith et al., "TGF-beta-dependent Mechanisms Mediate Restoration of Self-tolerance Induced by Antibodies to CD3 in overt Autoimmune Diabetes," Nat Med. Sep. 2003;9(9), pp. 1202-1208.

Bilinska, Z.T., et al.; "Active lymphocyte myocarditis treated with murine OKT3 monoclonal antibody in a patient presenting with intractable ventricular Tachycardia," Texas Heart Inst. J.; 29(2):113-117 (2002).

Bobo et al. "Convection-enhanced delivery of macromolecules in the brain," Proceedings of the National Academy of Sciences, Mar. 1994, 91(6), pp. 2076-2080.

Bose et al., "Problems in using statistical analysis of replacement and silent mutations in antibody genes for determining antigen-driven affinity selection," Immunology, 116: 172-183 (2005).

Bowie et al. "A method to identify protein sequences that fold into a known three-dimensional structure," Science, (1991); 253(5016):164-170.

(56) References Cited

OTHER PUBLICATIONS

Bradbury et al., "Antibodies from phage antibody libraries," Journal of Immunological Methods (2004) 290(1-2):29-49.
Brodeur et al., "Mouse-Human Myeloma Partners for the Production of Heterohybridomas," Monoclonal Antibody Production Techniques and Applications, Marcel Dekker, Inc., Mar. 1987, pp. 51-63.
Buckner C. et al., "Priming B Cell-mediated Anti-HIV Envelope Responses by Vaccination Allows for the Long-term Control of Infection in Macaques Exposed to a R5-tropic SHIV," Virology (Mar. 2004), 320(1):167-180.
Caron et al., "Engineered Humanized Dimeric Forms of IgG Are More Effective Antibodies," the Journal of Experimental Medicine, Oct. 1992, 176(4):1191-1195.
Carpenter, P.A., et al.; "A humanized non-FcR-binding anti-CD3 antibody, visilizumab, for treatment of steroid-refractory acute graft-versus-host disease," American Society of Hematology, United States, Blood; 99(8):2712-2719 (2002).
Castillo et al., "Glypican-3 induces a mesenchymal to epithelial transition in human breast cancer cells," Oncotarget., (Sep. 2016); 7(37):60133-60154.
Chappell, S. et al., "A 9-nt segment of a cellular mRNA can function as an internal ribosome entry site (IRES) and when present in linked multiple copies greatly enhances IRES activity," Proceedings of the National Academy of Sciences, Feb. 2000, 97(4), pp. 1536-1541.
Charman, W.N., "Lipids, lipophilic drugs, and oral delivery-some emerging concepts," Journal of Pharmaceutical Sciences, Aug. 2000, 89(8), pp. 967-978.
Charpentier, B., et al.; "Acute clinical syndrome associated with OKT3 administration. Prevention by single injection of an anti-human TNF monoclonal antibody," Presse Medicale (Paris, France: 1983), Nov. 1, 1991, 20(40):2009-2011 (Abstract Only), 2 pages.
Chatenoud, L., "CD3 antibody treatment stimulates the functional capability of regulatory T cells," Novartis Foundation Symposium, 252:279-86 (2003).
Chatenoud, L., "CD3-Specific Antibody-Induced Active Tolerance: from Bench to Bedside," Nature Reviews | Immunology, 3(2): 123-132 (2003).
Chatenoud, L., et al., "CD3 antibody-induced dominant self tolerance in overtly diabetic NOD mice," The Journal of Immunology, 158:2947-2954 (1997).
Chen, X., et al., "Combination Therapy of Hepatocellular Carcinoma by GPC3-Targeted Bispecific Antibody and Irinotecan is Potent in Suppressing Tumor Growth in Mice," Mol Cancer Ther., (2022); 21(1):149-158.
Chotia et al., "Canonical Structures for the Hypervariable Regions of Immunoglobulins," J. Mol. Biol. (Aug. 20, 1987); 196(4):901-917.
Chotia et al., "Conformations of Immunoglobulin Hypervariable Regions," Nature (Dec. 1989); 342(6252):878-883.
Clackson T., et al., "Making Antibody Fragments Using Phage Display Libraries," Nature, Aug. 15, 1999, vol. 352, No. 6336, pp. 624-628.
ClinicalTrials.gov Identifiers: NCT03972657: Study of REGN5678 (Anti-PSMAxCD28) With or Without Cemiplimab (Anti-PD-1) in Patients With Metastatic Castration-resistant Prostate Cancer and Other Tumors; Jun. 3, 2019; [retrieved online Jan. 16, 2024] URL: https://classic.clinicaltrials.gov/ct2/show/NCT03972657?term=NCT03972657&draw=2&rank=1, 11 pages.
ClinicalTrials.gov Identifiers: NCT04590326: Study of REGN5668 Administered in Combination With Cemiplimab or REGN4018 in Adult Women With Recurrent Ovarian Cancer; Oct. 19, 2020; [retrieved online Jan. 16, 2024] URL: https://classic.clinicaltrials.gov/ct2/show/NCT04590326?term=NCT04590326&draw=2&rank=1, 10 pages.
ClinicalTrials.gov Identifiers: NCT04626635: A Trial to Find Out How Safe REGN7075 is and How Well it Works in Combination With Cemiplimab for Adult Participants With Advanced Cancers (COMBINE-EGFR-1), Nov. 12, 2020; [retrieved online Jan. 16, 2024] URL: https://classic.clinicaltrials.gov/ct2/show/NCT04626635?term=NCT04626635&draw=2&rank =1, 18 pages.
ClinicalTrials.gov Identifiers: NCT05219513: A Study to Evaluate the Safety, Tolerability, Pharmacokinetics, and Efficacy of RO7443904 in Combination With Glofitamab in Participants With Relapsed/Refractory B-Cell Non-Hodgkin's Lymphoma; Feb. 2, 2022; [retrieved online Jan. 16, 2024] URL: https://classic.clinicaltrials.gov/ct2/show/NCT05219513?term=NCT05219513&draw=2&rank =1, 9 pages.
ClinicalTrials.gov Identifiers: NCT05585034; Phase 1, First-in-human, Dose-finding and Expansion Study to Evaluate XmAb® 808 in Combination With Pembrolizumab in Advanced Solid Tumors; Oct. 18, 2022; [retrieved online Jan. 16, 2024] URL: https://classic.clinicaltrials.gov/ct2/show/NCT05585034?term=NCT05585034&draw=2&rank=1, 8 pages.
Cole, S. et al. "The EBV-Hybridoma Technique and Its Application to Human Lung Cancer," Monoclonal Antibodies and Cancer Therapy 27, Jan. 1985, pp. 77-96.
Correnti, C.E., et al., "Simultaneous multiple interaction T-cell engaging (SMITE) bispecific antibodies overcome bispecific T-cell engager (BiTE) resistance via CD28 co-stimulation," Leukemia, (2018); 32(5):1239-1243.
Cote, R. et al., "Generation of human monoclonal antibodies reactive with cellular antigens," Proceedings of the National Academy of Sciences, Apr. 1983, vol. 80, pp. 2026-2030.
Davidson, B.L et al., "A model system for in vivo gene transfer into the central nervous system using an adenoviral vector," Nature Genetics, Mar. 1993, vol. 3, pp. 219-223.
Davies et al. "Antibody-antigen complexes," Annual review of biochemistry, (1990); 59(1):439-473.
De Wildt, R.M., et al.; "Antibody arrays for high-throughput screening of antibody-antigen interactions," Nat Biotechnol. (2000); 18(9):989-994.
Eppstein et al., "Biological activity of liposome-encapsulated murine interferon γ is mediated by a cell membrane receptor," Proceedings of the National Academy of Sciences, Jun. 1985, 82(11), pp. 3688-3692.
Ferran, C., et al.; "Cascade modulation by anti-tumor necrosis factor monoclonal antibody of interferon-gamma, interleukin 3 and interleukin 6 release after triggering of the CD3/T cell receptor activation pathway," European Journal of Immunology (1991); 21(10):2349-2353.
Ferran, C. et al.; "Reduction of morbidity and cytokine release in anti-CD3 MoAb-treated mice by corticosteroids," Transplantation, (1990); 50(4):642-648.
Fischer, N. et al., "Exploiting light chains for the scalable generation and platform purification of native human bispecific IgG," Nature Communications 6, Article No. 6113, Feb. 12, 2015, 6(1), https://doi: 10.1038/ncomms7113, 12 pages.
Fishwild et al., "High-avidity human IgGk monoclonal antibodies from a novel strain of minilocus transgenic mice," Nature Biotechnology, Jul. 1996, 14(7), pp. 845-851.
Frank et al., "SPOT Synthesis Epitope Analysis with Arrays of Synthetic Peptides Prepared on Cellulose Membranes," Meth. Mol. Bioi., Chapter 15,66:149-169, 1996.
Geller, A.I. et al., "An HSV-1 Vector Expressing Tyrosine Hydroxylase Causes Production and Release of L-DOPA from Cultured Rat Striatal Cells," Journal of Neurochemistry, Feb. 1995, 64(2), pp. 487-496.
Geller, A.I. et al., "Infection of cultured central nervous system neurons with a defective herpes simplex virus 1 vector results in stable expression of *Escherichia coli* β-galactosidase," Proceedings of the National Academy of Sciences, Feb. 1990, 87(3), pp. 1149-1153.
Geller, A.I. et al., "Long-term increases in neurotransmitter release from neuronal cells expressing a constitutively active adenylate cyclase from a herpes simplex virus type 1 vector," Proceedings of the National Academy of Sciences, Aug. 1993, 90(16), pp. 7603-7607.
GenBank Accession Nos. NP000724, published Dec. 23, 2003, "CD3E antigen, epsilon polypeptide (TiT3 complex)," pp. 1-3.
Geysen, H.M., et al., "Strategies for epitope analysis using peptide synthesis," J Immunol Methods., 102(2):259-274 (1987).
Goding, J.W. (Ed.) "Production of Monoclonal Antibodies," in Monoclonal Antibodies: Principles and Practice, 2nd Edition, Academic Press, pp. 59-103 (1986).

(56) References Cited

OTHER PUBLICATIONS

Gonzalez et al., "SDR grafting of a murine antibody using multiple human germline templates to minimize its immunogenicity," 41(9):863-72 (2004).
Green et al., "Antigen-specific human monoclonal antibodies from mice engineered with human Ig heavy and light chain YACs," Nature Genetics (1994) 7:13-21.
Gruber et al., "Efficient Tumor Cell Lysis Mediated by a Bispecific Single Chain Antibody Expressed in *Escherichia coli*," The Journal of Immunology, Jun. 1994, 152(11), pp. 5368-5374.
Harlow, E., et al., "Antibodies, A Laboratory Manual, Chapter 4: Antibody Response," Cold Spring Harbor laboratory, pp. 37-47 (1988).
Hayward, et al. "Lysis of CD3 hybridoma targets by cloned human CD4 lymphocytes," Immunology. May 1988;64(1):87-92.
He. M.M., et al.; "Small-molecule inhibition of TNF-alpha," Science (2005); 310(5750):1022-1025.
Hellen, C.U. and Sarnow, P., "Internal ribosome entry sites in eukaryotic mRNA molecules," Genes & Development, Jul. 2001, 15(13), pp. 1593-1612.
Herold et al., "Anti-CD3 monoclonal antibody in new-onset type 1 diabetes mellitus," N Engl J Med. May 30, 2002; 346(22):1692-8.
Herold, K,C. et al., "Activation of human T cells by FcR nonbinding anti-CD3 mAb, hOKT31(Ala-Ala)," American Society for Clinical Investigation, United States, J. Clin. Invest.; 111(3):409-418 (2003).
Holliger, P., et al.; "Carcinoembryonic antigen (CEA)-specific T-cell activation in colon carcinoma induced by anti-CD3 x anti-CEA bispecific diabodies and B7 x anti-CEA bispecific fusion proteins," Cancer Res. (1999); 59(12):2909-2916.
Holliger, P. et al., "'Diabodies': Small bivalent and bispecific antibody fragments," Proceedings of the National Academy of Sciences USA (Jul. 1993); 90(14):6444-6448.
Honegger et al. "Yet another numbering scheme for immunoglobulin variable domains: an automatic modeling and analysis tool," Journal of Molecular Biology, (2001); 309(3):657-670.
Hoogenboom, H.R. and Winter, G., "By-passing Immunisation. Human Antibodies from Synthetic Repertoires of Germline VH Gene Segments Rearranged in Vitro," Journal of Molecular Biology, Sep. 1992, 227(2), pp. 381-388.
Husain, B., et al., "Expanding the boundaries of biotherapeutics with bispecific antibodies," Biodrugs, vol. 12, No. 5, Aug. 21, 2018, pp. 441-464.
Hwang et al., "Hepatic uptake and degradation of unilamellar sphingomyelin/cholesterol liposomes: A kinetic study," Proceedings of the National Academy of Sciences, Jul. 1980, 77(7), pp. 4030-4034.
Ishiguro, T., et al.; "An anti-glypican 3/CD3 bispecific T cell-redirecting antibody for treatment of solid tumors," Sci Transl Med.; (2017); 9(410):eaal4291, 13 pages.
Isobe, M.; "Scintigraphic imaging of MHC class II antigen induction in mouse kidney allografts: a new approach to noninvasive detection of early rejection," Transplant International: Official Journal of the European Society for Organ Transplantation (1993); 6(5):263-269.
Jansen et al., "Immunotoxins: Hybrid Molecules Combining High Specificity and Potent Cytotoxicity," Immunological Reviews, Feb. 1982, 62(1), pp. 185-216.
Jones et al., "Replacing the complementary-determining regions in a human antibody with those from a mouse," Nature, vol. 321, May 1986, pp. 522-525.
Kabat, E. A. et al., "Unusual distributions of amino acids in complementarity-determining (hypervariable) segments of heavy and light chains of immunoglobulins and their possible roles in specificity of antibody-combining sites," J. Biol. Chem., Oct. 10, 1977;252(19):6609-6616.
Kabat, E. A., "The structural basis of antibody complementarity," Adv. Prot. Chem., 32:1-75 (1978).
Kabat, E.A. et al., "Sequences of Proteins of Immunological Interest," 5th Edition, vol. 1, NIH Publication 91-3242, 1991; p. 310 and p. 662, 4 pages.
Kaplitt, M. G. et al., "Long-term gene expression and phenotypic correction using adeno-associated virus vectors in the mammalian brain," Nature Genetics, Oct. 1994, 8(2), pp. 148-154.
Keymeulen, B., et al.; "Insulin needs after CD3-antibody therapy in new-onset type 1 diabetes," N Engl J Med. (2005) 352(25):2598-2608.
Killen, J.A., et al.; "Specific killing of lymphocytes that cause experimental autoimmune myasthenia gravis by ricin toxin-acetylcholine receptor conjugates," Journal of Immunology, 1984, vol. 133, No. 5, p. 1335-2549.
KIM., et al., "When does Rheumatoid Arthritis Begin and Why do we need to Know?" Arthritis & Rheumatism vol. 43, No. 3, Mar. 2000, pp. 473-484.
Kohler et al., "Continuous cultures of fused cells secreting antibody of predefined specificity," Nature., (Aug. 1975); 256(5517):495-497.
Kostelny. S. A. et al., "Formation of a Bispecific Antibody by the Use of Leucine Zippers," The Journal of Immunology, 148(5):1547-1553 (1992).
Kozbor et al., "A human hybrid myeloma for production of human monoclonal antibodies," The Journal of Immunology, Dec. 1984, 133(6), pp. 3001-3005.
Kozbor et al., "The production of monoclonal antibodies from human lymphocytes," Immunology Today, Mar. 1983, 4(3), pp. 72-79.
Kraan M.C., et al., "Asymptomatic Synovitis Precedes Clinically Manifest Arthritis," Arthritis Rheum. Aug. 1998;41 (8):1481-1488.
Kramer et al., "Synthesis and Screening of Peptide Libraries on Continuous Cellulose Membrane Supports," Meth. Mol. Bio., Chapter 4, 87:25-39, 1998.
Kung, P., et al.; "Monoclonal antibodies defining distinctive human T cell surface antigens," Science, 206(4416):347-349 (1979).
Kung, P.C., et al.; "Creating a useful panel of anti-T cell monoclonal antibodies," Int. J. Immunopharmacol, 3(3):175-181 (1981).
Kung, P.C., et al.; "Strategies for generating monoclonal antibodies defining human t-lymphocyte differentiation antigens," Transplant. Proc., XII(3 -Suppl. 1):141-146 (1980).
La Salle et al., "An Adenovirus Vector for Gene Transfer into Neurons and Glia in the Brain," Science, Feb. 1993, 259(5097), pp. 988-990.
Ledbetter, et al. "Valency of CD3 binding and internalization of the CD3 cell-surface complex control T cell responses to second signals: distinction between effects on protein kinase C, cytoplasmic free calcium, and proliferation." J Immunol. Jun. 1, 1986;136(11):3945-52.
Lefranc et al. "IMGT, the international ImMunoGeneTics database," Nucleic Acids Research, (1999); 27(1):209-212.
Lefranc MP. "Immunoglobulins: 25 years of immunoinformatics and IMGT-ONTOLOGY," Biomolecules, (2014); 4(4):1102-1139.
Li et al., "Glypicans as Cancer Therapeutic Targets," Trends Cancer., (Nov. 2018); 4(11):741-754.
Li et al., "Prognostic and clinicopathological significance of glypican-3 overexpression in hepatocellular carcinoma: A meta-analysis," World J Gastroenterol., (May 2014); 20(20):6336-6344.
Li et al., "The Role of Glypicans in Cancer Progression and Therapy," J Histochem Cytochem., (Dec. 2020); 68(12):841-862.
Lim, F., et al., in DNA Cloning: Mammalian Systems, D. Glover, Ed. (Oxford Univ. Press, Oxford England, (1995), 23 pages.
Liu, A.Y., et al.; "Production of a Mouse-Human Chimeric Monoclonal Antibody to CD20 With Potent Fc-Dependent Biological Activity," The Journal of Immunology, Nov. 1987, vol. 139, No. 10, pp. 3521-3526.
Liu et al., "Chimeric mouse-human IgG1 antibody that can mediate lysis of cancer cells," Proc. Natl. Acad. Sci. USA, 84:3439-3443 (1987).
Lonberg and Huszar, "Human Antibodies from Transgenic Mice," International Reviews of Immunology, Jan. 1995, 13(1), pp. 65-93.
Lonberg et al., "Antigen-specific human antibodies from mice comprising four distinct genetic modifications," Nature, Apr. 1994, 368(6474), pp. 856-859.
Ludviksson, B.R., et al.; "TGF-beta production regulates the development of the 2,4,6-trinitrophenol-conjugated keyhole limpet

(56) References Cited

OTHER PUBLICATIONS hemocyanin-induced colonic inflammation in IL-2-deficient mice," The Journal of Immunology, 159(7):3622-3628 (1997).
MacDonald, L.E., et al., "Kappa-on-Heavy (KoH) bodies are a distinct class of fully-human antibody-like therapeutic agents with antigen-binding properties," Proc Natl Acad Sci USA (2020); 117(1):292-299.
Magistrelli, G. et al. (2010) "Rapid, simple and high yield production of recombinant proteins in mammalian cells using a versatile episomal system," Protein Expr Purif, 72:209-216.
Maini et al., "Infliximab (chimeric anti-tumour necrosis factor aplha monoclonal antibody) versus placebo in rheumatoid arthritis patients receiving concomitant methotrexate: a randomised phase III trial," Lancet, 354(9194):1932-39 (1999).
Majocchi, S., et al., "Abstract 2884: Optimized CD28 bispecific antibodies for targeted activation of T cells within the tumor microenvironment," Cancer Res (Jun. 2022); 82(12_Supplement): 2884, Abstract, 3 pages; doi: 10.1158/1538-7445.AM2022-2884.
Malfait et al., "Chronic Relapsing Homologous Collagen-Induced Arthritis in DBA/1 Mice as a Model for Testing Disease-Modifying and Remission-Inducing Therapies," Arthritis & Rheumatism, 44(5):1215-1224 (2001).
Malmqvist M. "Biospecific interaction analysis using biosensor technology," Nature, (1993); 361(6408):186-187.
Marasco et al. "Design, intracellular expression, and activity of a human anti-human immunodeficiency virus type 1 gp120 single-chain antibody," Proceedings of the National Academy of Sciences, (1993); 90(16):7889-7893.
Marks et al., "By-passing Immunization: Building High Affinity Human Antibodies by Chain Shuffling," Bio/Technology, Jul. 1992, 10(7), pp. 779-783.
Marks et al., "By-passing Immunization. Human Antibodies from V-gene Libraries Displayed on Phage," Journal of Molecular Biology, Dec. 1991, 222(3), pp. 581-597.
Martin et al., "Irreversible Coupling of Immunoglobulin Fragments to Preformed Vesicles," The Journal of Biological Chemistry, Jan. 1992, 257(1), pp. 286-288.
Mendez, M.J., et al.; "Functional transplant of megabase human immunoglobulin loci recapitulates human antibody response in mice," Nat Genet. (1997); 15(2):146-156.
Menghini, V.V., et al.; "Combined immunosuppression for the treatment of idiopathic giant cell myocarditis," Mayo Clinical Proceedings (1999); 74(12):1221-1226.
Milstein, C. et al. "Hybrid hybridomas and their use in immunohistochemistry," Nature, (1983); 305(5934):537-540.
Mir et al., "Introduction to Costimulation and Costimulatory Molecules," Developing Costimulatory Molecules for Immunotherapy of Diseases, Elsevier (2015), pp. 1-46.
Morea et al., "Antibody modeling: implications for engineering and design," Methods. (Mar. 2000); 20(3):267-279.
Morgan et al., "Synthetic Fc peptide-mediated regulation of the immune response. I. Characterization of the immunomodulating properties of a synthetic 23-amino acid peptide derived from the sequence of the CH3 domain of human IgG1," J. Exp. Med., 157(3):947-956 (1983).
Morrison et al., "High-flow microinfusion: tissue penetration and pharmacodynamics," American Journal of Physiology—Regulatory, Intensive and Comparative Physiology, Jan. 1994, 266(1), pp. R292-R305.
Morrison, S. L., "Success in specification," Nature, Apr. 1994, 368(6474), pp. 812-813.
Munson et al., "LIGAND: A Versatile Computerized Approach for Characterization of Ligand-Binding Systems," Analytical Biochemistry, Sep. 1980, 107(1), pp. 220-239.
Murakami, R., et al.; "Cyclosporin A enhances interleukin-8 expression by inducing activator protein-1 in human aortic smooth muscle cells," Arterioscler Thromb Vasc Biol. (2003); 23(11):2034-2040.
Neuberger, M., "Generating high-avidity human Mabs in mice," Nature Biotechnology, Jul. 1996, 14(7), pp. 826 (1page).

Padlan E.A., "Anatomy of the Antibody Molecule," Molecular Immunology, 31(3):169-217 (1994).
Portolano S., et al., "Lack of Promiscuity in Autoantigen-Specific H and L Chain Combinations as Revealed by Human H and L Chain Roulette," Journal of Immunology, Feb. 1, 1993, vol. 150, No. 3, pp. 880-887.
Powell et al., "Compendium of excipients for parenteral formulations," PDA Journal of Pharmaceutical Science and Technology. Sep. 1, 1998;52(5):238-311.
Presta, "Selection, design, and engineering of therapeutic antibodies," J Allergy Clin Immunol. (Oct. 2005); 116(4):731-736; quiz 737, 6 pages.
Presta, L.G., "Antibody engineering," Current Opinion in Structural Biology, Aug. 1992, 2(4), pp. 593-596.
Ramakrishnan, S. and Houston, L.L., "Comparison of the Selective Cytotoxic Effects of Immunotoxins Containing Ricin A Chain or Pokeweed Antiviral Protein and Anti-Thy 1.1 Monoclonal Antibodies," Cancer Research, Jan. 1984, 44(1), pp. 201-208.
Renders, L., et al.; "Engineered CD3 antibodies for immunosuppression," Clin. Exp. Immunol., 133(3):307-309 (2003).
Riechmann, L et al. (Mar. 1988), "Reshaping human antibodies for therapy," Nature, vol. 332, No. 6162, pp. 323-327.
Robertson, A-K. L., et al.; "Disruption of TGF-beta signaling in T cells accelerates atherosclerosis," J. Clin. Invest. (2003); 12(9):1342-1350.
Romer P.S., et al.; "Preculture of PBMCs at high cell density increases sensitivity of T-cell responses, revealing cytokine release by CD28 superagonist TGN1412," Blood. (2011); 118(26):6772-6782.
Ruiz et al. "IMGT, the international ImMunoGeneTics database," Nucleic Acids Research, (2000); 28(1):219-221.
Safran et al., "Abstract CT111: Results of a phase 1 dose escalation study of ERY974, an anti-glypican 3 (GPC3)/CD3 bispecific antibody, in patients with advanced solid tumors," Cancer Res., (2021) 81(13_Supplement):CT111, 1 page.
Salmeron A., et al., "A Conformational Epitope Expressed Upon Association of Cd3-epsilon With Either Cd3-delta or Cd3-gamma is the Main Target for Recognition by Anti-cd3 Monoclonal Antibodies," Journal of Immunology, 1991, vol. 147 (9), pp. 3047-3052.
Sano, Y., et al., "Combination of T cell-redirecting bispecific antibody ERY974 and chemotherapy reciprocally enhances efficacy against non-inflamed tumours," Nat Commun. (2022); 13(1):5265, 18 pages.
Shimizu et al., "Cancer immunotherapy-targeted glypican-3 or neoantigens," Cancer Sci., (Mar. 2018); 109(3):531-541.
Shimizu et al., "Next-Generation Cancer Immunotherapy Targeting Glypican-3," Front Oncol., (Apr. 2019); 10:9:248, 10 pages.
Shiraiwa, H., et al., "Engineering a bispecific antibody with a common light chain: Identification and optimization of an anti-CD3 epsilon and anti-GPC3 bispecific antibody, ERY974," Methods. (2019); 154:10-20.
Sholter, D.E., et al.; "Adverse effects of corticosteroids on the cardiovascular system," Can. J. Cardiol., vol. 16(4):505-11 (2000).
Shopes "A genetically engineered human IgG mutant with enhanced cytolytic activity," Journal of immunology (Baltimore, Md.: 1950). May 1, 1992; 148(9): 2918-22.
Singh, A., et al., "Overcoming the challenges associated with CD3+ T-cell redirection in cancer," Br J Cancer. (2021); 124(6):1037-1048.
Skokos, D., et al., "A class of costimulatory CD28-bispecific antibodies that enhance the antitumor activity of CD3-bispecific antibodies," Sci Transl Med. (2020); 12(525):eaaw7888, 15 pages.
Stebbings R., et al.; ""Cytokine storm" in the phase I trial of monoclonal antibody TGN1412: better understanding the causes to improve preclinical testing of immunotherapeutics," J Immunol. (2007); 179(5):3325-3331.
Stevenson et al., "A chimeric antibody with dual Fc regions (bisFabFc) prepared by manipulations at the IgG hinge," Anti-Cancer Drug Design, Mar. 1989, 3(4):219-230.
Stober et al.; "The pathogenesis of mucosal inflammation in murine models of inflammatory bowel disease and Crohn disease," Ann Intern Med. 1998; 128(10):848-856 (1998).

(56) References Cited

OTHER PUBLICATIONS

Strohl, W.R., "Optimization of Fc-mediated effector functions of monoclonal antibodies," Current Opinion in Biotechnology, Dec. 2009, 20(6), pp. 685-691.

Suresh et al., "Bispecific Monoclonal Antibodies from Hybrid Hybridomas," Methods in Enzymology, Jan. 1986, vol. 121, pp. 210-228.

Thornton et al. "Prediction of progress at last," Nature, (1991); 354(6349):105-106.

Tran, G.T., et al.; "Reversal of experimental allergic encephalomyelitis with non-mitogenic, non-depleting anti-CD3 mAb therapy with a preferential effect on T(h)1 cells that is augmented by IL-4," Int. Immunol., 13(9):1109-1120 (2001).

Traunecker et al., "Bispecific single chain molecules (Janusins) target cytotoxic lymphocytes on HIV infected cells," The EMBO Journal, Dec. 1991, 10(12), pp. 3655-3659.

Tutt et al., "Trispecific F(ab')3 Derivatives that Use Cooperative Signaling via the TCR/CD3 Complex and CD2 to Activate and Redirect Resting Cytotoxic T Cells," The Journal of Immunology, Jul. 1991, 147(1), pp. 60-69.

Uzel et al., "Cytokines in juvenile dermatomyositis pathophysiology: potential and challenge," Current Opinion in Rheumatology, 15(6):691-697 (2003).

Van Der Woude, C.J., et al., "Phase I, double-blind, randomized, placebo-controlled, dose-escalation study of NI-0401 (a fully human anti-CD3 monoclonal antibody) in patients with moderate to severe active Crohn's disease," Clinical Trial, Inflamm Bowel Dis. (2010); 16(10):1708-1716.

Vaughan et al., "Human antibodies with sub-nanomolar affinities isolated from a large non-immunized phage display library," Nature Biotechnology, Mar. 1996, 14(3), pp. 309-314.

Verhoeyen, M., et al., "Reshaping human antibodies: grafting an antilysozyme activity," Science, Mar. 1988, 239(4847), pp. 1534-1536.

Vitetta et al., "Redesigning Nature's Poisons to Create Anti-Tumor Reagents," Science, Nov. 1987, 238(4830), pp. 1098-1104.

Von Herrath, M.G., et al.; "Nonmitogenic CD3 antibody reverses virally induced (rat insulin promoter-lymphocytic choriomeningitis virus) autoimmune diabetes without impeding viral clearance," J. Immunol., 168(2):933-941 (2002).

Waite, J.C., et al.; "Tumor-targeted CD28 bispecific antibodies enhance the antitumor efficacy of PD-1 immunotherapy," Sci Transl Med. (2020); 12(549):eaba2325, 16 pages.

Wang, W., "Lyophilization and development of solid protein pharmaceuticals," International Journal of Pharmaceutics, Aug. 2000, 203(1-2), pp. 1-60.

Webster's New World Dictionary Definition: "Prevent," Third College Edition, 1988, see p. 1067-68 (Year: 1988), 4 pages.

Wilkinson, D., "Ultimate Abs," The Scientist 25, Apr. 17, 2000, vol. 14, No. 8, pp. 25-28.

Winter et al., "Humanized Antibodies," Immunology Today 243, vol. 14, No. 6, May 1993, pp. 243-246.

Woodle, E.S., et al., "Phase I trial of a humanized, Fc receptor nonbinding OKT3 antibody, huOKT3gamma1 (Ala-Ala) in the treatment of acute renal allograft rejection," Transplantation (1999); 68(5):608-616.

Wright et al., "Genetically engineered antibodies: progress and prospects," Crit. Rev. Immunol., vol. 12(3,4):125-168 (1992).

Wu et al., "GPC-3 in hepatocellular carcinoma: current perspectives," J Hepatocell Carcinoma., (Nov. 2016); 8:3, pp. 63-67.

Xu, D., et al., "In vitro characterization of five humanized OKT3 effector function variant antibodies," Cellular Immunology (2000); 200(1):16-26.

Yang, S.Y., et al., "A common pathway for T lymphocyte activation involving both the CD3-Ti complex and CD2 sheep erythrocyte receptor determinants," The Journal of Immunology (1986); 137(4):1097-1100.

Yang, Y., et al., "Cellular and humoral immune responses to viral antigens create barriers to lung-directed gene therapy with recombinant adenoviruses," J Virol., (1995); 69(4):2004-2015.

Yasukawa, M.; "Treatment of transfusion-associated graft-versus-host disease," Japanese Journal of Clinical Medicine (1997); 55(9):2290-2295 (Abstract Only); 2 pages.

Yoshino N., et al., "Upgrading of Flow Cytometric Analysis for Absolute Counts, Cytokines and Other Antigenic Molecules of Cynomolgus Monkeys (*Macaca fascicularis*) by Using Anti-human Cross-reactive Antibodies," Experimental Animals, 2000, vol. 49(2), pp. 97-110.

Yu et al., "A novel targeted GPC3/CD3 bispecific antibody for the treatment hepatocellular carcinoma," Cancer Biol Ther., (Jul. 2020); 21(7):597-603.

Yu, L., et al.; "Development of a Tetravalent T-Cell Engaging Bispecific Antibody Against Glypican-3 for Hepatocellular Carcinoma," J Immunother., (2021); 44(3):106-113.

Zeng, V., et al.; "Abtract 698: PDL1-targeted CD28 costimulatory bispecific antibodies enhance T cell activation in solid tumors," Journal for Immunotherapy of Cancer, London (2021); 9(Suppl 2):A726-A726, 1 page.

\* cited by examiner

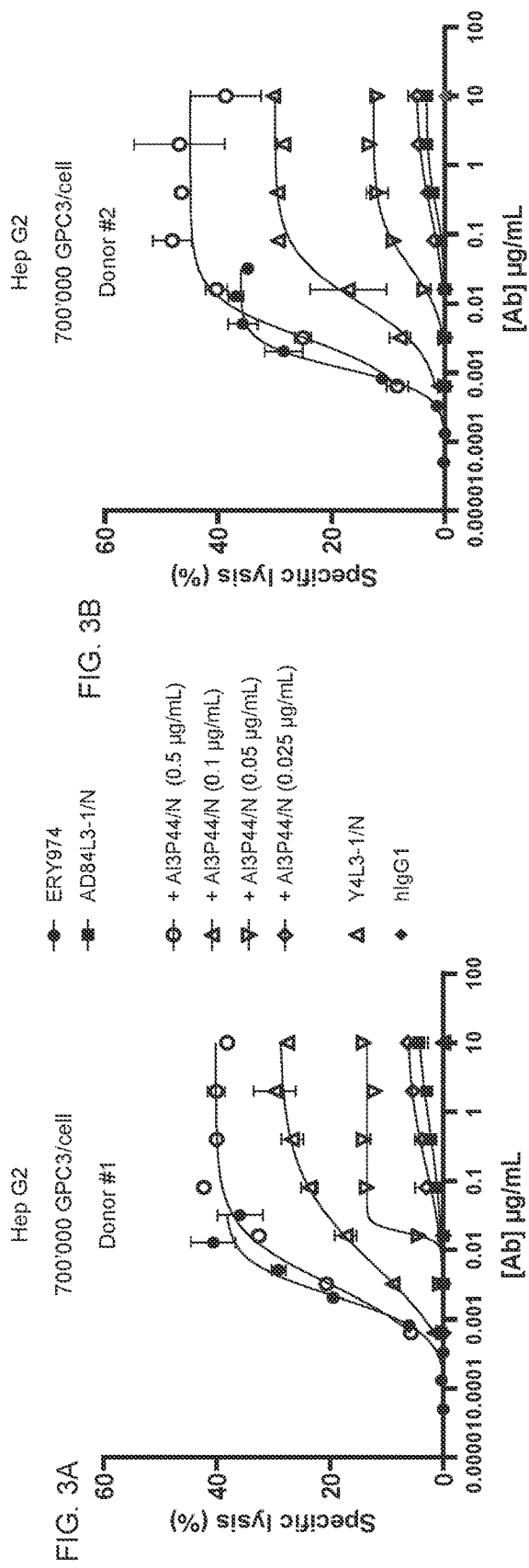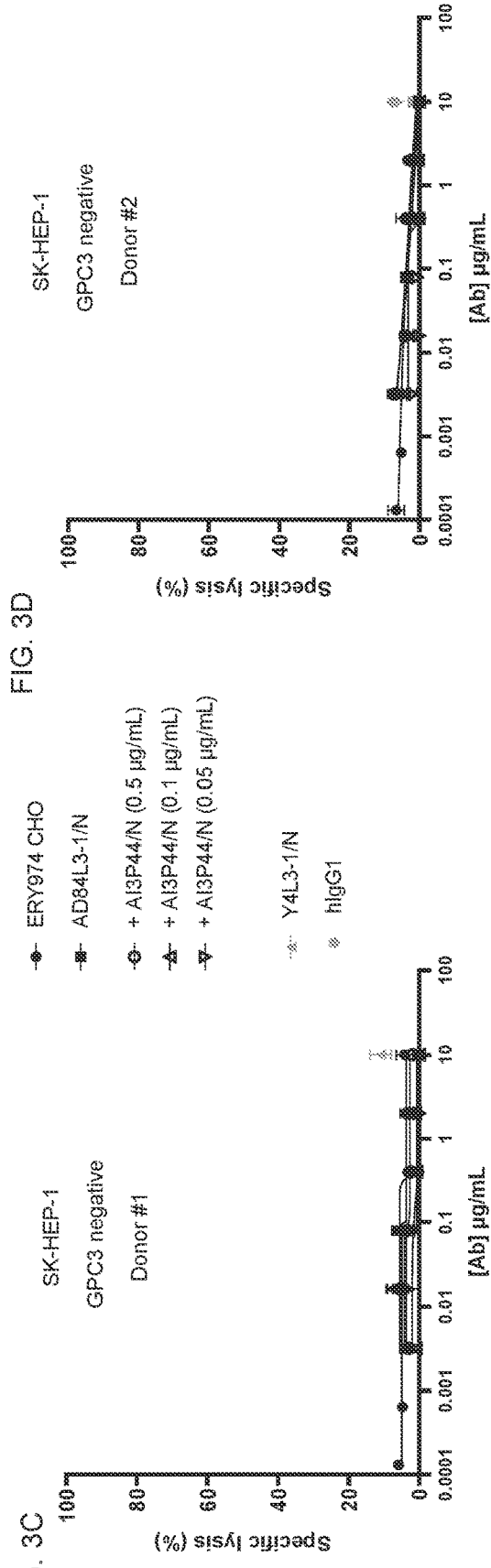

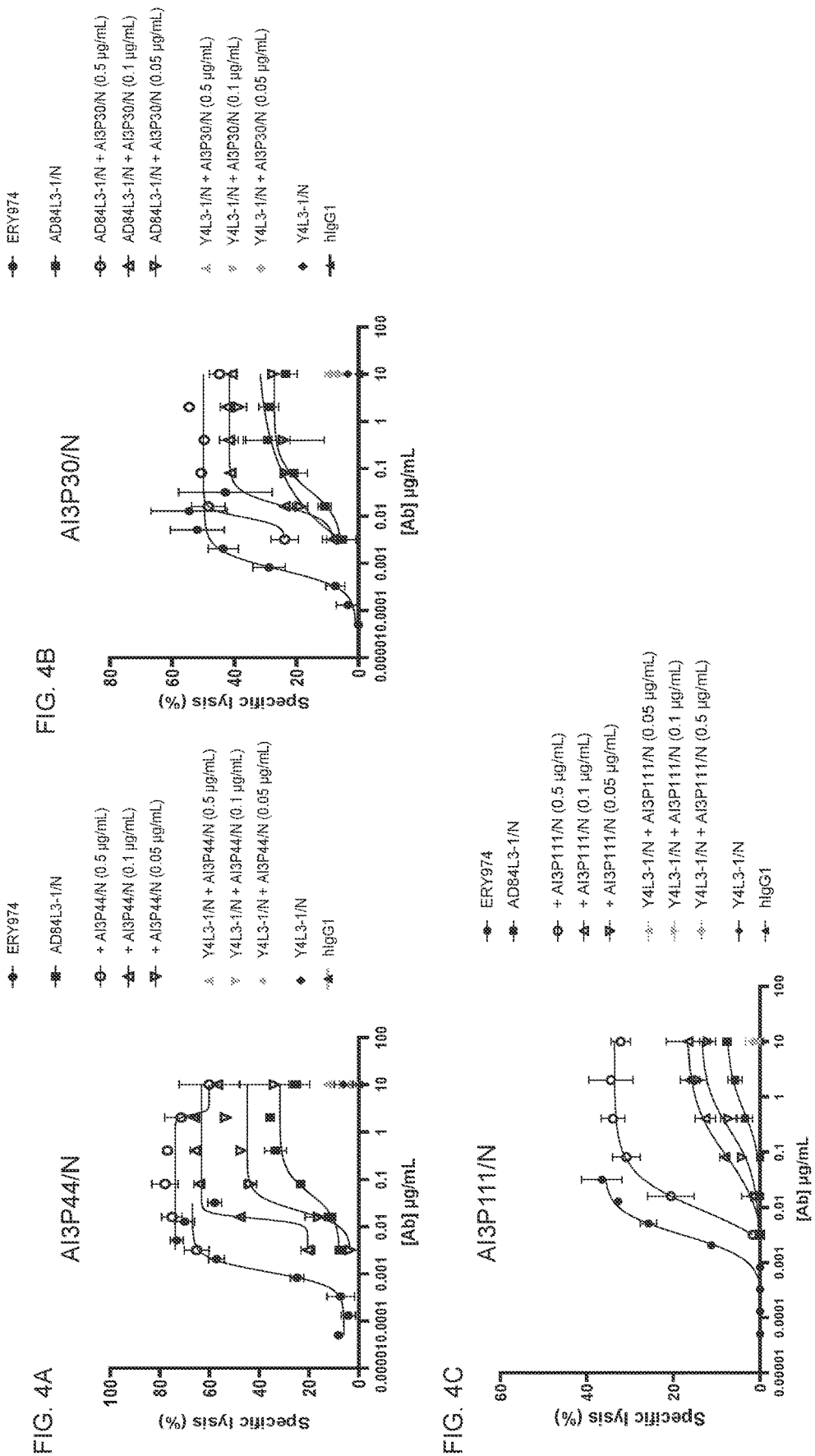

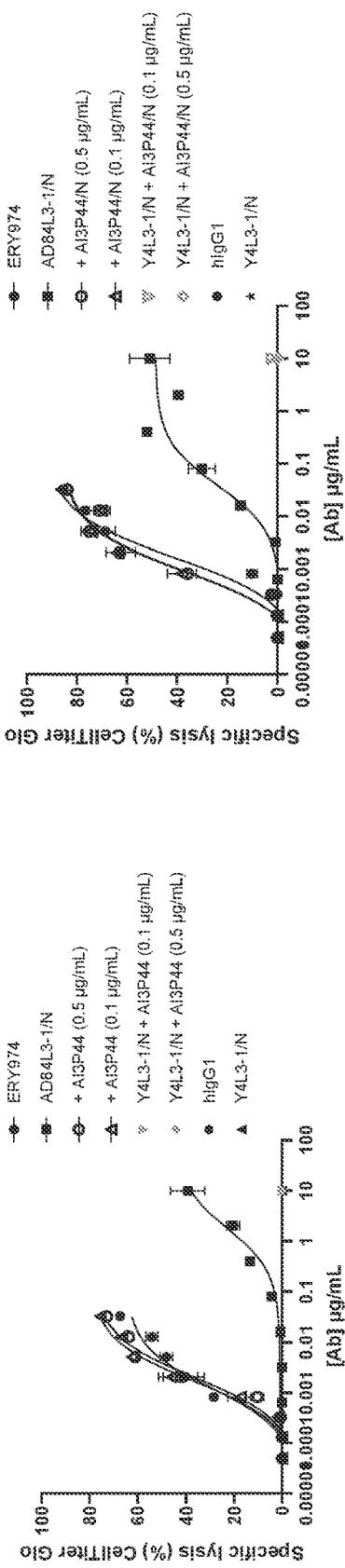
FIG. 10A
FIG. 10C
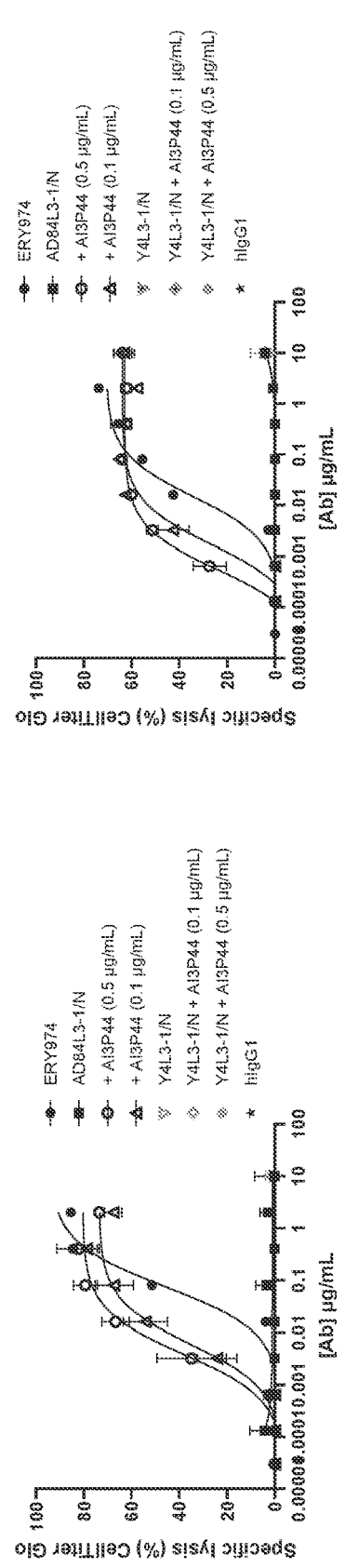
FIG. 10B
FIG. 10D

SEQUENCE LISTING

```
Sequence total quantity: 60
SEQ ID NO: 1            moltype = AA  length = 8
FEATURE                 Location/Qualifiers
source                  1..8
                        mol_type = protein
                        organism = synthetic construct
SEQUENCE: 1
GFTFSSYA                                                                    8

SEQ ID NO: 2            moltype = AA  length = 8
FEATURE                 Location/Qualifiers
source                  1..8
                        mol_type = protein
                        organism = synthetic construct
SEQUENCE: 2
ISGSGGST                                                                    8

SEQ ID NO: 3            moltype = AA  length = 9
FEATURE                 Location/Qualifiers
source                  1..9
                        mol_type = protein
                        organism = synthetic construct
SEQUENCE: 3
AKSYGAFDY                                                                   9

SEQ ID NO: 4            moltype = AA  length = 116
FEATURE                 Location/Qualifiers
source                  1..116
                        mol_type = protein
                        organism = synthetic construct
SEQUENCE: 4
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKSY GAFDYWGQGT LVTVSS      116

SEQ ID NO: 5            moltype = AA  length = 445
FEATURE                 Location/Qualifiers
source                  1..445
                        mol_type = protein
                        organism = synthetic construct
SEQUENCE: 5
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKSY GAFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALAAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 6            moltype = AA  length = 5
FEATURE                 Location/Qualifiers
source                  1..5
                        mol_type = protein
                        organism = synthetic construct
SEQUENCE: 6
TYAMN                                                                       5

SEQ ID NO: 7            moltype = AA  length = 19
```

```
FEATURE                 Location/Qualifiers
source                  1..19
                        mol_type = protein
                        organism = synthetic construct
SEQUENCE: 7
RIRSKYNNYA TYYADSVKD                                                    19

SEQ ID NO: 8            moltype = AA  length = 14
FEATURE                 Location/Qualifiers
source                  1..14
                        mol_type = protein
                        organism = synthetic construct
SEQUENCE: 8
HGNFGNSYVS WFAY                                                         14

SEQ ID NO: 9            moltype = AA  length = 125
FEATURE                 Location/Qualifiers
source                  1..125
                        mol_type = protein
                        organism = synthetic construct
SEQUENCE: 9
EVQLVESGGG LVQPGGSLKL SCAASGFTFN TYAMNWVRQA PGKGLEWVGR IRSKYNNYAT        60
YYADSVKDRF TISRDDSKNT AYLQMNSLKT EDTAVYYCVR HGNFGNSYVS WFAYWGQGTL       120
VTVSS                                                                  125

SEQ ID NO: 10           moltype = AA  length = 454
FEATURE                 Location/Qualifiers
source                  1..454
                        mol_type = protein
                        organism = synthetic construct
SEQUENCE: 10
EVQLVESGGG LVQPGGSLKL SCAASGFTFN TYAMNWVRQA PGKGLEWVGR IRSKYNNYAT        60
YYADSVKDRF TISRDDSKNT AYLQMNSLKT EDTAVYYCVR HGNFGNSYVS WFAYWGQGTL       120
VTVSSASTKG PSVFPLAPSS KSTSGGTAAL GCLVKDYFPE PVTVSWNSGA LTSGVHTFPA       180
VLQSSGLYSL SSVVTVPSSS LGTQTYICNV NHKPSNTKVD KRVEPKSCDK THTCPPCPAP       240
EAAGGPSVFL FPPKPKDTLM ISRTPEVTCV VVDVSHEDPE VKFNWYVDGV EVHNAKTKPR       300
EEQYNSTYRV VSVLTVLHQD WLNGKEYKCK VSNKALAAPI EKTISKAKGQ PREPQVYTLP       360
PSREEMTKNQ VSLTCLVKGF YPSDIAVEWE SNGQPENNYK TTPPVLDSDG SFFLYSKLTV       420
DKSRWQQGNV FSCSVMHEAL HNHYTQKSLS LSPG                                  454

SEQ ID NO: 11           moltype = AA  length = 14
FEATURE                 Location/Qualifiers
source                  1..14
                        mol_type = protein
                        organism = synthetic construct
SEQUENCE: 11
RSSTGAVTTS NYAN                                                         14

SEQ ID NO: 12           moltype = AA  length = 7
FEATURE                 Location/Qualifiers
source                  1..7
                        mol_type = protein
                        organism = synthetic construct
SEQUENCE: 12
GTNKRAP                                                                  7

SEQ ID NO: 13           moltype = AA  length = 9
FEATURE                 Location/Qualifiers
source                  1..9
                        mol_type = protein
                        organism = synthetic construct
SEQUENCE: 13
ALWYKQRWV                                                                9

SEQ ID NO: 14           moltype = AA  length = 109
FEATURE                 Location/Qualifiers
source                  1..109
                        mol_type = protein
                        organism = synthetic construct
SEQUENCE: 14
QTVVTQEPSL TVSPGGTVTL TCRSSTGAVT TSNYANWFQQ KPGQAPRGLI GGTNKRAPGT        60
PARFSGSLLG GKAALTLSGA QPEDEAEYYC ALWYKQRWVF GGGTKLTVL                  109

SEQ ID NO: 15           moltype = AA  length = 215
FEATURE                 Location/Qualifiers
source                  1..215
                        mol_type = protein
                        organism = synthetic construct
SEQUENCE: 15
```

```
QTVVTQEPSL TVSPGGTVTL TCRSSTGAVT TSNYANWFQQ KPGQAPRGLI GGTNKRAPGT    60
PARFSGSLLG GKAALTLSGA QPEDEAEYYC ALWYKQRWVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                              215

SEQ ID NO: 16          moltype = AA   length = 7
FEATURE                Location/Qualifiers
source                 1..7
                       mol_type = protein
                       organism = synthetic construct
SEQUENCE: 16
QKVTNRE                                                              7

SEQ ID NO: 17          moltype =    length =
SEQUENCE: 17
000

SEQ ID NO: 18          moltype = AA   length = 11
FEATURE                Location/Qualifiers
source                 1..11
                       mol_type = protein
                       organism = synthetic construct
SEQUENCE: 18
QQWALSPRGW V                                                        11

SEQ ID NO: 19          moltype = AA   length = 110
FEATURE                Location/Qualifiers
source                 1..110
                       mol_type = protein
                       organism = synthetic construct
SEQUENCE: 19
EIVLTQSPGT LSLSPGERAT LSCRASQKVT NRELAWYQQK PGQAPRLLIY GATTKATGIP    60
DRFSGSGSGT DFTLTISRLE PEDFAVYYCQ QWALSPRGWV FGQGTKVEIK              110

SEQ ID NO: 20          moltype = AA   length = 217
FEATURE                Location/Qualifiers
source                 1..217
                       mol_type = protein
                       organism = synthetic construct
SEQUENCE: 20
EIVLTQSPGT LSLSPGERAT LSCRASQKVT NRELAWYQQK PGQAPRLLIY GATTKATGIP    60
DRFSGSGSGT DFTLTISRLE PEDFAVYYCQ QWALSPRGWV FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 21          moltype = AA   length = 7
FEATURE                Location/Qualifiers
source                 1..7
                       mol_type = protein
                       organism = synthetic construct
SEQUENCE: 21
QKVTNRE                                                              7

SEQ ID NO: 22          moltype =    length =
SEQUENCE: 22
000

SEQ ID NO: 23          moltype = AA   length = 11
FEATURE                Location/Qualifiers
source                 1..11
                       mol_type = protein
                       organism = synthetic construct
SEQUENCE: 23
QQWALSPRGW V                                                        11

SEQ ID NO: 24          moltype = AA   length = 110
FEATURE                Location/Qualifiers
source                 1..110
                       mol_type = protein
                       organism = synthetic construct
SEQUENCE: 24
EIVLTQSPGT LSLSPGERAT LSCRASQKVT NRELAWYQQK PGQAPRLLIY GAKIRAKGIP    60
DRFSGSGSGT DFTLTISRLE PEDFAVYYCQ QWALSPRGWV FGQGTKVEIK              110

SEQ ID NO: 25          moltype = AA   length = 217
FEATURE                Location/Qualifiers
source                 1..217
                       mol_type = protein
                       organism = synthetic construct
```

```
SEQUENCE: 25
EIVLTQSPGT LSLSPGERAT LSCRASQKVT NRELAWYQQK PGQAPRLLIY GAKIRAKGIP    60
DRFSGSGSGT DFTLTISRLE PEDFAVYYCQ QWALSPRGWV FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 26          moltype = AA   length = 8
FEATURE                Location/Qualifiers
source                 1..8
                       mol_type = protein
                       organism = synthetic construct
SEQUENCE: 26
SGSISYDD                                                              8

SEQ ID NO: 27          moltype =      length =
SEQUENCE: 27
000

SEQ ID NO: 28          moltype = AA   length = 9
FEATURE                Location/Qualifiers
source                 1..9
                       mol_type = protein
                       organism = synthetic construct
SEQUENCE: 28
QSWDLRHRV                                                             9

SEQ ID NO: 29          moltype = AA   length = 110
FEATURE                Location/Qualifiers
source                 1..110
                       mol_type = protein
                       organism = synthetic construct
SEQUENCE: 29
NFMLTQPHSV SESPGKTVTI SCTRSSGSIS YDDVQWYQQR PGSSPTTVIY FNNLRPSGVP    60
DRFSGSIDSS SNSASLTISG LKTEDEADYY CQSWDLRHRV FGGGTKLTVL              110

SEQ ID NO: 30          moltype = AA   length = 216
FEATURE                Location/Qualifiers
source                 1..216
                       mol_type = protein
                       organism = synthetic construct
SEQUENCE: 30
NFMLTQPHSV SESPGKTVTI SCTRSSGSIS YDDVQWYQQR PGSSPTTVIY FNNLRPSGVP    60
DRFSGSIDSS SNSASLTISG LKTEDEADYY CQSWDLRHRV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 31          moltype = AA   length = 9
FEATURE                Location/Qualifiers
source                 1..9
                       mol_type = protein
                       organism = synthetic construct
SEQUENCE: 31
SSDVPEDAL                                                             9

SEQ ID NO: 32          moltype =      length =
SEQUENCE: 32
000

SEQ ID NO: 33          moltype = AA   length = 11
FEATURE                Location/Qualifiers
source                 1..11
                       mol_type = protein
                       organism = synthetic construct
SEQUENCE: 33
SSWDFGTGSK V                                                         11

SEQ ID NO: 34          moltype = AA   length = 111
FEATURE                Location/Qualifiers
source                 1..111
                       mol_type = protein
                       organism = synthetic construct
SEQUENCE: 34
QSALTQPASV SGSPGQSITI SCTGTSSDVP EDALVSWYQQ HPGKAPKLMI YYDSTRPSGV    60
SNRFSGSKSG NTASLTISGL QAEDEADYYC SSWDFGTGSK VFGGGTKLTV L            111

SEQ ID NO: 35          moltype = AA   length = 217
FEATURE                Location/Qualifiers
source                 1..217
                       mol_type = protein
```

```
                        organism = synthetic construct
SEQUENCE: 35
QSALTQPASV SGSPGQSITI SCTGTSSDVP EDALVSWYQQ HPGKAPKLMI YYDSTRPSGV    60
SNRFSGSKSG NTASLTISGL QAEDEADYYC SSWDFGTGSK VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 36           moltype = AA    length = 8
FEATURE                 Location/Qualifiers
source                  1..8
                        mol_type = protein
                        organism = synthetic construct
SEQUENCE: 36
SSNIGTYY                                                             8

SEQ ID NO: 37           moltype =       length =
SEQUENCE: 37
000

SEQ ID NO: 38           moltype = AA    length = 9
FEATURE                 Location/Qualifiers
source                  1..9
                        mol_type = protein
                        organism = synthetic construct
SEQUENCE: 38
QSIGFLSLV                                                            9

SEQ ID NO: 39           moltype = AA    length = 108
FEATURE                 Location/Qualifiers
source                  1..108
                        mol_type = protein
                        organism = synthetic construct
SEQUENCE: 39
QSVLTQPPSA SGTPGQRVTI SCSGSSSNIG TYYVNWYQQL PGTAPKLLIY SNNERPSGVP    60
DRFSGSKSGT SASLAISGLQ SEDEADYYCQ SIGFLSLVFG GGTKLTVL                108

SEQ ID NO: 40           moltype = AA    length = 214
FEATURE                 Location/Qualifiers
source                  1..214
                        mol_type = protein
                        organism = synthetic construct
SEQUENCE: 40
QSVLTQPPSA SGTPGQRVTI SCSGSSSNIG TYYVNWYQQL PGTAPKLLIY SNNERPSGVP    60
DRFSGSKSGT SASLAISGLQ SEDEADYYCQ SIGFLSLVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 41           moltype = AA    length = 12
FEATURE                 Location/Qualifiers
source                  1..12
                        mol_type = protein
                        organism = synthetic construct
SEQUENCE: 41
QSVLYSSNNK NY                                                       12

SEQ ID NO: 42           moltype =       length =
SEQUENCE: 42
000

SEQ ID NO: 43           moltype = AA    length = 9
FEATURE                 Location/Qualifiers
source                  1..9
                        mol_type = protein
                        organism = synthetic construct
SEQUENCE: 43
QQNLRPPET                                                            9

SEQ ID NO: 44           moltype = AA    length = 113
FEATURE                 Location/Qualifiers
source                  1..113
                        mol_type = protein
                        organism = synthetic construct
SEQUENCE: 44
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQNLRP PETFGQGTKV EIK          113

SEQ ID NO: 45           moltype = AA    length = 220
FEATURE                 Location/Qualifiers
source                  1..220
```

```
                       mol_type = protein
                       organism = synthetic construct
SEQUENCE: 45
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQNLRP PETFGQGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                        220

SEQ ID NO: 46          moltype = AA   length = 11
FEATURE                Location/Qualifiers
source                 1..11
                       mol_type = protein
                       organism = synthetic construct
SEQUENCE: 46
GDLLEFAGKT Y                                                        11

SEQ ID NO: 47          moltype =      length =
SEQUENCE: 47
000

SEQ ID NO: 48          moltype = AA   length = 11
FEATURE                Location/Qualifiers
source                 1..11
                       mol_type = protein
                       organism = synthetic construct
SEQUENCE: 48
MQAHGSKIGF T                                                        11

SEQ ID NO: 49          moltype = AA   length = 114
FEATURE                Location/Qualifiers
source                 1..114
                       mol_type = protein
                       organism = synthetic construct
SEQUENCE: 49
DIVMTQTPLS LSVTPGQPAS ISCKSSGDLL EFAGKTYLYW YLQKPGQPPQ LLIYEVSNRF    60
SGVPDRFSGS GSGTDFTLKI SRVEAEDVGV YYCMQAHGSK IGFTFGQGTK VEIK         114

SEQ ID NO: 50          moltype = AA   length = 221
FEATURE                Location/Qualifiers
source                 1..221
                       mol_type = protein
                       organism = synthetic construct
SEQUENCE: 50
DIVMTQTPLS LSVTPGQPAS ISCKSSGDLL EFAGKTYLYW YLQKPGQPPQ LLIYEVSNRF    60
SGVPDRFSGS GSGTDFTLKI SRVEAEDVGV YYCMQAHGSK IGFTFGQGTK VEIKRTVAAP   120
SVFIFPPSDE QLKSGTASVV CLLNNFYPRE AKVQWKVDNA LQSGNSQESV TEQDSKDSTY   180
SLSSTLTLSK ADYEKHKVYA CEVTHQGLSS PVTKSFNRGE C                      221

SEQ ID NO: 51          moltype = AA   length = 12
FEATURE                Location/Qualifiers
source                 1..12
                       mol_type = protein
                       organism = synthetic construct
SEQUENCE: 51
QSVLYSSNNK NY                                                       12

SEQ ID NO: 52          moltype =      length =
SEQUENCE: 52
000

SEQ ID NO: 53          moltype = AA   length = 9
FEATURE                Location/Qualifiers
source                 1..9
                       mol_type = protein
                       organism = synthetic construct
SEQUENCE: 53
QQNFRPPET                                                            9

SEQ ID NO: 54          moltype = AA   length = 113
FEATURE                Location/Qualifiers
source                 1..113
                       mol_type = protein
                       organism = synthetic construct
SEQUENCE: 54
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQNFRP PETFGGGTKV EIK          113

SEQ ID NO: 55          moltype = AA   length = 220
FEATURE                Location/Qualifiers
```

```
                    source          1..220
                                    mol_type = protein
                                    organism = synthetic construct
SEQUENCE: 55
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVG VYYCQQNFRP PETFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 56   moltype = AA  length = 214
FEATURE         Location/Qualifiers
source          1..214
                mol_type = protein
                organism = synthetic construct
SEQUENCE: 56
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPNTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 57   moltype = AA  length = 440
FEATURE         Location/Qualifiers
source          1..440
                mol_type = protein
                organism = synthetic construct
SEQUENCE: 57
QVQLVQSGAE VKKPGASVTV SCKASGYTFT DYEMHWIRQP PGEGLEWIGA IDGPTPDTAY    60
SEKFKGRVTL TADKSTSTAY MELSSLTSED TAVYYCTRFY SYTYWGQGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTQTYTCNV DHKPSNTKVD KRVESKYGPP CPPCPAPEFR GGPKVFLFPP   240
KPKDTLMISR TPEVTCVVVD VSQEDPEVQF NWYVDGVEVH NAKTKPREEQ FASTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWQSNG QTENNYKTTP PVLDSDGSFF LYSKLTVDKS RWQEGNVFSC   420
SVMHEALHNH YTQESLSLSP                                               440

SEQ ID NO: 58   moltype = AA  length = 219
FEATURE         Location/Qualifiers
source          1..219
                mol_type = protein
                organism = synthetic construct
SEQUENCE: 58
DIVMTQSPLS LPVTPGEPAS ISCRSSQPLV HSNRNTYLHW YQQKPGQAPR LLIYKVSNRF    60
SGVPDRFSGS GSGTDFTLKI SRVEAEDVGV YYCGQGTQVP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 59   moltype = AA  length = 447
FEATURE         Location/Qualifiers
source          1..447
                mol_type = protein
                organism = synthetic construct
SEQUENCE: 59
QVQLVESGGG VVQPGGSLRL SCAASGFTFS NAWMHWVRQA PGKGLEWVAQ IKDKSQNYAT    60
YVAESVKGRF TISRADSKNS IYLQMNSLKT EDTAVYYCRY VHYAAGYGVD IWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFRGGP   240
KVFLFPPKPK DTLMISRTPE VTCVVVDVSQ EDPEVQFNWY VDGVEVHNAK TKPREEQFAS   300
TYRVVSVLTV LHQDWLNGKE YKCKVSNKGL PSSIEKTISK AKGQPREPQV YTLPPSQKEM   360
TKNQVSLTCL VKGFYPSDIA VEWESNGQPE NNYKTTPPVL DSDGSFFLYS KLTVDKSRWQ   420
EGNVFSCSVM HEALHNRYTQ KSLSLSP                                       447

SEQ ID NO: 60   moltype = AA  length = 219
FEATURE         Location/Qualifiers
source          1..219
                mol_type = protein
                organism = synthetic construct
SEQUENCE: 60
DIVMTQSPLS LPVTPGEPAS ISCRSSQPLV HSNRNTYLHW YQQKPGQAPR LLIYKVSNRF    60
SGVPDRFSGS GSGTDFTLKI SRVEAEDVGV YYCGQGTQVP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

BISPECIFIC GPC3XCD28 AND GPC3XCD3 ANTIBODIES AND THEIR COMBINATION FOR TARGETED KILLING OF GPC3 POSITIVE MALIGNANT CELLS

RELATED APPLICATIONS

The application claims priority to, and the benefit of, U.S. Provisional Application No. 63/319,709, filed on Mar. 14, 2022, and U.S. Provisional Application No. 63/328,586, filed on Apr. 7, 2022, the contents of each of which are incorporated by reference herein in their entireties.

INCORPORATION BY REFERENCE OF SEQUENCE LISTING

The contents of the electronic sequence listing (NOVI_725_001US_SubSeqList_ST26.xml; Size: 53,237 bytes; and Date of Creation: Apr. 25, 2024) are herein incorporated by reference in its entirety.

FIELD

The present invention relates to fully human bispecific antibodies (such as KA-bodies) targeting glypican-3 (GPC3)×CD28 (CD28-agonistic) and to bispecific antibodies targeting GPC3×CD3, and to the combination of GPC3× CD3 with GPC3×CD28 of the invention. Upon the engagement of GPC3 on GPC3-expressing tumor cells and CD28 on T-cells, the combination treatment of the invention is capable of boosting T cell activation and tumoricidal activity compared with a GPC3×CD3 single agent treatment. The invention further relates to methods of using such antibodies in the treatment of GPC3 positive malignancies.

BACKGROUND OF THE INVENTION

In the past years, novel approaches to stimulate the body's own immune cells to better attack and kill cancer cells were developed. Examples of successful cancer immunotherapies are monoclonal antibodies capable of blocking so-called immune checkpoints. Currently approved immune checkpoint inhibitors (ICI) block CTLA-4 (e.g., Ipilimumab, sold under the brand name Yervoy), PD-1 (e.g., Pembrolizumab, sold under the brand name Keytruda and Cemiplimab, sold under the brand name Libtayo) and PD-L1 (e.g., Atezolizumab, sold under the brand name Tecentriq). ICIs can induce durable anti-tumor responses in several but not all cancer types with responses limited to a subpopulation of patients.

Other approved cancer immunotherapies include T cell bispecific antibodies-bridging T cells to target cells expressing a tumor associated antigen (TAA) via the CD3 receptor on T cells. A different strategy is the use of Chimeric Antigen Receptor (CAR) T cells. Despite the very good anti-tumor responses observed with treatments using T cell bispecific antibodies or CAR T cells in hematological malignancies, there have been no significant breakthroughs of these approaches in the context of solid cancers to date, leaving many cancer patients with no therapeutic options.

Therefore, and in spite of the success of these immunotherapies in some cancer types, a large fraction of cancer patients lacks valid therapeutic options, highlighting the need for new treatments. The use of molecules capable of activating the immune system by targeting costimulatory signals on T cells has not been fully explored and may open the way to novel therapeutic options for solid cancer patients.

A need exists for compositions and methods for targeting T-cell activation useful for treating solid cancers. Provided herein are methods and compositions addressing this need.

SUMMARY OF THE INVENTION

The disclosure provides a bispecific antibody comprising: a. a first antigen binding domain that binds to CD3; wherein the first antigen binding domain comprises: i. a first heavy chain variable region having a complementarity determining region 1 (CDRH1) comprising the amino acid sequence of SEQ ID NO: 6; a complementarity determining region 2 (CDRH2) comprising the amino acid sequence of SEQ ID NO: 7; and a complementarity determining region 3 (CDRH3) comprising the amino acid sequence of SEQ ID NO: 8; and ii. a first light chain variable region having: a CDRL1 comprising the amino acid sequence of SEQ ID NO: 11; a CDRL2 comprising the amino acid sequence of SEQ ID NO: 12; and a CDRL3 comprising the amino acid sequence of SEQ ID NO: 13; and b. a second antigen binding domain that binds to GPC3, wherein the second antigen binding domain comprises: i. a second heavy chain variable region having a CDRH1 comprising the amino acid sequence of SEQ ID NO: 6; a CDRH2 comprising the amino acid sequence of SEQ ID NO: 7; and a CDRH3 comprising the amino acid sequence of SEQ ID NO: 8; and ii. second light chain variable region having: 1. a CDRL1 comprising the amino acid sequence of SEQ ID NO: 16; a CDRL2 comprising the amino acid sequence of SEQ ID NO: 17; and a CDRL3 comprising the amino acid sequence of SEQ ID NO: 18; or 2. a CDRL1 comprising the amino acid sequence of SEQ ID NO: 21; a CDRL2 comprising the amino acid sequence of SEQ ID NO: 22; and a CDRL3 comprising the amino acid sequence of SEQ ID NO: 23.

In some embodiments, the first heavy chain variable region and the second heavy chain variable region comprises the amino acid sequence of SEQ ID NO: 9. In some embodiments, the first heavy chain and the second heavy chain comprises the amino acid sequence of SEQ ID NO: 10. In some embodiments, the first light chain variable region comprises the amino acid sequence of SEQ ID NO: 14. In some embodiments, the first light chain comprises the amino acid sequence of SEQ ID NO: 15.

In some embodiments, the second light chain variable region of a. part b. ii. 1. comprises the amino acid sequence of SEQ ID NO: 19; or b. part b. ii. 2. comprises the amino acid sequence of SEQ ID NO: 24.

In some embodiments, the second light chain of a. part b. ii. 1. comprises the amino acid sequence of SEQ ID NO: 20; or b. part b. ii. 2. comprises the amino acid sequence of SEQ ID NO: 25.

The disclosure provides a bispecific antibody comprising: a. a first antigen binding domain that binds to CD28; wherein the first antigen binding domain comprises: i. a first heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and ii. a first light chain variable region having: 1. a CDRL1 comprising the amino acid sequence of SEQ ID NO: 41; a CDRL2 comprising the amino acid sequence of SEQ ID NO: 42; and a CDRL3 comprising the amino acid sequence of SEQ ID NO: 43; or 2. a CDRL1 comprising the amino acid sequence of SEQ ID NO: 46; a CDRL2 comprising the amino acid sequence of SEQ ID NO: 47; and a CDRL3 comprising the amino acid sequence of SEQ ID NO: 48; or 3. a CDRL1 comprising the amino acid sequence of SEQ ID NO: 51; a CDRL2 comprising the amino acid sequence of SEQ ID NO: 52; and a CDRL3 comprising the amino acid sequence of SEQ ID NO: 53; and b. a second antigen binding domain that binds GPC3, wherein the second antigen binding domain comprises: i. a second heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and ii. second light chain variable region having: 1. a CDRL1 comprising the amino acid sequence of SEQ ID NO: 26; a CDRL2 comprising the amino acid sequence of SEQ ID NO: 27; and a CDRL3 comprising the amino acid sequence of SEQ ID NO: 28; or 2. a CDRL1 comprising the amino acid sequence of SEQ ID NO: 31; a CDRL2 comprising the amino acid sequence of SEQ ID NO: 32; and a CDRL3 comprising the amino acid sequence of SEQ ID NO: 33; or 3. a CDRL1 comprising the amino acid sequence of SEQ ID NO: 36; a CDRL2 comprising the amino acid sequence of SEQ ID NO: 37; and a CDRL3 comprising the amino acid sequence of SEQ ID NO: 38.

In some embodiments, the first heavy chain variable region and the second heavy chain variable region comprises the amino acid sequence of SEQ ID NO: 4. In some embodiments, the first heavy chain and the second heavy chain comprises the amino acid sequence of SEQ ID NO:

In some embodiments, the first light chain variable region of: a. part a. ii. 1. comprises the amino acid sequence of SEQ ID NO: 44; b. part a. ii. 2. comprises the amino acid sequence of SEQ ID NO: 49; or c. part a. ii. 3. comprises the amino acid sequence of SEQ ID NO: 54.

In some embodiments, the first light chain of: a. part a. ii. 1. comprises the amino acid sequence of SEQ ID NO: 45; b. part a. ii. 2. comprises the amino acid sequence of SEQ ID NO: 50; or c. part a. ii. 3. comprises the amino acid sequence of SEQ ID NO: 55.

In some embodiments, the second light chain variable region of: a. part b. ii. 1. comprises the amino acid sequence of SEQ ID NO: 29; b. part b. ii. 2. comprises the amino acid sequence of SEQ ID NO: 34; or c. part b. ii. 3. comprises the amino acid sequence of SEQ ID NO: 39.

In some embodiments, the second light chain of: a. part b. ii. 1. comprises the amino acid sequence of SEQ ID NO: 30; b. part b. ii. 2. comprises the amino acid sequence of SEQ ID NO: 35; or c. part b. ii. 3. comprises the amino acid sequence of SEQ ID NO: 40.

In some embodiments, the first light chain is a kappa and the second light chain is a lambda. In some embodiments, the first light chain is a lambda and the second light chain is a kappa.

In some embodiments, the bispecific antibody comprises an Fc domain comprising one or more amino acid substitutions that reduce binding to an activating Fc receptor and/or reduce effector function. In some embodiments, the amino acid substitution comprises a L234A and L235A substitution. In some embodiments, the amino acid substitution comprises i) a L234A substitution; ii) a L235A substitution; and iii) a P329A, P329G or P329R substitution.

In some embodiments, the antibody has an IgG isotype. In some embodiments, the antibody is a human antibody.

The disclosure provides a composition comprising any one of the bispecific antibodies of the disclosure.

The disclosure provides a composition comprising a first bispecific antibody comprising: a. a first antigen binding domain that binds to CD3; wherein the first antigen binding domain comprises: i. a first heavy chain variable region having a complementarity determining region 1 (CDRH1) comprising the amino acid sequence of SEQ ID NO: 6; a complementarity determining region 2 (CDRH2) comprising the amino acid sequence of SEQ ID NO: 7; and a complementarity determining region 3 (CDRH3) comprising the amino acid sequence of SEQ ID NO: 8; and ii. a first light chain variable region having: a CDRL1 comprising the amino acid sequence of SEQ ID NO: 11; a CDRL2 comprising the amino acid sequence of SEQ ID NO: 12; and a CDRL3 comprising the amino acid sequence of SEQ ID NO: 13; and b. a second antigen binding domain that binds to GPC3, wherein the second antigen binding domain comprises: i. a second heavy chain variable region having a CDRH1 comprising the amino acid sequence of SEQ ID NO: 6; a CDRH2 comprising the amino acid sequence of SEQ ID NO: 7; and a CDRH3 comprising the amino acid sequence of SEQ ID NO: 8; and ii. second light chain variable region having: 1. a CDRL1 comprising the amino acid sequence of SEQ ID NO: 16; a CDRL2 comprising the amino acid sequence of SEQ ID NO: 17; and a CDRL3 comprising the amino acid sequence of SEQ ID NO: 18; or 2. a CDRL1 comprising the amino acid sequence of SEQ ID NO: 21; a CDRL2 comprising the amino acid sequence of SEQ ID NO: 22; and a CDRL3 comprising the amino acid sequence of SEQ ID NO: 23; and a second bispecific antibody comprising a. a first antigen binding domain that binds to CD28; wherein the first antigen binding domain comprises: i. a first heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and ii. a first light chain variable region having: 1. a CDRL1 comprising the amino acid sequence of SEQ ID NO: 41; a CDRL2 comprising the amino acid sequence of SEQ ID NO: 42; and a CDRL3 comprising the amino acid sequence of SEQ ID NO: 43; or 2. a CDRL1 comprising the amino acid sequence of SEQ ID NO: 46; a CDRL2 comprising the amino acid sequence of SEQ ID NO: 47; and a CDRL3 comprising the amino acid sequence of SEQ ID NO: 48; or 3. a CDRL1 comprising the amino acid sequence of SEQ ID NO: 51; a CDRL2 comprising the amino acid sequence of SEQ ID NO: 52; and a CDRL3 comprising the amino acid sequence of SEQ ID NO: 53; and b. a second antigen binding domain that binds GPC3, wherein the second antigen binding domain comprises: i. a second heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and ii. second light chain variable region having: 1. a CDRL1 comprising the amino acid sequence of SEQ ID NO: 26; a CDRL2 comprising the amino acid sequence of SEQ ID NO: 27; and a CDRL3 comprising the amino acid sequence of SEQ ID NO: 28; or 2. a CDRL1 comprising the amino acid sequence of SEQ ID NO: 31; a CDRL2 comprising the amino acid sequence of SEQ ID NO: 32; and a CDRL3 comprising the amino acid sequence of SEQ ID NO: 33; or 3. a CDRL1 comprising the amino acid sequence of SEQ ID NO: 36; a CDRL2 comprising the amino acid sequence of SEQ ID NO: 37; and a CDRL3 comprising the amino acid sequence of SEQ ID NO: 38.

In some embodiments, the composition enables tumor-specific T cell activation.

The disclosure provides a method of reducing the proliferation of a cancer cell and/or killing a cancer cell comprising contacting the cell with any one of the compositions of the disclosure.

The disclosure provides a method of treating a cancer in a subject comprising administering to the subject any one of the compositions of the disclosure. In some embodiments, the cancer is GPC3 positive.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIGS. 1A, 1B and 1C show a comparison of binding between AD84L3-1/N and ERY974. ERY974, being tested in clinical trials (Clin. Trials Gov. ref NCT05022927) was included as a single agent treatment and used as a clinical reference comparator for activity. hIgG1 is used as an isotype control.

FIGS. 3A-3D are a series of graphs showing T-cell retargeted killing/lysis of the GPC3 positive Hep G2 cells (FIG. 3A and FIG. 3B) and the GPC3 negative SK-HEP-1 (FIGS. 3C and 3D) cells by one of the GPC3×CD28 bispecific antibodies of the invention (AI3P44/N) when combined with the GPC3×CD3 bsAb of the invention (AD84L3-1/N). The concentration (dose) dependent lysis of tumor cells by AD84L3-1/N alone and by combinations of AD84L3-1/N with different fixed concentrations (0.5; 0.1; 0.05 or 0.025 µg/mL) of AI3P44/N is shown. Effector cells are PBMCs derived from two different healthy donors (FIGS. 3A and 3C: donor 1, and FIGS. 3B and 3D: donor 2). CD28 bsAbs synergize with GPC3×CD3 to kill GPC3-positive Hep G2 cells. Killing is dose-dependent regarding the concentration of the GPC3×CD28 bsAb. No killing is induced using the GPC3 negative SK-HEP-1 cell line. Y4L3-1/N is an untargeted CD3 monovalent antibody and is used as a negative control; hIgG1 is used as an isotype control. ERY974 single treatment is used as a reference comparator.

FIGS. 4A-4C are a series of graphs showing T-cell retargeted killing/lysis of the GPC3 positive Hep G2 cell line (FIGS. 4A, 4B, and 4C). Dose response of the GPC3×CD3 bispecific antibody AD84L3-1/N when combined with fixed doses (0.5; 0.1 or 0.05 µg/mL) of GPC3×CD28 bsAbs of the invention, either AI3P44/N (FIG. 4A), AI3P30/N (FIG. 4B) or AI3P111 (FIG. 4C). The GPC3 arms P44 and P30 are targeting membrane distal regions within GPC3 and, as such, are not competing with the membrane proximal GPC3 arm of the GPC3×CD3 bsAb (e.g. AD84). The P111 GPC3 arm is binding membrane proximal but is also not competing with the GPC3 arm of the CD3 bsAb (e.g. AD84) for binding to GPC3. Synergy for all combination of GPC3×CD3 bsAb and GPC3×CD28 bsAbs in killing GPC3-positive Hep G2 target cells is observed. Killing is dose-dependent regarding the concentration of the GPC3×CD28 bsAb. Comparative TDCC data show that pairing the P111 arm to AI3 is less efficient in boosting AD84L3-1/N activity compared to AI3P44/N combination (FIG. 4A and FIG. 4C, respectively). Y4L3-1/N is an CD3 only targeting monovalent antibody which does not bridge tumor cells and T-cells and thus is used as a negative control; hIgG1 is used as an isotype control. ERY974single treatment is used as a clinical reference comparator for activity. Data are presented using a representative PBMC donor in each condition. For more explanation, see text.

(AD84L3-1/N) alone in this cell line with lower GPC3-expression, i.e. Hep 3B, 60'000 GPC3/cell. Strong, synergistic killing effect of the combination of the CD3 and CD28 bsAb in killing of GPC3-positive target cells. Killing can be tuned by changing the concentration of the GPC3×CD28 bsAb. As negative controls, Y4L3-1/N (CD3-only targeting monovalent antibody) alone and in combination with the GPC3×CD28 bsAbs of the present invention are used; hIgG1 is used as an isotype control. ERY974 single treatment is used as a clinical reference comparator for activity.

Figure 7A:
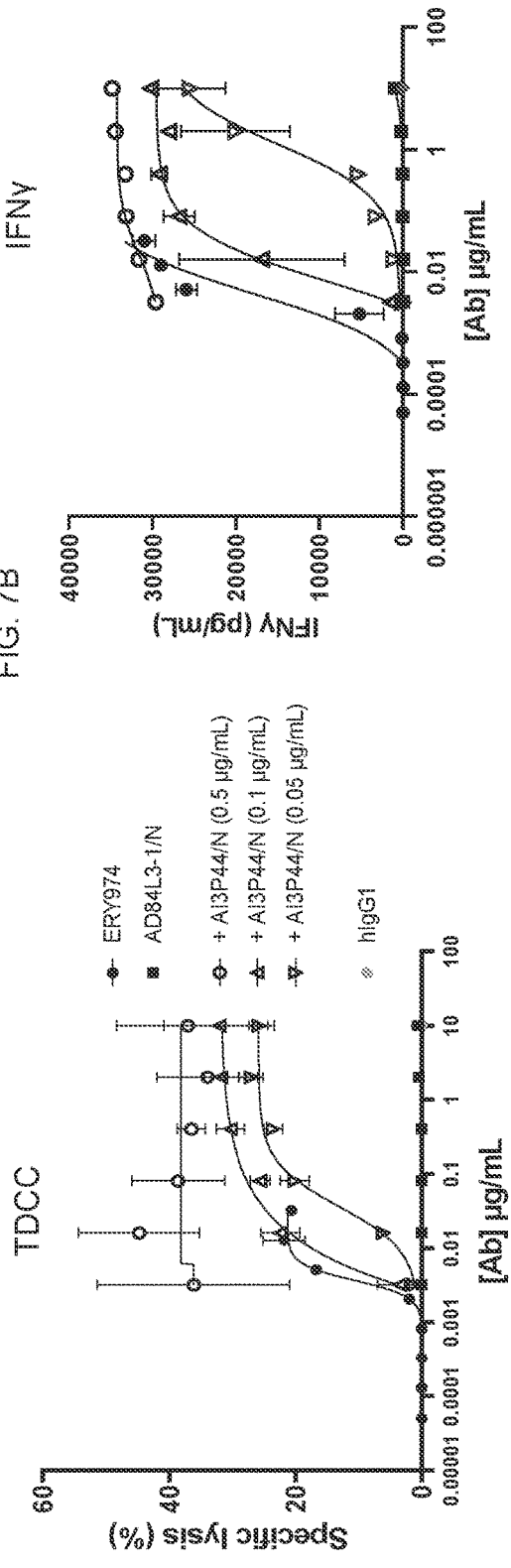
Figure 7B:
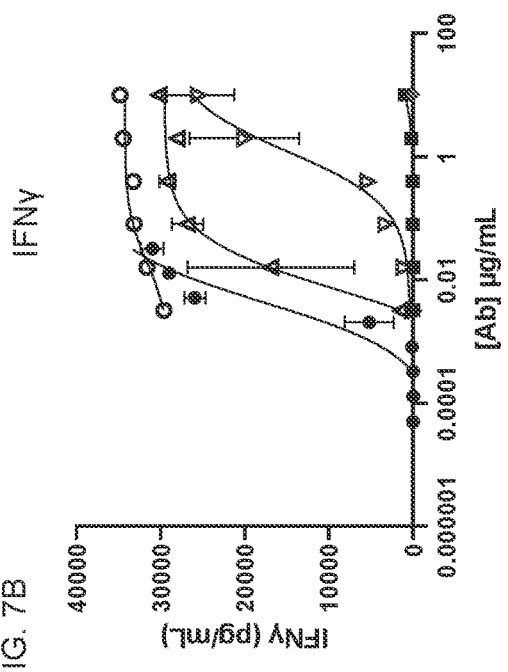
Figure 7C:
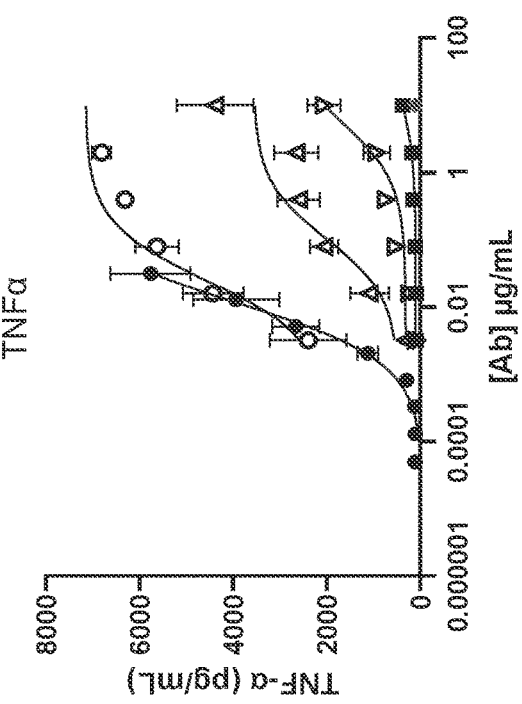
Figure 7D:
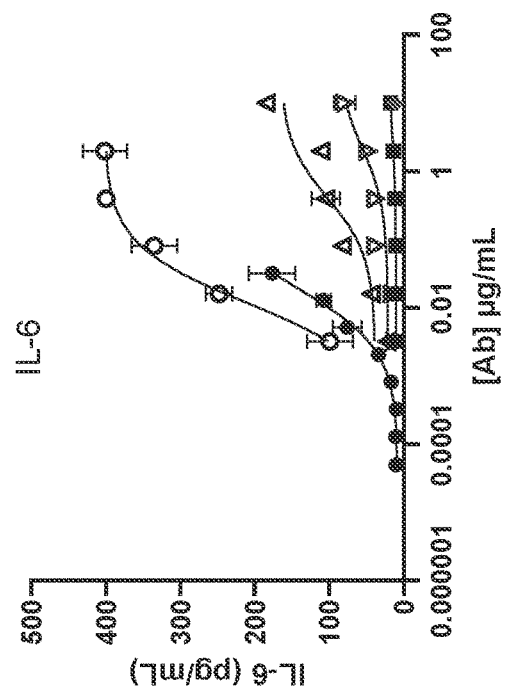

FIGS. 7A-7D are a series of graphs showing T-cell retargeted killing/lysis and simultaneous measurement of secretion of proinflammatory cytokines. T-cell retargeted killing/lysis of the GPC3-expressing cell line Hep G2 (700'000 GPC3/cell) by one of the GPC3×CD28 bispecific antibodies of the invention (AI3P44/N) combined with the GPC3×CD3 bsAb (AD84L3-1/N) (FIG. 7A). Secretion of IFN-γ, IL-6 and TNF-α are shown in FIGS. 7B, 7C and 7D, respectively. Combination of CD3 and CD28 bsAbs leads to stronger induction of secretion of proinflammatory cytokines compared to GPC3×CD3 monotherapy using AD84L3-1/N. Cytokine levels depending on the concentration of the CD28 bsAb (AI3P44/N). ERY974, used as clinical comparator, shows strong induction of cytokines at a level mostly above the one observed with the highest concentration of AD84L3-1/N in combination with 0.05 or 0.1 µg/mL AI3P44/N. hIgG1 is used as an isotype control. ERY974 single treatment is used as a clinical reference comparator.

Figure 8A:
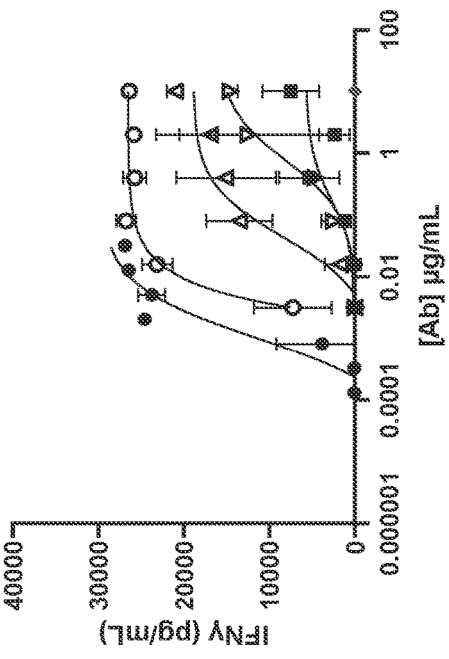
Figure 8B:
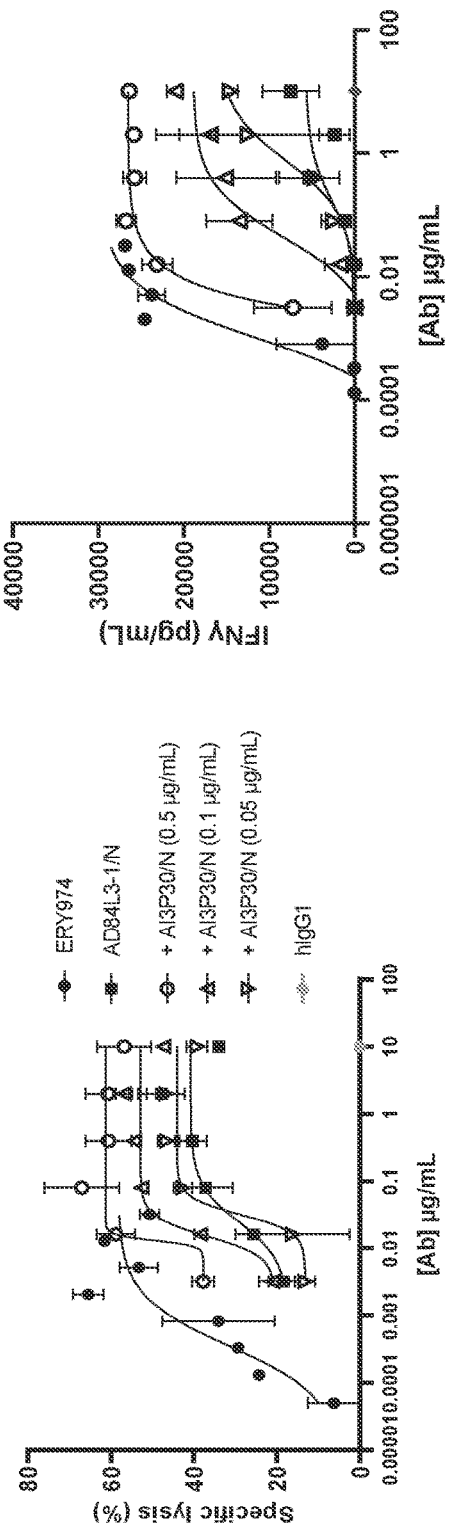
Figure 8C:
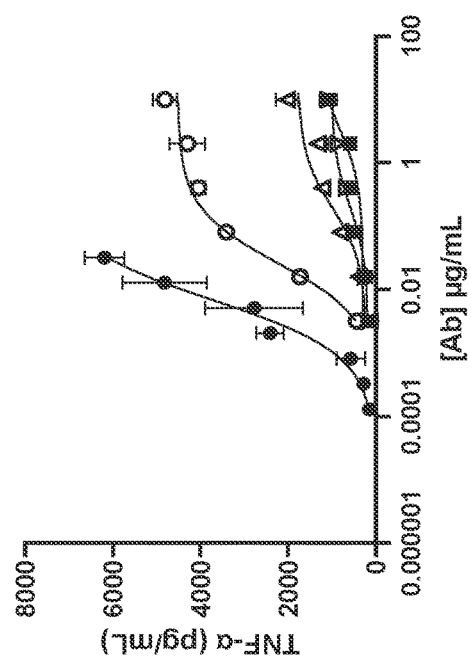
Figure 8D:
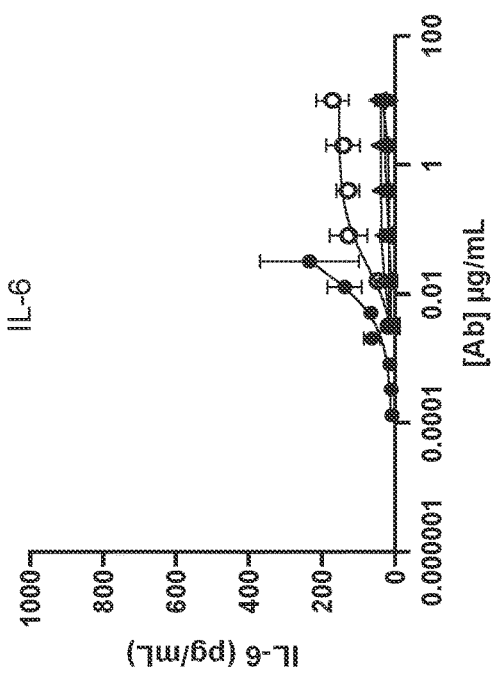

FIGS. 8A-8D are a series of graphs showing T-cell retargeted killing/lysis and secretion of proinflammatory cytokine using AI3P30/N instead of AI3P44/N, results with the latter depicted in FIG. 7. T-cell retargeted killing/lysis and simultaneous measurement of secretion of proinflammatory cytokines. T-cell retargeted killing/lysis of the GPC3-expressing cell line Hep G2 by one of the GPC3×CD28 bispecific antibodies of the invention (AI3P30/N) combined with the GPC3×CD3 bsAb (AD84L3-1/N) (FIG. 8A). Secretion of IFN-γ, IL-6 and TNF-α, are shown in FIGS. 8B, 8C and 8D, respectively. Combination of CD3 and CD28 bsAbs leads to stronger induction of secretion of proinflammatory cytokines compared to GPC3×CD3 monotherapy using AD84L3-1/N. Cytokine levels depending on the concentration of the CD28 bsAb (AI3P30/N). ERY974, used as clinical comparator, shows strong induction of cytokines at a level mostly above the one observed with the highest concentration of AD84L3-1/N in combination with 0.05 or 0.1 µg/mL AI3P30/N. hIgG1 is used as an isotype control. ERY974 single treatment is used as a clinical reference comparator.

Figure 9B:
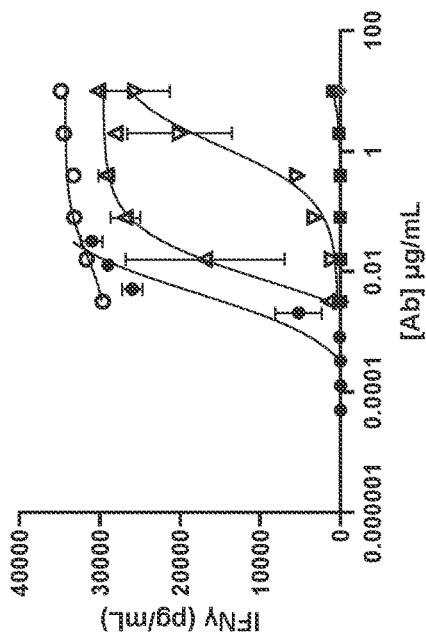
Figure 9A:
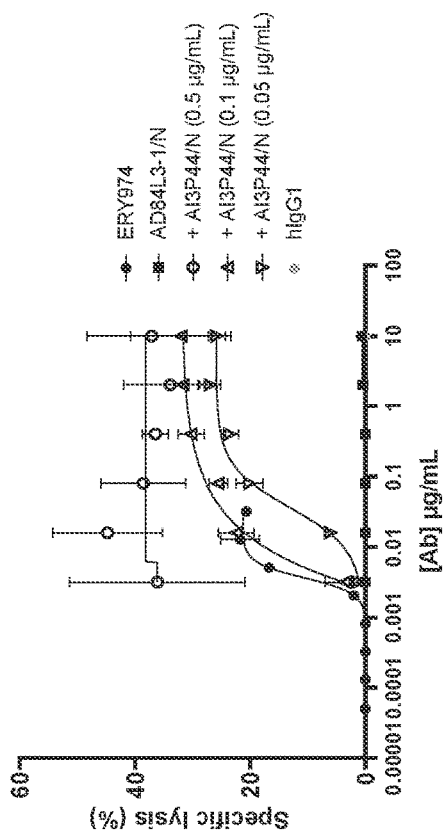
Figure 9D:
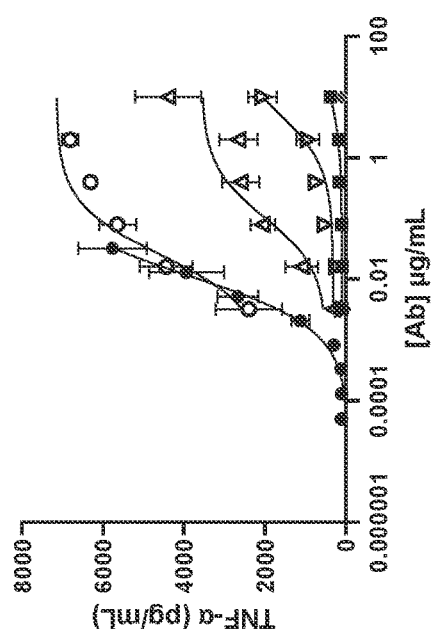
Figure 9C:
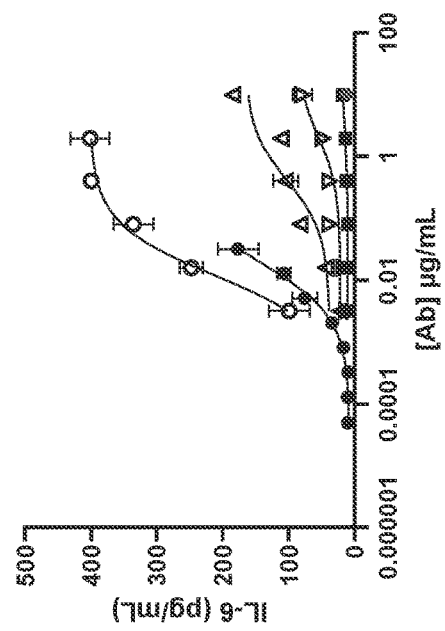
Figure 9F:
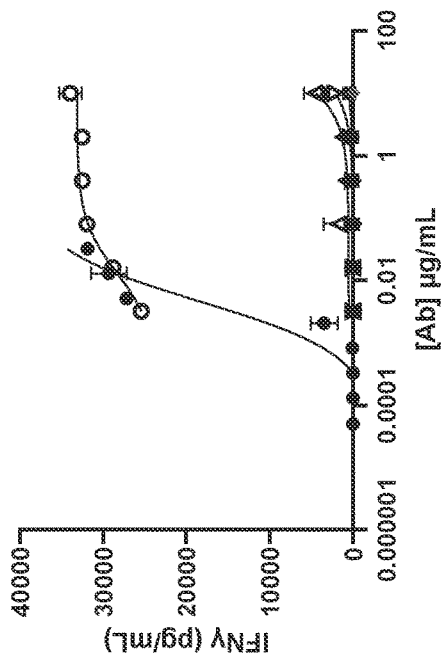
Figure 9H:
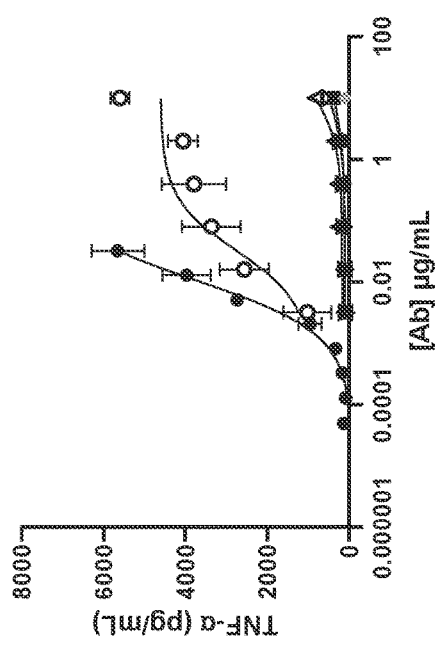
Figure 9E:
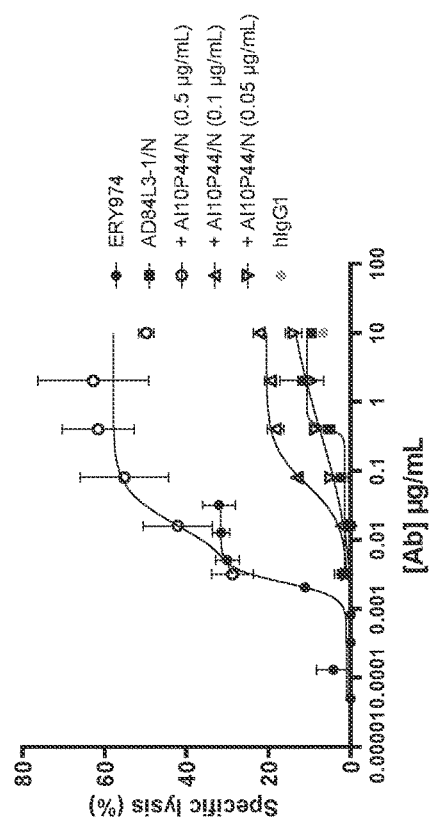
Figure 9G:
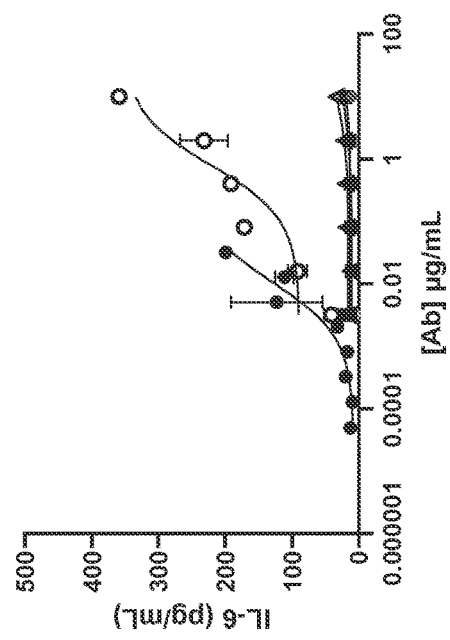

FIGS. 9A-9H are a series of graphs showing T-cell retargeted killing/lysis and secretion of proinflammatory cytokines comparing AI3P44/N (FIGS. 9A-9D) and AI10P44/N (FIGS. 9E-9H). AI10 has a lower binding affinity to CD28 than AI3. The same PBMC donor is used as a source of effector cells for each experiment for comparability purposes. The GPC3-expressing cell line Hep G2 is used as target. T-cell retargeted killing activities are depicted for AI3P44/N (FIG. 9A) and AI10P44/N (FIG. 9E) combination. Secretion of IFN-γ (FIGS. 9B and 9F); IL-6 (FIGS. 9C and 9G); TNF-α (FIGS. 9D and 9H). A higher killing rate is achieved compared with ERY974 at 0.5 µg/mL with concomitant similar or lower cytokine release. Cytokine release can be reduced lowering concentrations of GPC3×CD28, particularly in case of AI10P44/N. At 0.1 µg/mL, killing by AI3P44/N is similar to ERY974 (FIG. 9A) with concomitantly lower cytokine release (FIGS. 9B-9D). AI10P44/N is also fostering killing at 0.1 µg/mL, but with an overall killing level below the one achieved by ERY974 (FIG. 9E). Resulting cytokine release is low (F-H, IFN-γ<5000 pg/mL, IL-6<50 pg/mL, TNF-α<100 pg/mL) despite of maintenance of some killing activity (E, up to 20-25% max killing activity when AI10P44/N is added at 0.1 µg/mL). hIgG1 is used as an isotype control. ERY974 single treatment is used as a clinical reference comparator.

FIGS. 10A-10F are a series of graphs showing T-cell retargeted killing/lysis using the CellTiter-Glo readout. As target cells, three GPC3-expressing cell lines are used, Hep G2 (FIGS. 10A-10B, two PBMC donors are shown), Hep 3B (FIGS. 10C-10D, two PBMC donors are shown) and HuH-7 (FIGS. 10E-10F, two PBMC donors are shown) by the GPC3×CD3 bsAb (AD84L3-1/N) in combination with the GPC3×CD28 bispecific antibodies of the invention (AI3P44/N). No or only minimal killing by the GPC3×CD3 (AD84L3-1/N) alone in Hep 3B (60'000 GPC3/cell) or HuH-7 (18'000 GPC3/cell). Synergistic killing effect of the combination of the CD3 and CD28 bsAb in killing all GPC3-positive target cells, regardless of their target expression level. As negative controls, Y4L3-1/N (CD3-only targeting monovalent antibody) alone and in combination with the GPC3×CD28 bsAbs of the present invention are used; hIgG1 is used as an isotype control. ERY974 single treatment is used as a clinical reference comparator.

DETAILED DESCRIPTION OF THE INVENTION

The invention comprises GPC3×CD3 bispecific antibodies, GPC3×CD28 bispecific antibodies, and compositions comprising combinations of GPC3×CD3 bispecific antibodies with GPC3×CD28 bispecific antibodies, in order to induce T cell activation and killing of glypican-3 (GPC3) positive tumor cells. Specifically, the invention is based in part on the combination of two bispecific antibodies, one for the co-engagement of a GPC3 expressed at the surface of the target (e.g. tumor cell) cells to trigger CD3 positive T cell activation, and another bispecific antibody for the co-engagement of GPC3 (expressed on a tumor cell) with CD28 (expressed on a T cell). This results in clustering and therefore, boosting of tumor-specific T-cell activation.

The present invention provides fully human GPC3×CD3 bispecific antibodies, which are designed such that it can be administered in parallel with GPC3×CD28 bispecific antibodies of the invention. Importantly, there is no binding competition to the target GPC3 between the GPC3×CD3 bispecific antibodies and the GPC3×CD28 bispecific antibodies. This invention provides agonist CD28 antigen binding molecules which enable the co-engagement of the T cell with a GPC3 receptor on a tumor cell. This invention also provides a GPC3×CD3 bispecific antibody which mediates tumor-specific T cell activation (i.e., signal 1) and which when administered in combination with a GPC3×CD28 bispecific antibody of the invention, mediates increased tumor-specific T cell activation (signal 2). GPC3×CD28 bispecific antibodies of this invention are the first GPC3× CD28 antibodies described in literature, providing a novel therapeutic option for GPC3+ solid tumor patients. Furthermore, the combination of a GPC3×CD3 bispecific antibody with a GPC3×CD28 bispecific antibody of the invention is a novel mechanism for activating the immune system by targeting costimulatory signals on T cells.

Glypican-3 (GPC3)

Glypican-3 (GPC3) is a heparan sulfate proteoglycan (HSPG). There are six glypican subtypes, namely, GPC 1-6, with similar structures consisting of a 60-70 kDa protein connected to the cell membrane by a glycosylphosphatidylinositol (GPI) anchor, 14 conserved cysteine residues, and the last 50 residues at the carboxyl end modified by the heparan sulfate (HS) side-chain. GPC3 has been implicated in cell growth, differentiation, and migration (Glypicans as Cancer Therapeutic Targets. Li N. at al Trends Cancer. 2019 Nov. 1; The Role of Glypicans in Cancer Progression and Therapy. Li N et al. J Histochem Cytochem. 2020 December; 68(12): 841-862). GPC3 is a highly tumor-specific antigen expressed during fetal development but physiologically structurally suppressed in adult tissues. Aberrant expression of GPC3 has been reported in hepatocellular carcinoma (HCC), lung squamous cell carcinoma (LSCC), testicular tumors, ovarian yolk sac tumors, melanoma, ovarian clear cell carcinoma and other cancers (Glypican-3 induces a mesenchymal to epithelial transition in human breast cancer cells Fedra Castillo L. et al, Oncotarget. 2016 Sep. 13; 7(37): 60133-60154; GPC-3 in hepatocellular carcinoma: current perspectives. Wu Y et al. J Hepatocell Carcinoma. 2016; 3: 63-67). GPC3 expression is correlated with poor prognosis in HCC patients (Prognostic and clinicopathological significance of glypican-3 overexpression in hepatocellular carcinoma: A meta-analysis. Li J. et al World J Gastroenterol. 2014 May 28; 20(20): 6336-6344). Thus, GPC3 is a biomarker and prognostic factor of HCC, and an attractive immunotherapeutical target (Cancer immunotherapy-targeted glypican-3 or neoantigens. Shimizu Y. et al. Cancer Sci. 2018 March; 109(3): 531-541; Next-Generation Cancer Immunotherapy Targeting Glypican-3. Shimizu Y et al. Front Oncol. 2019; 9: 248).

CAR T cell therapies show clinical benefit in hematologic malignancies, although efficacy in solid tumors is limited. Monoclonal antibodies targeting GPC3 have entered clinical testing, exemplified by Codrituzumab (GC33, RO5137382, ClinicalTrials.gov NCT04928677), with low rates of responses. Bispecific antibodies with a potentially higher activity are exemplified by "ERY974" as described in WO2017/159287A1 (incorporated by reference in its entirety) comprising as CDRs the CDRs as shown in SEQ ID NOS: 42 to 45 of WO2017/159287A1.

ERY974 is a T cell redirecting, humanized IgG antibody with a common light chain, which can bind to both GPC3 and CD3, promoting cytotoxicity through the action of T cell effectors. The GPC3 binder used in ERY974 is a humanized, affinity matured, and stability-engineered version derived from the hGC33 antibody (An anti-glypican 3/CD3 bispecific T cell-redirecting antibody for treatment of solid tumors. Ishiguro T. et al., Sci Transl Med. 2017 Oct. 4; 9(410); Engineering a bispecific antibody with a common light chain: Identification and optimization of an anti-CD3 epsilon and anti-GPC3 bispecific antibody, ERY974. Shiraiwa et al., Methods, 2018). The CD3 binder used in ERY974, rCE115, was derived from a rat immunization, it was humanized by the CDR grafting method (Results of a phase 1 dose escalation study of ERY974, an anti-glypican 3 (GPC3)/CD3 bispecific antibody, in patients with advanced solid tumors. Safran et al. Cancer Res (2021) 81 (13_Supplement): CT111). The binding arm is specific for CD3ε. Lead antibodies against GPC3 and CD3& were multidimensionally optimized to generate ERY974 using a hIgG4 backbone to reduce Fc effector functions. ERY22 is a lead bispecific antibody consisting of two kinds of H chains and two kinds of L chain. ERY22 was humanized, and a common L chain was identified to create humanized ERY (hERY) with a common L chain. hERY was further engineered to improve its binding affinity to the antigens and also its physicochemical properties, such as enhancing the stability, leading to ERY974 (Engineering a bispecific antibody with a common light chain: Identification and optimization of an anti-CD3 epsilon and anti-GPC3 bispecific antibody, ERY974. Shiraiwa et al., Methods, 2018).

ERY974 showed significant antitumor effects in preclinical tumor models that were unresponsive to treatment with immune checkpoint inhibitors (such as PD-1 and CTLA-4) (An anti-glypican 3/CD3 bispecific T cell-redirecting antibody for treatment of solid tumors. Ishiguro T. et al., Sci Transl Med. 2017 Oct. 4; 9(410)). Further investigation showed that ERY974 induced a high degree of inflammation in the tumor microenvironment, with toxicology studies in cynomolgus monkeys showing raised levels of cytokines in the short-term (An anti-glypican 3/CD3 bispecific T cell-redirecting antibody for treatment of solid tumors. Ishiguro T. et al., Sci Transl Med. 2017 Oct. 4; 9(410)). A significant improvement in antitumor activity in xenografts is achieved using a combination of ERY974 and chemotherapy (An anti-glypican 3/CD3 bispecific T cell-redirecting antibody for treatment of solid tumors. Ishiguro T. et al., Sci Transl Med. 2017 Oct. 4; 9(410)). Early results of a first phase I clinical trial of ERY974 (ClinicalTrials.gov NCT05022927) in solid tumors were presented at the annual meeting of the American Association for Cancer Research (AACR) in 2021 (Results of a phase 1 dose escalation study of ERY974, an anti-glypican 3 (GPC3)/CD3 bispecific antibody, in patients with advanced solid tumors. Safran et al. Cancer Res (2021) 81 (13_Supplement): CT111). To mitigate for the toxicity of cytokine release syndrome (CRS), steroid prophylaxis and a two-step intra-patient escalation were implemented. 29 patients were enrolled in very low dose levels ranging from 0.003 µg/kg to 0.81 µg/kg. Dose limiting toxicities in terms of CRS (grade 2 and 3) were found at the 0.12/0.81 µg/kg dosing schedule (Results of a phase 1 dose escalation study of ERY974, an anti-glypican 3 (GPC3)/CD3 bispecific antibody, in patients with advanced solid tumors. Safran et al. Cancer Res (2021) 81 (13_Supplement): CT111). Increased IL-6, TNF-α and IL-8 were observed in patients, explaining the appearance of the CRS. Tolerated doses of ERY974 were low. With a preclinically determined steep dose response curve, clinical dosing will likely be complicated due to the small therapeutic window, with concomitantly low probability for inducing responses.

Different GPC3×CD3 bsAb formats are in preclinical development (A novel targeted GPC3/CD3 bispecific antibody for the treatment hepatocellular carcinoma. Yu L. et al. Cancer Biol Ther. 2020; 21(7): 597-603; Development of a Tetravalent T-Cell Engaging Bispecific Antibody Against Glypican-3 for Hepatocellular Carcinoma. Yu L. et al., J Immunother. 2021 Apr. 1; 44(3):106-113; Combination Therapy of Hepatocellular Carcinoma by GPC3-Targeted Bispecific Antibody and Irinotecan is Potent in Suppressing Tumor Growth in Mice. Chen X. et al. Mol Cancer Ther. 2022 January; 21(1): 149-158). One of them is a ScFv of an anti-human CD3 antibody and VH domain of an anti-GPC3 antibody derived from the monoclonal antibodies L2K and HN3, respectively. The ScFv fragment, linked by 15 amino-acid long poly-glycine/serine linker consisting of (G4 S)3, was fused to the Fc of IgG1 via the hinge region. Analogously, the C-terminus of VH domain was fused to Fc domain. The regions of each Fc introduced P329G/L234A/L235A mutations (to suppress Fc-mediated activity), and knob-in-hole mutations for production issues. Preclinical data show in vitro and in vivo tumoricidal activity (A novel targeted GPC3/CD3 bispecific antibody for the treatment hepatocellular carcinoma. Yu L. et al. Cancer Biol Ther. 2020; 21(7): 597-603). Highly engineered bsAb formats are supposed to generate anti-drug-antibodies (ADA) with concomitant risk for loss of exposure. No clinical trials have been reported so far.

CD28 is a key co-stimulatory receptor expressed at the surface of T-cells. It belongs to a subfamily of costimulatory molecules characterized by an extracellular variable immunoglobulin-like domain also comprising CTLA-4, ICOS, PD-1 and BTLA. CD28 is expressed at the cell surface of T-cells as a disulfide-linked homodimer and is found on approximately 80% of human CD4+ T cells and 50% of CD8+ T cells (Mir, M. A. (2015). Introduction to Costimulation and Costimulatory Molecules. In Developing Costimulatory Molecules for Immunotherapy of Diseases, (Elsevier), pp. 1-43).

Despite lacking intrinsic enzymatic activity, CD28 engagement by its ligands leads to specific phosphorylation and transcriptional signaling which results in metabolic changes and in the production of key cytokines, chemokines, and survival signals essential for long-term expansion and differentiation of T cells.

The primary ligands for CD28 are CD80 (B7.1) and CD86 (B7.2), which are mainly expressed at the surface of professional antigen presenting cells (APC). CD80 and CD86 diverge in their expression patterns, multimeric states, and functionality. Because CD28 and CTLA-4 are highly homologous, they compete for the same ligands. However, as CTLA-4 binds these ligands with a higher affinity than CD28, CTLA-4 competes with CD28 for ligands and ultimately suppresses T cells responses.

Several anti-CD28 monoclonal antibodies have been developed. Some of these, termed superagonist (SA) antibodies, was found to induce the full activation of primary resting T cells even in the absence of TCR ligation (the so-called "signal 1"). The first-in-human study of one of such SA anti-CD28 antibodies, TGN1412, resulted in severe inflammatory reactions including a cytokine storm unexpected in previous in vitro and in vivo studies, resulting in a chronic organ failure in all healthy volunteers undergoing TGN1412 application.

Targeted Costimulation of CD28 Using Bispecific Antibodies

To avoid the safety issues linked to superagonist antibodies or systemic CD28 co-stimulation, tumor targeted CD28 bispecific antibodies can be designed to limit co-stimulation of T cells within the vicinity of tumor cells. By pairing an agonist anti-CD28 arm to an anti-tumor associated antigen (TAA) arm, molecules capable of bridging T cells to malignant cells expressing the selected TAA are generated. Because CD28 bispecific antibodies can only bind to CD28 monovalently, CD28 cannot be accidentally clustered in the absence of TAA-positive target cells, thus preventing systemic T cell activation. Even in presence of TAA-positive cancer cells, which allow for CD28 clustering at the surface of the T cells, the full cytotoxic potential of T cells can only be unleashed in presence of primary T cell stimulation via the TCR. This contrasts with the bivalent super-agonist CD28 monoclonal antibodies described above.

As above, results of first clinical trials with T-cell bispecific antibodies TAA×CD3 in patients with advanced solid tumors were not efficacious. Preclinical studies for the treatment of solid tumors have shown the benefit of adding costimulatory CD28 bispecific antibodies (providing additional T cell activation, i.e. ("signal 2")) boosting efficacy of CD3 bispecific antibodies (which are triggering T cell activation, i.e. ("signal 1")) (Skokos, D., Waite, J. C., Haber, L., Crawford, A., Hermann, A., Ullman, E., Slim, R., Godin, S., Ajithdoss, D., Ye, X., et al. (2020). A class of costimulatory CD28-bispecific antibodies that enhance the antitumor activity of CD3-bispecific antibodies. Sci. Transl. Med. 12, eaaw7888), or PD-(L)1 checkpoint inhibitors (Waite, J. C., Wang, B., Haber, L., Hermann, A., Ullman, E., Ye, X., Dudgeon, D., Slim, R., Ajithdoss, D. K., Godin, S. J., et al. (2020). Tumor-targeted CD28 bispecific antibodies enhance the antitumor efficacy of PD-1 immunotherapy. Sci. Transl. Med. 12, eaba2325). Examples of agonist TAA×CD28 bispecific antibodies are described in WO2019246514, WO2020198009, WO2020132066, WO2020132024, WO2020127618, WO2021259890 and WO2021155071, each of which are incorporated by reference in their entirety. Some corresponding molecules currently being tested in clinical trials (ClinicalTrials.gov Identifiers: NCT04590326, NCT03972657, NCT04626635). To date, such conditional CD28 co-stimulation for T cell activation has never been applied for GPC3 positive malignancies, and has never been combined with GPC3×CD3 bispecific antibodies to mediate cell-mediated tumoricidal activity and to fine-tune related cytokine release. Another way to provide T cell activation signal 2, in the context of GPC3 positive malignancies has been developed by Pieris pharmaceuticals with the objective to elicit 4-1BB costimulatory effects in a tumor localized manner. PRS-342 is a 4-1BB/GPC3 preclinical immuno-oncology engineered Anticalin-antibody bispecific fusion protein and results have been published at AACR 2019 (Costimulatory T-cell engagement by PRS-342, a GPC3/4-1BB bispecific molecule, leads to activation of T-cells and tumor growth inhibition in a HCC humanized mouse model. Bossenmeier et al Cancer Res (2019) 79 (13_Supplement): 3268) showing potent T-cell activation strictly dependent on the presence of GPC3-positive tumor cells. No clinical trials are reported thus far.

The present invention provides a new fully human GPC3×CD3 bispecific antibody designed to be administered in parallel with the GPC3×CD28 bispecific antibodies also provided by this invention. The GPC3×CD3 and the GPC3×CD28 bispecific antibodies of the invention are not cross-reactive for GPC3 binding, i.e., they do not compete for binding to GPC3. This invention provides agonist CD28 antigen binding molecules which enable co-engagement with GPC3 on tumor cells. The combination of these GPC3×CD28 and GPC3×CD3 bispecific antibodies mediates strong tumor-specific T cell activation.

The present invention describes a novel GPC3×CD3 bispecific antibody and novel GPC3×CD28 bispecific antibodies, and their combination. The comparator molecule, "ERY974", clinically showed CRS already at low doses, which in turn hampers potential therapeutic activity. The GPC3×CD3 bispecific antibody of this invention can be dosed at higher levels with lower overall levels of cytokine release compared with ERY974, which is advantageous for therapeutic use. Specifically, the combination enables dosing schedules such as like parallel treatment or sequential treatments, which likely will allow to better control of dose-limiting CRS and concomitant increase in activity. Generally, the strongest cytokine release is usually seen at the first dose of a TAA×CD3 and much lower release at the following doses. To avoid this problem, in the instant invention, beginning a therapy with the GPC3×CD3 and following with a treatment with the combination of the GPC3×CD3 bispecific antibody and a GPC3×CD28 bispecific antibody offers a way to mitigate cytokine release and to achieve improved efficacy compared to GPC3×CD3 monotherapy. Activity of GPC3×CD28 in the combination can further be fine tuned using the panel of different molecules presented in this invention, which is advantageous for therapeutic applications.

Exemplary GPC3×CD3 and GPC3×CD28 Bispecific Antibodies

The GPC3×CD3 bispecific antibody (further named also as "bispecific antibody GPC3×CD3" or "GPC3×CD3 bispecific antibody") comprise first a part specifically binding to human GPC3, and a second binding part specifically binding human CD38. For the GPC3×CD3 bispecific antibodies, the letter-number combination "AD84" or "AD95" denotes the anti-GPC3 antibody arm, and "L3-1" (also called "1A4") denotes the anti-CD3 antibody arm, of the bispecific antibody of this invention.

The GPC3×CD28 bispecific antibody comprises a first binding part (i.e. antigen binding region), specifically binding to human CD28 and a second a binding part (i.e. antigen binding region) specifically binding human GPC3 (noncompetitive binding domain compared with the GPC3×CD3 bispecific antibody). For GPC3×CD28 bispecific antibodies, "P44", "P30" and "P111" denote the anti-GPC3 antibody arm, and "AI3" or "A110" the anti-CD28 antibody arms of the bispecific antibodies of this invention.

The structure of the κλ bispecific antibodies (KA-bodies) of this invention is almost indistinguishable from the structure of a native IgG. The present invention provides a combination of low immunogenicity with high efficacy. GCP3×CD3 bispecific antibody comprise a common heavy chain, and in one embodiment a kappa light chain in the GPC3 binding part and a lambda light chain in the CD3 binding part. The GPC3×CD28 bispecific antibody comprises a different common heavy chain and in one embodiment a kappa light chain in the GPC3 binding part and a lambda light chain in the CD28 binding part. The GPC3 binding arms of the GPC3×CD3 and of the GPC3×CD28 bispecific antibodies of the invention target different domains within GPC3 to avoid binding competition on target cells.

The GPC3×CD3 and the GPC3×CD28 bispecific antibodies of the invention require a Fc portion with drastically reduced binding to FcγR to avoid Fc-mediated effector functions, or Fc receptor-mediated cross-linking of the bispecific antibodies.

In some embodiments, the heavy chains are native heavy chains (i.e, does not contain any mutations ("wildtype")). In some embodiments, the heavy chains comprise at least one mutation (i.e, with "LALA" mutation or "LALAPA" mutation). In some embodiments, the bispecific antibodies comprises in each subunit of the Fc domain amino acid substitutions that reduce binding to an activating Fc receptor and/or reduce effector function wherein said amino acid substitutions are L234A and L235A and/or a substitution of P329, selected from the group consisting of P329A, P329G and P329R (Kabat EU index numbering). In one embodiment, the bispecific antibody comprises in each subunit of the Fc domain amino acid substitutions L234A and L235A and P329A (Kabat EU index numbering). L234A and L235A (LALA) denote that the amino acid leucine at position 234/235 is replaced by alanine. P329A (PA) denotes that the amino acid proline at position 329 is replaced by alanine. "/N" in a bispecific antibody, indicate that the Fc portion carries the mutations L234A and L235A and P329A (LALAPA).

The bsAbs of the invention can be based on any of the different antibody formats that have been previously described. In general, IgG-like formats are preferred as they provide favorable properties such as long half-life and potentially reduced immunogenicity, but any other molecular bispecific format can also be used for the invention. In some embodiments, the bispecific antibodies share a common heavy chain. The concept of using a common heavy chain for obtaining bispecific antibodies has been previously described (Exploiting light chains for the scalable generation and platform purification of native human bispecific IgG. Fischer N. et al. Nat Commun. 2015 Feb. 12; 6:6113; Optimizing assembly and production of native bispecific antibodies by codon de-optimization. Magistrelli G, MAbs. 2017 February/March; 9(2):231-239). Kappa lambda bispecific antibodies are described in e.g. WO2014087248 (hereby incorporated by reference in its entirety).

Optionally, the bispecific antibodies have light chains of different types. For example, one light chain is a kappa light and the other light chain is a lambda light chain (i.e., kl-body) Differing light chains allows the bispecific to be purified easily using kappa and lambda select resins.

Additionally, bispecific antibodies of the invention can be made using the techniques, including those disclosed in WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions.

However, it is also possible to obtain bispecific antibodies of the invention by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGKA antibodies or "KA bodies," a new fully human bispecific IgG format. This KA-body format allows the affinity purification of a bispecific antibody that is undistinguishable from a standard IgG molecule with characteristics that are undistinguishable from a standard monoclonal antibody and, therefore, favorable as compared to previous formats.

In addition to methods described above, bispecific antibodies of the invention can be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange.

Antibodies of the present invention have two or more antigen binding domains and are bispecific. Bispecific antibodies of the invention include antibodies having a full-length antibody structure or partial length antibody structure such as Fab "Full length antibody" as used herein refers to an antibody having two full length antibody heavy chains and two full length antibody light chains. A full-length antibody heavy chain (HC) consists of well known heavy chain variable and constant domains VH, CH1, CH2, and CH3. A full-length antibody light chain (LC) consists of well-known light chain variable and constant domains VL and CL. The full-length antibody may be lacking the C-terminal lysine (K) in either one or both heavy chains.

The term "Fab-arm" or "half molecule" refers to one heavy chain-light chain pair that specifically binds an antigen.

Full length bispecific antibodies of the invention may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

Exemplary CD28, CEA and MSLN antibodies that may be used to engineer bispecific molecules include the antibodies disclosed herein. Exemplary anti-GPC3 antibodies from which the GPC3 antigen binding region can be derived from include the "AD843" or "AD95" antibody. Exemplary anti-GPC3 antibodies from which the GPC3 antigen binding region can be derived from include the "P44", "P30" or "P111" antibody. Exemplary anti-CD28 antibodies from which the CD28 antigen binding region can be derived from include the "AI3", "AI10" or "AI13" antibody. Exemplary anti-CD3 antibodies from which the CD3 antigen binding region can be derived from include the "L3-1" (also called "1A4") antibody. Table 1 shows the amino acid sequences of the regions of the antibodies of the disclosure.

TABLE 1

Exemplary Amino Acid Sequences of the Disclosure

| SEQ ID NO: | Name | Amino Acid Sequence |
|---|---|---|
| SEQ ID NO: 1 | Common heavy chain CDR-H1 of GPC3xCD28 bispecific antibodies | GFTFSSYA |
| SEQ ID NO: 2 | Common heavy chain CDR-H2 of GPC3xCD28 bispecific antibodies | ISGSGGST |

TABLE 1-continued

Exemplary Amino Acid Sequences of the Disclosure

| SEQ ID NO: | Name | Amino Acid Sequence |
|---|---|---|
| SEQ ID NO: 3 | Common heavy chain CDR-H3 of GPC3xCD28 bispecific antibodies | AKSYGAFDY |
| SEQ ID NO: 4 | Common heavy chain VH of GPC3xCD28 bispecific antibodies | EVQLLESGGGLVQPGGSLRLSCAASGFTFSSYAMSWVRQA PGKGLEWVSAISGSGGSTYYADSVKGRFTISRDNSKNTLY LQMNSLRAEDTAVYYCAKSYGAFDYWGQGTLVTVSS |
| SEQ ID NO: 5 | Common heavy chain HC (LALA + P329A mutations) of GPC3xCD28 bispecific antibodies | EVQLLESGGGLVQPGGSLRLSCAASGFTFSSYAMSWVRQA PGKGLEWVSAISGSGGSTYYADSVKGRFTISRDNSKNTLY LQMNSLRAEDTAVYYCAKSYGAFDYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPEAAGGPSVF LFPPKPKDTLMISRTPEVTCVVVDVSHEDPEVKFNWYVDG VEVHNAKTKPREEQYNSTYRVVSVLTVLHQDWLNGKEYKC KVSNKALAAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG |
| SEQ ID NO: 6 | Common heavy chain CDR-H1 of GPC3xCD3 bispecific antibodies | TYAMN |
| SEQ ID NO: 7 | Common heavy chain CDR-H2 of GPC3xCD3 bispecific antibodies | RIRSKYNNYATYYADSVKD |
| SEQ ID NO: 8 | Common heavy chain CDR-H3 of GPC3xCD3 bispecific antibodies | HGNFGNSYVSWFAY |
| SEQ ID NO: 9 | Common heavy chain VH of GPC3xCD3 bispecific antibodies | EVQLVESGGGLVQPGGSLKLSCAASGFTFNTYAMNWVRQA PGKGLEWVGRIRSKYNNYATYYADSVKDRFTISRDDSKNT AYLQMNSLKTEDTAVYYCVRHGNFGNSYVSWFAYWGQGTL VTVSS |
| SEQ ID NO: 10 | Common heavy chain HC (LALA + P329A mutations) of GPC3xCD3 bispecific antibodies | EVQLVESGGGLVQPGGSLKLSCAASGFTFNTYAMNWVRQA PGKGLEWVGRIRSKYNNYATYYADSVKDRFTISRDDSKNT AYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALAAPIEKTISKAKGQPREPQVYTLP PSREEMTKNQVSLTCLVKGFYPSDIAVEWESNGQPENNYK TTPPVLDSDGSFFLYSKLTVDKSRWQQGNVFSCSVMHEAL HNHYTQKSLSLSPG |
| SEQ ID NO: 11 | huCD3 1A4 CDR-L1 (L3-1) | RSSTGAVTTSNYAN |
| SEQ ID NO: 12 | huCD3 1A4 CDR-L2 (L3-1) | GTNKRAP |
| SEQ ID NO: 13 | huCD3 1A4 CDR-L3 (L3-1) | ALWYKQRWV |
| SEQ ID NO: 14 | huCD3 VL 1A4 (L3-1) | QTVVTQEPSLTVSPGGTVTLTCRSSTGAVTTSNYANWFQQ KPGQAPRGLIGGINKRAPGTPARFSGSLLGGKAALTSGA QPEDEAEYYCALWYKQRWVFGGGTKLTVL |

TABLE 1-continued

Exemplary Amino Acid Sequences of the Disclosure

| SEQ ID NO: | Name | Amino Acid Sequence |
| --- | --- | --- |
| SEQ ID NO: 15 | huCD3 1A4 LC (L3-1) | QTVVTQEPSLTVSPGGTVTLTCRSSTGAVTTSNYANWFQQ KPGQAPRGLIGGTNKRAPGTPARFSGSLLGGKAALTLSGA QPEDEAEYYCALWYKQRWVFGGGTKLTVL GQPKAAPSVTLFPPSSEELQANKATLVCLISDFYPGAVTV AWKADSSPVK AGVETTTPSKQSNNKYAASSYLSLTPEQWKSHRSYSCQVT HEGSTVEKTVAPTECS |
| SEQ ID NO: 16 | GPC3 binding part AD84 CDR-L1 | QKVTNRE |
| SEQ ID NO: 17 | GPC3 binding part AD84 CDR-L2 | GAT |
| SEQ ID NO: 18 | GPC3 binding part AD84 CDR-L3 | QQWALSPRGWV |
| SEQ ID NO: 19 | GPC3 binding part AD84 VL (light chain variable region) | EIVLTQSPGTLSLSPGERATLSCRASQKVTNRELAWYQQK PGQAPRLLIYGATTKATGIPDRFSGSGSGTDFTLTISRLE PEDFAVYYCQQWALSPRGWVFGQGTKVEIK |
| SEQ ID NO: 20 | GPC3 binding part AD84 LC (light chain) | EIVLTQSPGTLSLSPGERATLSCRASQKVTNRELAWYQQK PGQAPRLLIYGATTKATGIPDRFSGSGSGTDFTLTISRLE PEDFAVYYCQQWALSPRGWVFGQGTKVEIKRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| SEQ ID NO: 21 | GPC3 binding part AD95 CDR-L1 | QKVTNRE |
| SEQ ID NO: 22 | GPC3 binding part AD95 CDR-L2 | GAK |
| SEQ ID NO: 23 | GPC3 binding part AD95 CDR-L3 | QQWALSPRGWV |
| SEQ ID NO: 24 | GPC3 binding part AD95 VL (light chain variable region) | EIVLTQSPGTLSLSPGERATLSCRASQKVTNRELAWYQQK PGQAPRLLIYGAKIRAKGIPDRFSGSGSGTDFTLTISRLE PEDFAVYYCQQWALSPRGWVFGQGTKVEIK |
| SEQ ID NO: 25 | GPC3 binding part AD95 LC (light chain) | EIVLTQSPGTLSLSPGERATLSCRASQKVTNRELAWYQQK PGQAPRLLIYGAKIRAKGIPDRFSGSGSGTDFTLTISRLE PEDFAVYYCQQWALSPRGWVFGQGTKVEIKRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| SEQ ID NO: 26 | GPC3 binding part P44 CDR-L1 | SGSISYDD |
| SEQ ID NO: 27 | GPC3 binding part P44 CDR-L2 | FNN |
| SEQ ID NO: 28 | GPC3 binding part P44 CDR-L3 | QSWDLRHRV |
| SEQ ID NO: 29 | GPC3 binding part P44 VL (light chain variable region) | NFMLTQPHSVSESPGKTVTISCTRSSGSISYDDVQWYQQR PGSSPTTVIYFNNLRPSGVPDRFSGSIDSSSNSASLTISG LKTEDEADYYCQSWDLRHRVFGGGTKLTVL |
| SEQ ID NO: 30 | GPC3 binding part P44 LC (light chain) | NFMLTQPHSVSESPGKTVTISCTRSSGSISYDDVQWYQQR PGSSPTTVIYFNNLRPSGVPDRFSGSIDSSSNSASLTISG LKTEDEADYYCQSWDLRHRVFGGGTKLTVLGQPKAAPSVT LFPPSSEELQANKATLVCLISDFYPGAVTVAWKADSSPVK AGVETTTPSKQSNNKYAASSYLSLTPEQWKSHRSYSCQVT HEGSTVEKTVAPTECS |
| SEQ ID NO: 31 | GPC3 binding part P30 CDR-L1 | SSDVPEDAL |
| SEQ ID NO: 32 | GPC3 binding part P30 CDR-L2 | YDS |

TABLE 1-continued

Exemplary Amino Acid Sequences of the Disclosure

| SEQ ID NO: | Name | Amino Acid Sequence |
|---|---|---|
| SEQ ID NO: 33 | GPC3 binding part P30 CDR-L3 | SSWDFGTGSKV |
| SEQ ID NO: 34 | GPC3 binding part P30 VL (light chain variable region) | QSALTQPASVSGSPGQSITISCTGTSSDVPEDALVSWYQQHPGKAPKLMIYYDSTRPSGVSNRFSGSKSGNTASLTISGLQAEDEADYYCSSWDFGTGSKVFGGGTKLTVL |
| SEQ ID NO: 35 | GPC3 binding part P30 LC (light chain) | QSALTQPASVSGSPGQSITISCTGTSSDVPEDALVSWYQQHPGKAPKLMIYYDSTRPSGVSNRFSGSKSGNTASLTISGLQAEDEADYYCSSWDFGTGSKVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO: 36 | GPC3 binding part P111 CDR-L1 | SSNIGTYY |
| SEQ ID NO: 37 | GPC3 binding part P111 CDR-L2 | SNN |
| SEQ ID NO: 38 | GPC3 binding part P111 CDR-L3 | QSIGFLSLV |
| SEQ ID NO: 39 | GPC3 binding part P111 VL (light chain variable region) | QSVLTQPPSASGTPGQRVTISCSGSSSNIGTYYVNWYQQLPGTAPKLLIYSNNERPSGVPDRFSGSKSGTSASLAISGLQSEDEADYYCQSIGFLSLVFGGGTKLTVL |
| SEQ ID NO: 40 | GPC3 binding part P111 LC (light chain) | QSVLTQPPSASGTPGQRVTISCSGSSSNIGTYYVNWYQQLPGTAPKLLIYSNNERPSGVPDRFSGSKSGTSASLAISGLQSEDEADYYCQSIGFLSLVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO: 41 | CD28 binding part AI3 CDR-L1 | QSVLYSSNNKNY |
| SEQ ID NO: 42 | CD28 binding part AI3 CDR-L2 | WAS |
| SEQ ID NO: 43 | CD28 binding part AI3 CDR-L3 | QQNLRPPET |
| SEQ ID NO: 44 | CD28 binding part AI3 VL (light chain variable region) | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQNLRPPETFGQGTKVEIK |
| SEQ ID NO: 45 | CD28 binding part AI3 LC (light chain) | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQNLRPPETFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 46 | CD28 binding part AI10 CDR-L1 | GDLLEFAGKTY |
| SEQ ID NO: 47 | CD28 binding part AI10 CDR-L2 | EVS |
| SEQ ID NO: 48 | CD28 binding part AI10 CDR-L3 | MQAHGSKIGFT |
| SEQ ID NO: 49 | CD28 binding part AI10 VL (light chain variable region) | DIVMTQTPLSLSVTPGQPASISCKSSGDLLEFAGKTYLYWYLQKPGQPPQLLIYEVSNRFSGVPDRFSGSGSGTDFTLKISRVEAEDVGVYYCMQAHGSKIGFTFGQGTKVEIK |
| SEQ ID NO: 50 | CD28 binding part AI10 LC (light chain) | DIVMTQTPLSLSVTPGQPASISCKSSGDLLEFAGKTYLYWYLQKPGQPPQLLIYEVSNRFSGVPDRFSGSGSGTDFTLKISRVEAEDVGVYYCMQAHGSKIGFTFGQGTKVEIKRTVAAPSVFIFPPSDEQLKSGTASVVCLLNNFYPREAKVQWKVDNA |

TABLE 1-continued

Exemplary Amino Acid Sequences of the Disclosure

| SEQ ID NO: | Name | Amino Acid Sequence |
|---|---|---|
| | | LQSGNSQESVTEQDSKDSTYSLSSTLTLSKADYEKHKVYA CEVTHQGLSSPVTKSFNRGEC |
| SEQ ID NO: 51 | CD28 binding part AI13 CDR-L1 | QSVLYSSNNKNY |
| SEQ ID NO: 52 | CD28 binding part AI13 CDR-L2 | WAS |
| SEQ ID NO: 53 | CD28 binding part AI13 CDR-L3 | QQNFRPPET |
| SEQ ID NO: 54 | CD28 binding part AI13 VL (light chain variable region) | DIVMTQSPDSLAVSLGERATINCKSSQSVLYSSNNKNYLA WYQQKPGQPPKLLIYWASTRESGVPDRFSGSGSGTDFTLT ISSLQAEDVGVYYCQQNFRPPETFGGGTKVEIK |
| SEQ ID NO: 55 | CD28 binding part AI13 LC (light chain) | DIVMTQSPDSLAVSLGERATINCKSSQSVLYSSNNKNYLA WYQQKPGQPPKLLIYWASTRESGVPDRFSGSGSGTDFTLT ISSLQAEDVGVYYCQQNFRPPETFGGGTKVEIKRTVAAPS VFIFPPSDEQLKSGTASVVCLLNNFYPREAKVQWKVDNAL QSGNSQESVTEQDSKDSTYSLSSTLTLSKADYEKHKVYAC EVTHQGLSSPVTKSFNRGEC |
| SEQ ID NO: 56 | Y4 kappa light chain | DIQMTQSPSSLSASVGDRVTITCRASQSISSYLNWYQQKP GKAPKLLIYAASSLQSGVPSRFSGSGSGTDFTLTISSLQP EDFATYYCQQSYSTPNTFGQGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| SEQ ID NO: 57 | ERY974 heavy chain - GPC3 binding arm mutated | QVQLVQSGAEVKKPGASVTVSCKASGYTFTDYEMHWIRQP PGEGLEWIGAIDGPTPDTAYSEKFKGRVTLTADKSTSTAY MELSSLTSEDTAVYYCTRFYSYTYWGQGTLVTVSSASTKG PSVFPLAPCSRSTSESTAALGCLVKDYFPEPVTVSWNSGA LTSGVHTFPAVLQSSGLYSLSSVVTVPSSSLGTQTYTCNV DHKPSNTKVDKRVESKYGPPCPPCPAPEFRGGPKVFLFPP KPKDTLMISRTPEVTCVVVDVSQEDPEVQFNWYVDGVEVH NAKTKPREEQFASTYRVVSVLTVLHQDWLNGKEYKCKVSN KGLPSSIEKTISKAKGQPREPQVYTLPPSQEEMTKNQVSL TCLVKGFYPSDIAVEWQSNGQTENNYKTTPPVLDSDGSFF LYSKLTVDKSRWQEGNVFSCSVMHEALHNHYTQESLSLSP |
| SEQ ID NO: 58 | ERY974 light chain - GPC3 binding arm | DIVMTQSPLSLPVTPGEPASISCRSSQPLVHSNRNTYLHW YQQKPGQAPRLLIYKVSNRFSGVPDRFSGSGSGTDFTLKI SRVEAEDVGVYYCGQGTQVPYTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC |
| SEQ ID NO: 59 | ERY974 heavy chain - CD3 binding arm mutated | QVQLVESGGGVVQPGGSLRLSCAASGFTFSNAWMHWVRQA PGKGLEWVAQIKDKSQNYATYYAESVKGRFTISRADSKNS IYLQMNSLKTEDTAVYYCRYVHYAAGYGVDIWGQGTTVTV SSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEFRGGP KVFLFPPKPKDTLMISRTPEVTCVVVDVSQEDPEVQFNWY VDGVEVHNAKTKPREEQFASTYRVVSVLTVLHQDWLNGKE YKCKVSNKGLPSSIEKTISKAKGQPREPQVYTLPPSQKEM TKNQVSLTCLVKGFYPSDIAVEWESNGQPENNYKTTPPVL DSDGSFFLYSKLTVDKSRWQEGNVFSCSVMHEALHNRYTQ KSLSLSP |
| SEQ ID NO: 60 | ERY974 light chain - CD3 binding arm | DIVMTQSPLSLPVTPGEPASISCRSSQPLVHSNRNTYLHW YQQKPGQAPRLLIYKVSNRFSGVPDRFSGSGSGTDFTLKI SRVEAEDVGVYYCGQGTQVPYTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC |

Tables 2 and 3 shows exemplary bispecific antibodies of the disclosure. Nomenclature for each antibodies are shown and the individual first light chain, second light chain and heavy chain regions of the KA-Bodies of the disclosure are described.

TABLE 2

Exemplary GPC3XCD3 Bispecific Antibodies of the Disclosure

| BsAb name | First light chain (kappa) | Second light chain (lambda) | Heavy chain |
| --- | --- | --- | --- |
| AD84L3-1/N | AD84 | L3-1 | Common VH with LALAPA mutation |
| AD95L3-1/N | AD95 | | |

TABLE 3

Exemplary GPC3XCD28 Bispecific Antibodies of the Disclosure

| BsAb name | First light chain (kappa) | Second light chain (lambda) | Heavy chain |
| --- | --- | --- | --- |
| AI10P44/N | AI10 | P44 | Common VH with LALAPA mutation |
| AI10P30/N | AI10 | P30 | |
| AI10P111/N | AI10 | P111 | |
| AI3P44/N | AI3 | P44 | |
| AI3P30/N | AI3 | P30 | |
| AI3P111/N | AI3 | P111 | |
| AI13P44/N | AI13 | P44 | |
| AI13P30/N | AI13 | P30 | |
| AI13P111/N | AI13 | P111 | |

In some embodiments, the AD84L3-1/N bispecific antibody has a first heavy chain comprising a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; a first light chain comprising a CDRL1 comprising the amino acid sequence of SEQ ID NO: 11, a CDRL2 comprising the amino acid sequence of SEQ ID NO: 12, and a CDRL3 comprising the amino acid sequence of SEQ ID NO: 13; and a second heavy chain comprising a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; and a second light chain comprising a CDRL1 comprising the amino acid sequence of SEQ ID NO: 16, a CDRL2 comprising the amino acid sequence of SEQ ID NO: 17, and a CDRL3 comprising the amino acid sequence of SEQ ID NO: 18.

In some embodiments, the AD84L3-1/N bispecific antibody has a first heavy chain variable region comprising the amino acid sequence of SEQ ID NO: 9, a first light chain variable region comprising the amino acid sequence of SEQ ID NO: 14, a second heavy chain variable region comprising the amino acid sequence of SEQ ID NO: 9, and a second light chain variable region comprising the amino acid sequence of SEQ ID NO: 19.

In some embodiments, the AD84L3-1/N bispecific antibody has a first heavy chain comprising the amino acid sequence of SEQ ID NO: 10, a first light chain comprising the amino acid sequence of SEQ ID NO: 15, a second heavy chain comprising the amino acid sequence of SEQ ID NO: 10, and a second light chain comprising the amino acid sequence of SEQ ID NO: 20.

In some embodiments, the AD95L3-1/N bispecific antibody has a first heavy chain comprising a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; a first light chain comprising a CDRL1 comprising the amino acid sequence of SEQ ID NO: 11, a CDRL2 comprising the amino acid sequence of SEQ ID NO: 12, and a CDRL3 comprising the amino acid sequence of SEQ ID NO: 13; and a second heavy chain comprising a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; and a second light chain comprising a CDRL1 comprising the amino acid sequence of SEQ ID NO: 21, a CDRL2 comprising the amino acid sequence of SEQ ID NO: 22, and a CDRL3 comprising the amino acid sequence of SEQ ID NO: 23.

In some embodiments, the AD95L3-1/N bispecific antibody has a first heavy chain variable region comprising the amino acid sequence of SEQ ID NO: 9, a first light chain variable region comprising the amino acid sequence of SEQ ID NO: 14, a second heavy chain variable region comprising the amino acid sequence of SEQ ID NO: 9, and a second light chain variable region comprising the amino acid sequence of SEQ ID NO: 24.

In some embodiments, the AD95L3-1/N bispecific antibody has a first heavy chain comprising the amino acid sequence of SEQ ID NO: 10, a first light chain comprising the amino acid sequence of SEQ ID NO: 15, a second heavy chain comprising the amino acid sequence of SEQ ID NO: 10, and a second light chain comprising the amino acid sequence of SEQ ID NO: 25.

In some embodiments, the AI10P44/N bispecific antibody has a first heavy chain comprising a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; a first light chain comprising a CDRL1 comprising the amino acid sequence of SEQ ID NO: 46, a CDRL2 comprising the amino acid sequence of SEQ ID NO: 47, and a CDRL3 comprising the amino acid sequence of SEQ ID NO: 48; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 26, a CDRL2 comprising the amino acid sequence of SEQ ID NO: 27, and a CDRL3 comprising the amino acid sequence of SEQ ID NO: 28.

In some embodiments, the AI10P44/N bispecific antibody has a first heavy chain variable region comprising the amino acid sequence of SEQ ID NO: 4, a first light chain variable region comprising the amino acid sequence of SEQ ID NO: 49, a second heavy chain variable region comprising the amino acid sequence of SEQ ID NO: 4, and a second light chain variable region of SEQ ID NO: 29.

In some embodiments, AI10P44/N bispecific antibody has a first heavy chain comprising the amino acid sequence of SEQ ID NO: 5, a first light chain comprising the amino acid sequence of SEQ ID NO: 50, and a second heavy chain comprising the amino acid sequence of SEQ ID NO: 5, and a second light chain comprising the amino acid sequence of SEQ ID NO: 30.

In some embodiments, the AI10P30/N bispecific antibody has a first heavy chain comprising a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; a first light chain comprising a CDRL1 comprising the amino acid sequence of SEQ ID NO: 46, a CDRL2 comprising the amino acid sequence of SEQ ID NO: 47, and a CDRL3 comprising the amino acid sequence of SEQ ID NO: 48; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 31, a CDRL2 comprising the amino acid sequence of SEQ ID NO: 32, and a CDRL3 comprising the amino acid sequence of SEQ ID NO: 33.

In some embodiments, the AI10P30/N bispecific antibody has a first heavy chain variable region comprising the amino acid sequence of SEQ ID NO: 4, a first light chain variable region comprising the amino acid sequence of SEQ ID NO: 49, a second heavy chain variable region comprising the amino acid sequence of SEQ ID NO: 4, and a second light chain variable region of SEQ ID NO: 34.

In some embodiments, AI10P30/N bispecific antibody has a first heavy chain comprising the amino acid sequence of SEQ ID NO: 5, a first light chain comprising the amino acid sequence of SEQ ID NO: 50, and a second heavy chain comprising the amino acid sequence of SEQ ID NO: 5, and a second light chain comprising the amino acid sequence of SEQ ID NO: 35.

In some embodiments, the AI10P111/N bispecific antibody has a first heavy chain comprising a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; a first light chain comprising a CDRL1 comprising the amino acid sequence of SEQ ID NO: 46, a CDRL2 comprising the amino acid sequence of SEQ ID NO: 47, and a CDRL3 comprising the amino acid sequence of SEQ ID NO: 48; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 36, a CDRL2 comprising the amino acid sequence of SEQ ID NO: 37, and a CDRL3 comprising the amino acid sequence of SEQ ID NO: 38.

In some embodiments, the AI10P111/N bispecific antibody has a first heavy chain variable region comprising the amino acid sequence of SEQ ID NO: 4, a first light chain variable region comprising the amino acid sequence of SEQ ID NO: 49, a second heavy chain variable region comprising the amino acid sequence of SEQ ID NO: 4, and a second light chain variable region of SEQ ID NO: 39.

In some embodiments, AI10P111/N bispecific antibody has a first heavy chain comprising the amino acid sequence of SEQ ID NO: 5, a first light chain comprising the amino acid sequence of SEQ ID NO: 50, and a second heavy chain comprising the amino acid sequence of SEQ ID NO: 5, and a second light chain comprising the amino acid sequence of SEQ ID NO: 40.

In some embodiments, the AI3P44/N bispecific antibody has a first heavy chain comprising a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; a first light chain comprising a CDRL1 comprising the amino acid sequence of SEQ ID NO: 41, a CDRL2 comprising the amino acid sequence of SEQ ID NO: 42, and a CDRL3 comprising the amino acid sequence of SEQ ID NO: 43; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 26, a CDRL2 comprising the amino acid sequence of SEQ ID NO: 27, and a CDRL3 comprising the amino acid sequence of SEQ ID NO: 28.

In some embodiments, the AI3P44/N bispecific antibody has a first heavy chain variable region comprising the amino acid sequence of SEQ ID NO: 4, a first light chain variable region comprising the amino acid sequence of SEQ ID NO: 44, a second heavy chain variable region comprising the amino acid sequence of SEQ ID NO: 4, and a second light chain variable region of SEQ ID NO: 29.

In some embodiments, AI3P44/N bispecific antibody has a first heavy chain comprising the amino acid sequence of SEQ ID NO: 5, a first light chain comprising the amino acid sequence of SEQ ID NO: 45, and a second heavy chain comprising the amino acid sequence of SEQ ID NO: 5, and a second light chain comprising the amino acid sequence of SEQ ID NO: 30.

In some embodiments, the AI3P30/N bispecific antibody has a first heavy chain comprising a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; a first light chain comprising a CDRL1 comprising the amino acid sequence of SEQ ID NO: 41, a CDRL2 comprising the amino acid sequence of SEQ ID NO: 42, and a CDRL3 comprising the amino acid sequence of SEQ ID NO: 43; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 31, a CDRL2 comprising the amino acid sequence of SEQ ID NO: 32, and a CDRL3 comprising the amino acid sequence of SEQ ID NO: 33.

In some embodiments, the AI3P30/N bispecific antibody has a first heavy chain variable region comprising the amino acid sequence of SEQ ID NO: 4, a first light chain variable region comprising the amino acid sequence of SEQ ID NO: 44, a second heavy chain variable region comprising the amino acid sequence of SEQ ID NO: 4, and a second light chain variable region of SEQ ID NO: 34.

In some embodiments, AI3P30/N bispecific antibody has a first heavy chain comprising the amino acid sequence of SEQ ID NO: 5, a first light chain comprising the amino acid sequence of SEQ ID NO: 45, and a second heavy chain comprising the amino acid sequence of SEQ ID NO: 5, and a second light chain comprising the amino acid sequence of SEQ ID NO: 35.

In some embodiments, the AI3P111/N bispecific antibody has a first heavy chain comprising a CDRH1 comprising the amino acid sequence of SEQ ID NO: 1, a CDRH2 comprising the amino acid sequence of SEQ ID NO: 2; and a CDRH3 comprising the amino acid sequence of SEQ ID NO: 3; a first light chain comprising a CDRL1 comprising the amino acid sequence of SEQ ID NO: 41, a CDRL2 comprising the amino acid sequence of SEQ ID NO: 42, and a CDRL3 comprising the amino acid sequence of SEQ ID NO: 43; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 36, a CDRL2 comprising the amino acid sequence of SEQ ID NO: 37, and a CDRL3 comprising the amino acid sequence of SEQ ID NO: 38.

In some embodiments, the AI3P111/N bispecific antibody has a first heavy chain variable region comprising the amino acid sequence of SEQ ID NO: 4, a first light chain variable region comprising the amino acid sequence of SEQ ID NO: 44, a second heavy chain variable region comprising the amino acid sequence of SEQ ID NO: 4, and a second light chain variable region of SEQ ID NO: 39.

In some embodiments, AI3P111/N bispecific antibody has a first heavy chain comprising the amino acid sequence of SEQ ID NO: 5, a first light chain comprising the amino acid sequence of SEQ ID NO: 45, and a second heavy chain comprising the amino acid sequence of SEQ ID NO: 5, and a second light chain comprising the amino acid sequence of SEQ ID NO: 40.

In some embodiments, the AI13P44/N bispecific antibody has a first heavy chain comprising a CDRH1 comprising the amino acid sequence of SEQ ID NO: 1, a CDRH2 comprising the amino acid sequence of SEQ ID NO: 2; and a CDRH3 comprising the amino acid sequence of SEQ ID NO: 3; a first light chain comprising a CDRL1 comprising the amino acid sequence of SEQ ID NO: 51, a CDRL2 comprising the amino acid sequence of SEQ ID NO: 52, and a CDRL3 comprising the amino acid sequence of SEQ ID NO: 53; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 26, a CDRL2 comprising the amino acid sequence of SEQ ID NO: 27, and a CDRL3 comprising the amino acid sequence of SEQ ID NO: 28.

In some embodiments, the AI13P44/N bispecific antibody has a first heavy chain variable region comprising the amino acid sequence of SEQ ID NO: 4, a first light chain variable region comprising the amino acid sequence of SEQ ID NO: 54, a second heavy chain variable region comprising the amino acid sequence of SEQ ID NO: 4, and a second light chain variable region of SEQ ID NO: 29.

In some embodiments, AI13P44/N bispecific antibody has a first heavy chain comprising the amino acid sequence of SEQ ID NO: 5, a first light chain comprising the amino acid sequence of SEQ ID NO: 55, and a second heavy chain comprising the amino acid sequence of SEQ ID NO: 5, and a second light chain comprising the amino acid sequence of SEQ ID NO: 30.

In some embodiments, the AI13P30/N bispecific antibody has a first heavy chain comprising a CDRH1 comprising the amino acid sequence of SEQ ID NO: 1, a CDRH2 comprising the amino acid sequence of SEQ ID NO: 2; and a CDRH3 comprising the amino acid sequence of SEQ ID NO: 3; a first light chain comprising a CDRL1 comprising the amino acid sequence of SEQ ID NO: 51, a CDRL2 comprising the amino acid sequence of SEQ ID NO: 52, and a CDRL3 comprising the amino acid sequence of SEQ ID NO: 53; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising the amino acid sequence of SEQ ID NO: 31, a CDRL2 comprising the amino acid sequence of SEQ ID NO: 32, and a CDRL3 comprising the amino acid sequence of SEQ ID NO: 33.

In some embodiments, the AI13P30/N bispecific antibody has a first heavy chain variable region comprising the amino acid sequence of SEQ ID NO: 4, a first light chain variable region comprising the amino acid sequence of SEQ ID NO: 54, a second heavy chain variable region comprising the amino acid sequence of SEQ ID NO: 4, and a second light chain variable region comprising the amino acid sequence of SEQ ID NO: 34.

In some embodiments, AI13P30/N bispecific antibody has a first heavy chain comprising the amino acid sequence of SEQ ID NO: 5, a first light chain comprising the amino acid sequence of SEQ ID NO: 55, and a second heavy chain comprising the amino acid sequence of SEQ ID NO: 5, and a second light chain comprising the amino acid sequence of SEQ ID NO: 35.

In some embodiments, the AI13P111/N bispecific antibody has a first heavy chain comprising a CDRH1 comprising the amino acid sequence of SEQ ID NO: 1, a CDRH2 comprising the amino acid sequence of SEQ ID NO: 2; and a CDRH3 comprising the amino acid sequence of SEQ ID NO: 3; a first light chain comprising a CDRL1 comprising the amino acid sequence of SEQ ID NO: 51, a CDRL2 comprising the amino acid sequence of SEQ ID NO: 52, and a CDRL3 comprising the amino acid sequence of SEQ ID NO: 53; and a second heavy chain comprising the amino acid sequence of SEQ ID NO: 1, a CDRH2 comprising the amino acid sequence of SEQ ID NO: 2, and a CDRH3 comprising the amino acid sequence of SEQ ID NO: 3; and a second light chain comprising a CDRL1 comprising the amino acid sequence of SEQ ID NO: 36, a CDRL2 comprising the amino acid sequence of SEQ ID NO: 37, and a CDRL3 comprising the amino acid sequence of SEQ ID NO: 38.

In some embodiments, the AI13P111/N bispecific antibody has a first heavy chain variable region comprising the amino acid sequence of SEQ ID NO: 4, a first light chain variable region comprising the amino acid sequence of SEQ ID NO: 54, a second heavy chain variable region comprising the amino acid sequence of SEQ ID NO: 4, and a second light chain variable region of SEQ ID NO: 39.

In some embodiments, AI13P111/N bispecific antibody has a first heavy chain comprising the amino acid sequence of SEQ ID NO: 5, a first light chain comprising the amino acid sequence of SEQ ID NO: 55, and a second heavy chain comprising the amino acid sequence of SEQ ID NO: 5, and a second light chain comprising the amino acid sequence of SEQ ID NO: 40.

The disclosure provides a composition comprising a first bispecific antibody of the disclosure (GPC3×CD3) and a second bispecific antibody of the disclosure (GPC3×CD28).

TABLE 4

Exemplary Compositions

| Composition | First bispecific antibody (GPC3XCD3) | Second bispecific antibody (GPC3XCD28) |
|---|---|---|
| 1 | AD84L3-1/N | AI10P44/N |
| 2 | AD84L3-1/N | AI10P30/N |
| 3 | AD84L3-1/N | AI10P111/N |
| 4 | AD84L3-1/N | AI3P44/N |
| 5 | AD84L3-1/N | AI3P30/N |
| 6 | AD84L3-1/N | AI3P111/N |

TABLE 4-continued

Exemplary Compositions

| Composition | First bispecific antibody (GPC3XCD3) | Second bispecific antibody (GPC3XCD28) |
|---|---|---|
| 7 | AD84L3-1/N | AI13P44/N |
| 8 | AD84L3-1/N | AI13P30/N |
| 9 | AD84L3-1/N | AI13P111/N |
| 10 | AD95L3-1/N | AI10P44/N |
| 11 | AD95L3-1/N | AI10P30/N |
| 12 | AD95L3-1/N | AI10P111/N |
| 13 | AD95L3-1/N | AI3P44/N |
| 14 | AD95L3-1/N | AI3P30/N |
| 15 | AD95L3-1/N | AI3P111/N |
| 16 | AD95L3-1/N | AI13P44/N |
| 17 | AD95L3-1/N | AI13P30/N |
| 18 | AD95L3-1/N | AI13P111/N |

In some embodiments, the composition comprises a first bispecific antibody of AD84L3-1/N and a second bispecific antibody of AI10P44/N. In some embodiments, the composition comprises a first bispecific antibody of AD84L3-1/N and a second bispecific antibody of AI10P30/N. In some embodiments, the composition comprises a first bispecific antibody of AD84L3-1/N and a second bispecific antibody of AI10P111/N. In some embodiments, the composition comprises a first bispecific antibody of AD84L3-1/N and a second bispecific antibody of AI3P44/N. In some embodiments, the composition comprises a first bispecific antibody of AD84L3-1/N and a second bispecific antibody of AI3P30/N. In some embodiments, the composition comprises a first bispecific antibody of AD84L3-1/N and a second bispecific antibody of AI3P111/N. In some embodiments, the composition comprises a first bispecific antibody of AD84L3-1/N and a second bispecific antibody of AI13P44/N. In some embodiments, the composition comprises a first bispecific antibody of AD84L3-1/N and a second bispecific antibody of AI13P30/N. In some embodiments, the composition comprises a first bispecific antibody of AD84L3-1/N and a second bispecific antibody of AI13P111/N.

In some embodiments, the composition comprises a first bispecific antibody of AD95L3-1/N and a second bispecific antibody of AI10P44/N. In some embodiments, the composition comprises a first bispecific antibody of AD95L3-1/N and a second bispecific antibody of AI10P30/N. In some embodiments, the composition comprises a first bispecific antibody of AD95L3-1/N and a second bispecific antibody of AI10P111/N. In some embodiments, the composition comprises a first bispecific antibody of AD95L3-1/N and a second bispecific antibody of AI3P44/N. In some embodiments, the composition comprises a first bispecific antibody of AD95L3-1/N and a second bispecific antibody of AI3P30/N. In some embodiments, the composition comprises a first bispecific antibody of AD95L3-1/N and a second bispecific antibody of AI3P111/N. In some embodiments, the composition comprises a first bispecific antibody of AD95L3-1/N and a second bispecific antibody of AI13P44/N. In some embodiments, the composition comprises a first bispecific antibody of AD95L3-1/N and a second bispecific antibody of AI13P30/N. In some embodiments, the composition comprises a first bispecific antibody of AD95L3-1/N and a second bispecific antibody of AI13P111/N.

Methods of Use

Therapeutic formulations of the invention, which include the bispecific antibodies of the invention, are used to treat cancer or alleviate a symptom associated with a cancer, such as, by way of non-limiting example, hepatocellular carcinoma HCC and other GPC3 expressing carcinoma. The present invention also provides methods of treating cancer or alleviating a symptom associated with a cancer. A therapeutic regimen is carried out by identifying a subject, e.g., a human patient suffering from (or at risk of developing) a cancer, using standard methods.

Efficaciousness of treatment is determined in association with any known method for diagnosing or treating the particular immune-related disorder. Alleviation of one or more symptoms of the immune-related disorder indicates that the antibody confers a clinical benefit.

Pharmaceutical Compositions

The antibodies of the invention (also referred to herein as "active compounds"), and derivatives, fragments, analogs and homologs thereof, can be incorporated into pharmaceutical compositions suitable for administration. Such compositions typically comprise the antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention is dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser or other together with instructions for administration.

Definitions

As used herein, including the appended claims, the singular forms of words such as "a," "an," and "the," include their corresponding plural references unless the context clearly dictates otherwise.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$)). Affinity can be measured by common methods known in the art, including KinExA and Biacore and Octet As used herein, the term "antibody" includes, but is not limited to, monoclonal antibodies, polyclonal antibodies, multispecific antibodies (e.g., bispecific antibodies), fully human antibodies, and chimeric antibodies.

As used herein, unless otherwise indicated, "antigen-binding fragment" refers to antigen-binding fragments of antibodies, i.e. antibody fragments that retain the ability to bind to the antigen bound by the full-length antibody, e.g. fragments that retain one or more CDR regions. Examples of antibody binding fragments include, but are not limited to, Fab, Fab', F(ab')2, Fv fragments and individual antibody heavy chains or light chains, and individual heavy chain or light chain variable regions.

A "Fab fragment" is comprised of one light chain and the CH1 and variable regions of one heavy chain. The heavy chain of a Fab molecule cannot form a disulfide bond with another heavy chain molecule. A "Fab fragment" can be the product of papain cleavage of an antibody.

A "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion or fragment of one heavy chain that contains the VH domain and the CH1 domain and also the region between the CH1 and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the CH1 and CH2 domains, such that an interchain disulfide bond is formed between the two heavy chains. A $F(ab')_2$ fragment thus is composed of two Fab' fragments that are held together by a disulfide bond between the two heavy chains. An "$F(ab')_2$ fragment" can be the product of pepsin cleavage of an antibody. The "Fv region" comprises the variable regions from both the heavy and light chains but lacks the constant regions.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In general, the basic "antibody" structural unit comprises a tetramer. In a monospecific antibody, each tetramer includes two identical pairs of polypeptide chains, each pair having one "light" (about 25 kDa) and one "heavy" chain (about 50-70 kDa). The amino-terminal portion of each chain includes a "variable region" or "variable domain" of about 100 to 110 or more amino acids primarily responsible for antigen recognition. The carboxy-terminal portion of the heavy chain may define a constant region primarily responsible for effector function.

Typically, human constant light chains are classified as kappa and lambda light chains. Furthermore, human constant heavy chains are typically classified as mu, delta, gamma, alpha, or epsilon, and define the antibody's isotype as IgM, IgD, IgG, IgA, and IgE, respectively. Subtypes of these IgG include, for example, IgG1 and IgG4.

"Variable region," "variable domain," "V region," or "V chain" as used herein means the segment of IgG chains which is variable in sequence between different antibodies. A "variable region" of an antibody refers to the variable region of the antibody light chain or the variable region of the antibody heavy chain, either alone or in combination. The variable region of the heavy chain may be referred to as "$V_H$." The variable region of the light chain may be referred to as "Vl." Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

A "CDR" refers to one of three hypervariable regions (H1, H2, or H3) within the non-framework region of the antibody VII B-sheet framework, or one of three hypervariable regions (L1, L2, or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable domains. CDR region sequences also have been defined structurally by Chothia as those residues that are not part of the conserved B-sheet framework, and thus are able to adapt to different conformation. Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art. Correspondence between the numbering system, including, for example, the Kabat numbering and the IMGT unique numbering system, is well known to one skilled in the art. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system. In Table 2, sequences are listed using the IMGT nomenclature.

Sequence identity refers to the degree to which the amino acids of two polypeptides are the same at equivalent positions when the two sequences are optimally aligned.

Sequence similarity includes identical residues and non-identical, biochemically related amino acids. Biochemically related amino acids that share similar properties and may be interchangeable are discussed above.

"Conservatively modified variants" or "conservative substitution" refers to substitutions of amino acids in a protein with other amino acids having similar characteristics (e.g.

charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity.

The term "epitope," as used herein, refers to an area or region on an antigen to which an antibody or antigen-binding fragment binds. Binding of an antibody or antigen-binding fragment thereof disclosed herein to an epitope means that the antibody or antigen-binding fragment thereof binds to one or more amino acid residues within the epitope.

"Isolated" nucleic acid molecule or polynucleotide means a DNA or RNA, e.g., of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a polynucleotide comprising" (or the like) a particular nucleotide sequence does not encompass intact chromosomes. Isolated polynucleotides "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to polynucleotide sequences necessary or helpful for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers. In an embodiment of the invention, the polynucleotide is operably linked to a promoter such as a viral promoter, a CMV promoter, an SV40 promoter or a non-viral promoter or an elongation factor (EF)-1 promotor; and/or an intron.

A nucleic acid is "operably linked" when it is placed into a functional relationship with another polynucleotide. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the polynucleotide sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

Host cells include eukaryotic and prokaryotic host cells, including mammalian cells. Host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells and HEK-293 cells. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophia, Pichia koclamae, Pichia membranaefaciens, Pichia minuta* (Ogataea minuta, *Pichia lindnen*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp., *Yarrowia lipolytica*, and *Neurospora crassa*. The present invention includes any host cell (e.g., a CHO cell or *Pichia* cell, e.g., *Pichia pastoris*) containing an anti-ILT4 antibody or antigen-binding fragment thereof or containing a polynucleotide encoding such an antibody or fragment or containing a vector that contains the polynucleotide.

"Treat" or "treating" means to administer antibodies or antigen-binding fragments thereof of the present invention, to a subject having one or more symptoms of a disease for which the antibodies and antigen-binding fragments are effective, e.g., in the treatment of a subject having cancer or an infectious disease, or being suspected of having cancer or infectious disease, for which the agent has therapeutic activity. Typically, the antibody or fragment is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the antibody or fragment may vary according to factors such as the disease stage, age, and weight of the patient, and the ability of the drug to elicit a desired response in the subject.

EXAMPLES

Example 1: Phage Display Selection of GPC3 Fvs Using Human Scfv Libraries Containing Fixed Variable Heavy Domain General procedures for construction and handling of human scFv libraries displayed on M13 bacteriophage are described in Vaughan et al (Human Antibodies with Subnanomolar Affinities Isolated from a Large Non-immunized Phage Display Library. Vaughan, T. et al. Nat Biotechnol 14, 309-314 (1996)), hereby incorporated by reference in its entirety. The libraries for selection and screening encode scFv that all share the same VH domain and are solely diversified in the VL domain. Different VH domain was used for the libraries identifying the GPC3 binders of GPC3×CD3 bispecific antibody on one hand and for the identification of the GPC3 binders of GPC3×CD28 on the other hand. Methods for the generation of fixed VH libraries and their use for the identification and assembly of bispecific antibodies are described in US 2012/0184716 and WO 2012/023053, each of which is hereby incorporated by reference in its entirety. The procedures to identify scFv binding to human GPC3 (huGPC3) are described below. Selections were performed in solution with biotinylated huGPC3 protein and/or on cells expressing huGPC3. Selection strategies included up to 4 round of selections (i) on the recombinant protein, (ii) 2 rounds on the recombinant protein followed by 2 rounds on cells.

Protein Selections

Aliquots of scFv phage libraries were blocked with PBS containing 2% (w/v) skimmed milk. Blocked phages were first deselected on streptavidin/neutravidin magnetic beads (Dynabeads™ MyOne™ Streptavidin TI Magnetic Beads or Sera-Mag SpeedBeads Neutravidin™ Coated Magnetic Particles) then pre-incubated with 100 nM, 50 nM or 5 nM of biotinylated recombinant human GPC3 (GP3-H82E5 AcroBiosystems or in house produced). The phage+antigen mix was then captured by blocked magnetic beads (the same kind used for the deselection) and washed five times with PBS/0.1% Tween® 20 and twice with PBS only. Phages were eluted with 1 mg/mL Trypsin and, after the addition of AEBSF to block trypsin activity, directly added to exponentially growing TG1 cells. An aliquot of the infected TG1 was serial diluted to titer the selection outputs. Outputs were then rescued and used for the next round of selection.

Example 2: Phage Display Selection of CD28 Fvs Using Human Scfv Libraries Containing Fixed Variable Heavy Domain General procedures for construction and handling of human scFv libraries displayed on M13 bacteriophage are the same as described above. The procedures to identify scFv binding to human CD28 (huCD28) are described below. Selections were performed in solution with biotinylated huCD28 protein and/or on cells expressing huCD28. Selection strategies included up to 4 round of selections (i) on the recombinant protein, (ii) alternating recombinant protein and cells, (iii) 2 rounds on the recombinant protein followed by 2 rounds on cells.

Protein Selections

Aliquots of scFv phage libraries were blocked with PBS containing 2% (w/v) skimmed milk. Blocked phages were first deselected on streptavidin/neutravidin magnetic beads (Dynabeads™ MyOne™ Streptavidin TI Magnetic Beads or Sera-Mag SpeedBeads Neutravidin™ Coated Magnetic Particles) then pre-incubated with 200 nM, 100 nM, 50 nM or 5 nM of biotinylated recombinant human CD28 (CD8-H82E5, Acro Biosystems). The phage+antigen mix was then captured by blocked magnetic beads (the same kind used for the deselection) and washed five times with PBS/0.1% Tween® 20 and twice with PBS only. Phages were eluted with 1 mg/mL Trypsin and, after the addition of AEBSF to block trypsin activity, directly added to exponentially growing TG1 cells. An aliquot of the infected TG1 was serial diluted to titer the selection outputs. Outputs were then rescued and used for the next round of selection.

Cell Surface Selections

Phage containing supernatants were blocked with PBS containing 10% FBS. Blocked phages were first deselected on CD28 negative TIB-153 cells (ATCC TIB 153) and then selected on CD28 positive Jurkat cells (Jurkat Clone E6-1, ATCC TIB 152). Cells were pelleted and washed five times with PBS containing 10% FBS follow by a single wash with PBS only. Phages were eluted with 1 mg/mL Trypsin and, after the addition of AEBSF to block trypsin activity, directly added to exponentially growing TG1 cells. An aliquot of the infected TG1 was serial diluted to titer the selection outputs. Outputs were then rescued and used for the next round of selection.

Example 3: Screening for Scfv Binding/Non-Binding to Human Gpc3

Screening of scFv for binding to GPC3 was tested either by ELISA using biotinylated huGPC3-His (or biotinylated Irrelevant protein huMSLN as negative control) or by flow cytometry using GPC3 positive (Hep G2) and GPC3 negative (SK-HEP-1) cells.

ELISA

For the binding ELISA, neutravidin-coated plates were blocked with 1% casein in PBS. Biotinylated huGPC3-His and biotinylated huMSLN (Mesothelin) were captured at 5 nM. Dilution of freshly prepared periplasmic extracts containing the selected scFvs were applied to the plates and detected using a combination of mouse anti-c-myc antibody and donkey anti mouse IgG HRP antibody. The OD at 450 nm generated following the addition of TMB was measured using a microplate spectrophotometer. Hits were classified as specific binders if unable to bind to the irrelevant huMSLN protein and if the OD450 on huCD28 was at least 3 times higher than the background OD450.

Flow Cytometry

For flow cytometry binding assays, cells were harvested, washed and distributed into V bottom 96 well plate at 150'000 or 200'000 cells/well. Dilution of freshly prepared periplasmic extracts containing the selected scFvs were pre-incubated with mouse anti-c-myc antibody and added to the cells. After incubation, cells were washed, incubated with a goat anti-mouse IgG-APC detection antibody, and analyzed in an iQUE3 screener equipment (Sartorious). Hits were classified as positive and specific if at least 5% of the cells were displaying a binding signal on Hep G2 (ATCC HB-8065) cells 3 times greater than the GeoMFI of the background and if such signal was not observed on SK-HEP-1 (ATCC HTB-52) cells.

Positive and specific hits were sequenced following DNA extraction from single clones.

Example 4: Screening for Scfv Binding/Non-Binding to Human Cd28

Screening of scFv for binding to CD28 was tested either by ELISA using biotinylated huCD28-His (or biotinylated huCEA_ECD as negative control) or by flow cytometry using CD28 positive (Jurkat) and CD28 negative (TIB-153) cells.

ELISA

A similar methodology was used as described above for anti-GPC3 scFvs screening. Instead of using recombinant huGPC3, biotinylated huCD28-His and biotinylated huCE-A_ECD were captured at 5 nM on neutravidin-coated plates.

Flow Cytometry

A similar methodology was used as described above for anti-GPC3 scFvs screening. Jurkat cells and TIB-153 cells were used as CD28 positive and CD28 negative cells respectively.

Example 5: Fixed VH Candidates Reformatting into IgG and Transient Expression in Mammalian Cells After screening and sequencing, scFv candidates with the desired binding properties were reformatted into IgG and expressed by transient transfection into PEAK cells. The VH and VL sequences of selected scFv were amplified with specific oligonucleotides and cloned into an expression vector containing the heavy and light chain constant regions. The expression vectors were verified by sequencing and transfected into mammalian cells using Lipofectamine 2000 (Thermo Fisher Scientific) according to manufacturer's instructions. Briefly, 4×106 PEAK cells were cultured in T75 flasks in 25 mL culture media containing fetal bovine serum. Transfected cells were cultured for 5-6 days at 37° C., IgG production was quantified using an Octet RED96 instrument. The supernatant was harvested for IgG purification on FcXL affinity resin (Thermo Fisher Scientific) according to manufacturer's instructions. Briefly, supernatants from transfected cells were incubated overnight at 4° C. with an appropriate amount of FcXL resin. After resin wash with PBS, samples were loaded on Amicon Pro column and the IgG consequently eluted in 50 mM Glycine pH 3.5. The eluted IgG fraction was then dialyzed by Amicon 50 kDa against Histidine NaCl pH 6.0 buffer and the IgG content is quantified by absorption at 280 nm. Purity and IgG integrity were verified by electrophoresis using an Agilent Bioanalyzer 2100 according to manufacturer instructions (Agilent Technologies).

Example 6: Binding of Anti-GPC3 mAbs to GPC3-Positive Cells

The binding capacity of the anti-GPC3 antibody arms of the invention, tested as bivalent mAbs, was assessed by flow cytometry using e.g. Hep G2, Hep 3B or SK-HEP-1 cells.

Cells were harvested, checked for viability, and counted. 200'000 cells were incubated for 15 minutes at 4° C. with increasing concentrations of the antibodies diluted in FACS buffer (PBS 2% BSA). Cells were washed twice with cold FACS buffer and re-incubated for further 15 minutes at 4° C. with a suitable anti-human IgG secondary antibody. Cells were washed twice with cold FACS buffer and resuspended in 150 µl FACS buffer with a compatible viability marker. Binding of antibodies to living cells was measured by flow cytometry using a Cytoflex Platform (Beckman Coulter). Data was analyzed with FlowJo™ v10 software (BD Life Sciences) and dose-response binding curves were drawn using GraphPad Prism 9 software. AD84 GPC3 arm of the GPC3×CD3 bispecific antibody and P44, P30, P111 GPC3 arms of the GPC3×CD28 bispecific antibodies of this invention were selected from this screening process based on their specificity and binding signal intensity to GPC3 positive cells.

Example 7: Binding of Anti-Cd28 Mabs to Cd28-Positive Cells

The binding capacity of the anti-CD28 antibody arms of the invention, tested as bivalent mAbs, was assessed using Jurkat cells (Jurkat Clone E6-1, ATCC TIB 152) by flow cytometry. The flow cytometry methodology was the same as the one described above. AI3 and AI10 CD28 binding arms were selected from this screening process based on their specificity and binding signal intensity to CD28 positive cells.

Example 8: Expression and Purification of Bispecific Antibodies Carrying A Lambda and a Kappa Light Chain The simultaneous expression of one heavy chain and two lights chain in the same cell can lead to the assembly of three different antibodies. Simultaneous expression can be achieved in different ways such as that the transfection of multiple vectors expressing one of the chains to be co-expressed or by using vectors that drive multiple gene expression.

Here, the two light chains were cloned into the vector pNovi KHA that was previously generated to allow for the co-expression of one heavy chain, one Kappa light chain and one Lambda light chain as described in US20120184716 and WO2012023053, each of which is hereby incorporated by reference in its entirety. The expression of the three genes is driven by human cytomegalovirus promoters (hCMV) and the vector also contains a glutamine synthetase gene (GS) that enables the selection and establishment of stable cell lines. The common VH and the VL genes of the anti-CD3 IgG (L3-1/N) and of the anti-GPC3 IgG (AD84) or of the anti-CD28 IgG (AI3 or AI10) and of the anti-GPC3 (P44, P30 or P111) IgG were cloned in the vector pNovi KHA, for transient expression in mammalian cells. Expi293 cells were cultured in suspension in an appropriate Erlenmeyer flask with suitable number of cells and culture medium volume. Plasmid DNA was transfected into Expi293 cells using PEI. Antibody concentration in the supernatant of transfected cells was measured during the production using an Octet RED96. According to antibody concentration, supernatants were harvested 5 to 7 days after transfection and clarified by filtration after addition of diatomaceous earth (Sartorius). The purification was based on a three-step purification process. First, the CaptureSelect™ FcXL affinity matrix (Thermo Fisher Scientific) was washed with PBS and then added in the clarified supernatant. After incubation overnight at +4° C. and 20 rpm, supernatants were centrifuged at 2000 g for 10 min, flow through was stored and resin were washed twice with PBS. Then, the resin was transferred on Amicon Pro columns and a solution containing 50 mM glycine at pH 3.5 was used for elution. Several elution fractions were generated, neutralized with Tris-HCl pH7.4 and pooled. The pool containing total human IgGs (the bispecific and the two monospecific antibodies) was quantified using a Nanodrop spectrophotometer (NanoDrop Technologies). A small aliquot was stored for further analysis and the remaining sample was incubated for 30 min at RT and 20 rpm with the appropriate volume of CaptureSelect™ KappaXL affinity matrix (Thermo Fisher Scientific). Resin recovery and wash, elution and neutralization steps were performed as described above. The last affinity purification step was performed using the CaptureSelect™ lambda Fab affinity matrix (Thermo Fisher Scientific) applying the same process as for the kappa purification step. Alternatively, the purification was based on a two-step purification process, where only the CaptureSelect™ KappaXL affinity matrix and the CaptureSelect™ lambda Fab affinity matrix were used. All elution fractions were pooled and desalted against His-NaCl pH 6.0 formulation buffer using 50 kDa Amicon Ultra centrifugal filter units (Merck Millipore). The final product was quantified using the Nanodrop.

Purified bispecific antibodies were analyzed by electrophoresis in denaturing and reducing conditions using an Agilent 2100 Bioanalyzer with the Protein 80 kit as described by the manufacturer (Agilent Technologies). The aggregate level was determined by SEC-UPLC. All samples were tested for endotoxin contamination using the Limulus Amebocyte Lysate test (LAL; Charles River Laboratories).

Example 9: In Vitro Characterization of Bispecific Antibodies

Binding of the GPC3×CD3 bispecific antibody to GPC3 positive Hep G2 cells, CD3 positive Jurkat cells, and GPC3 negative/CD3 negative SK-HEP-1 cells To demonstrate the binding of the GPC3×CD3 KA-body (e.g. AD84L3-1/N) to target cells, a series of experiments based on flow cytometry was performed. Cell staining and binding assessment was performed as described in Example 6. Binding curves were obtained using GPC3 positive Hep G2 (FIG. 1A), CD3 positive Jurkat (FIG. 1B) and GPC3 negative/CD3 negative SK-HEP-1 cells (FIG. 1C). hIgG1 denotes an irrelevant monoclonal antibody of hIgG1 Fc that served as isotype control. ERY974, described in WO2017/159287 A1, is used as a reference comparator.

Figure 1B:
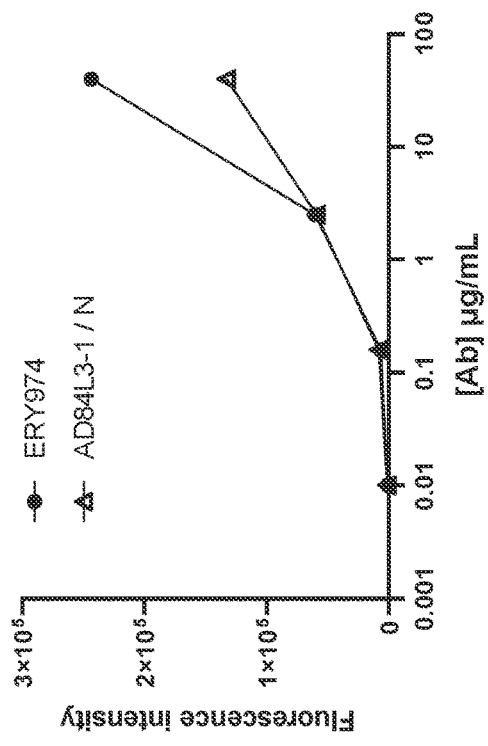
FIGS. 1A-1C are a series of graphs showing concentration dependent binding of the glypican-3 (GPC3)×CD3 bispecific antibody of the invention (AD84L3-1/N) to GPC3 expressing Hep G2 cells (FIG. 1A), CD3 expressing Jurkat cells (FIG. 1B) and GPC3 and CD3 double negative SK-HEP-1 cells (FIG. 1C).
Figure 1A:
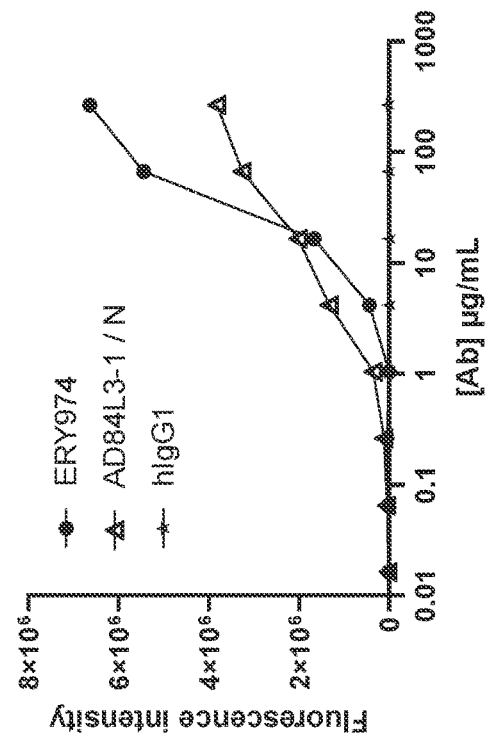
Figure 1C:
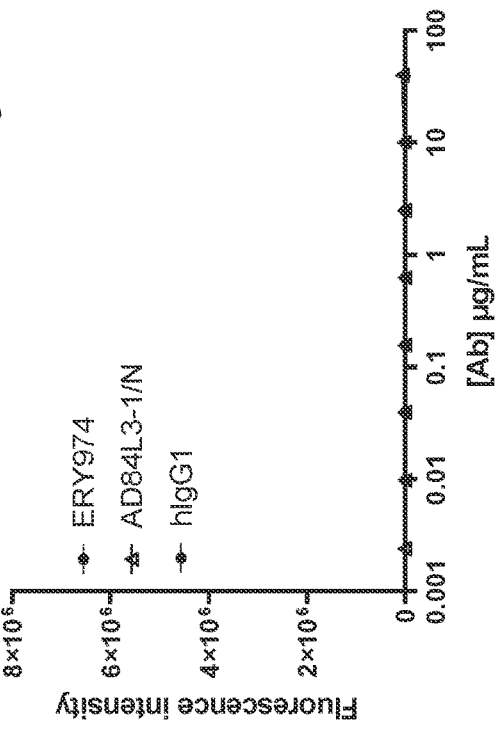

The bispecific binding ability of AD84L3-1/N was confirmed by flow cytometry using cells expressing GPC3 or CD3 antigen (FIG. 1A and FIG. 1B). Results in FIG. 1A and FIG. 1B demonstrated that ERY974 show a higher maximal binding activity to both Hep G2 and Jurkat cells. No binding on non-expressing GPC3 and CD3 cells (SK-HEP-1) is observed for both AD84L3-1/N and ERY974 (FIG. 1C).

Figure 2A:
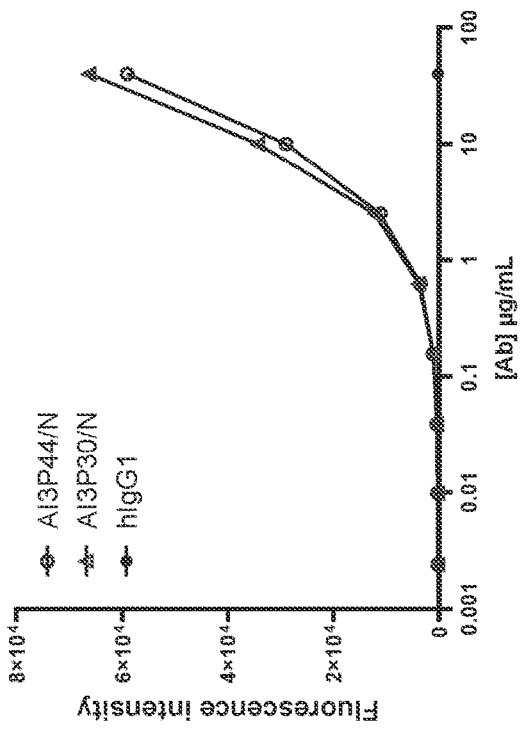
FIGS. 2A-2C are a series of graphs showing concentration dependent binding of the GPC3×CD28 bispecific antibodies of the invention (AI3P44/N and AI3P30/N) to GPC3 expressing FU97 cells (FIG. 2A), CD28 expressing Jurkat cells (FIG. 2B) and GPC3 and CD28 double negative TIB-153 cells (FIG. 2C). These two GPC3×CD28 bsAbs contain the same anti-CD28 AI3 arm, paired with two GPC3 arms (either P44 or P30), both binding to the distal part of the GPC3 receptor. hIgG1 is used as an isotype control.
Figure 2B:
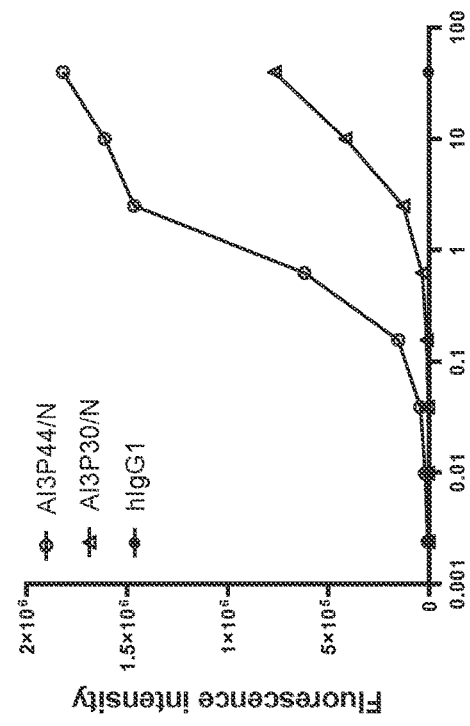
Figure 2C:
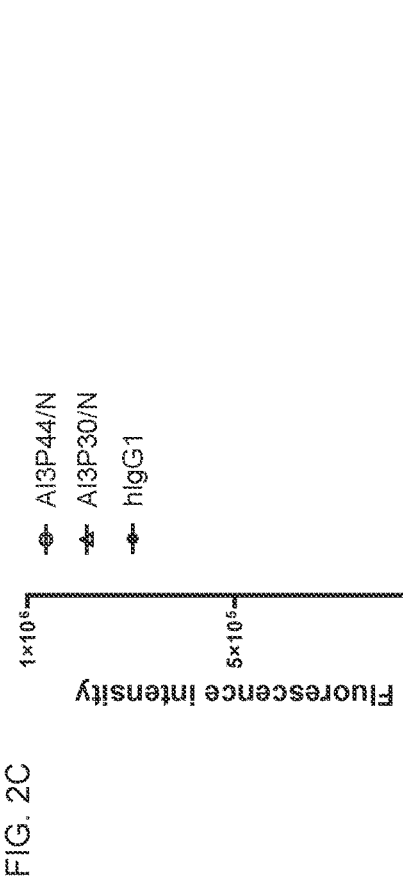

Binding of the GPC3×CD28 bispecific antibodies to GPC3 positive FU97 cells, CD28 positive Jurkat cells, and GPC3 negative/CD28 negative TIB-153 cells To demonstrate the binding of two GPC3×CD28 KA-bodies (AI3P44/N and AI3P30/N) to target cells, a series of experiments based on flow cytometry was performed. Examples of cells that can be used include GPC3 positive cell lines such as the gastric carcinoma cell line FU97 (JCRB1074), CD28 positive cell lines such as the leukemic Jurkat T cells as well as GPC3/CD28 double negative cell line, such as the leukemic TIB-153 cells. Cell staining and binding assessment was performed as described in Example 6. The resulting binding profile is shown in FIGS. 2A-2C. An irrelevant hIgG1 mAb served as negative isotype control and was used in all shown experiments for comparison. Binding data on FU97 cells (FIG. 2A) emphasizes the range of binding affinities for huGPC3 of the selected anti-GPC3 arms of the invention, P44 and P30. Both P44 and P30 arms are binding to membrane distal domains within GPC3. Binding on CD3 positive Jurkat cells highlight how these two CD28×GPC3 bispecific antibodies sharing the same anti-CD28 arm (e.g. AI3) bind similarly to CD28 positive cells (FIG. 2B). The absence of binding signal on the GPC3/CD28 negative TIB-153 cell line suggest that all binding arms of the invention are specific for the designated targets (FIG. 2C).

Example 10: T-Cell Dependent Cellular Cytotoxicity (Tdcc) Mediated by Bispecific Antibodies Once the co-engagement of each bispecific antibody has been confirmed, the capacity of GPC3×CD3 and GPC3×CD28 bispecific antibodies combination to kill tumoral cells in presence of PBMC effector cells was tested using a panel of GPC3 positive malignant cells.

The T-cell dependent cellular cytotoxicity (TDCC) of GPC3 positive and negative tumor cell lines induced by the GPC3×CD3 bispecific antibody tested alone or in combination with GPC3×CD28 bispecific antibodies of the present invention was assessed using human peripheral blood mononuclear cells PBMCs as effector cells. A minimum of 3 different donors was used in each experiment.

Target cells are detached with cell dissociation solution after two washes with PBS. After a centrifugation step, cells are resuspended in assay media, adjusted to the needed concentration, and plated in 96-well plates.

PBMCs were isolated from buffy coats derived from healthy human donors using SepMate™ Tubes (Stemcell Technologies) with Lymphoprep™ buffer (Stemcell Technologies).

For the TDCC assay, PBMCs were added to target cells at final ET ratio of 20:1 (Engineering a bispecific antibody with a common light chain: Identification and optimization of an anti-CD3 epsilon and anti-GPC3 bispecific antibody, ERY974. Shiraiwa et al., Methods, 2018). A dose range of GPC3×CD3 and a fixed dose of the GPC3×CD28 antibodies of the invention (0.5, 0.1, 0.05 or 0.025 µg/mL, unless stated otherwise) were added to the pre-plated target and effector cells. Alternatively, an untargeted CD3 bispecific antibody (Y4L3-1/N) was used instead of the GPC3×CD3 (AD84L3-1/N). hIgG1 was used as an isotype control. ERY974 single agent treatment was used as a reference comparator. Target cell killing was assessed after 48 h of incubation at 37° C., 5% CO2 by quantifying the LDH released into the medium by apoptotic/necrotic cells (Cytotoxicity Detection KitPLUS (LDH), Roche). Maximal LDH release (=100% lysis) was obtained by incubating target cells with the lysis solution provided with the kit. Spontaneous LDH release (=0% lysis) refers to target cells co-incubated with effector cells without any antibody added. TDCC curves were plotted using GraphPad Prism 9. TDCC data are presented in FIGS. 3 to 6. EC50 (half maximal concentration to mediate killing) and Emax (maximal killing percentage at the tested dose range) were determined using GraphPad Prism software. EC50 and Emax values are summarized using Hep G2 (Table 5A) or Hep 3B (Table 5B) target cells and 2 PBMC donors as a source of effector cells. FIGS. 10A-10F illustrate an assessment of target cell killing by quantifying the remaining number of viable adherent cells in culture after 72 h using Promega's CellTiter-Glo® (G7570) and comparing the value obtained in each treated well to the reference (i.e. untreated well (=0% killing)).

TDCC with Hep G2 or Hep 3B

CD3 and CD28 bispecific antibodies combination therapy demonstrated increased potency (lower EC50) and maximum killing (Emax), in the dose range tested, compared with GPC3×CD3 bispecific antibody as single agent treatment regarding killing of the GPC3-expressing cancer cell line Hep G2 (Table 5A) and Hep 3B (Table 5B). EC50 and Emax range values are derived from two representative PBMC donors used as a source of effector cells.

TABLE 5A

TDCC in Hep G2 cells

| Ab | EC50 (ng/mL)* | Emax (% max killing)* |
|---|---|---|
| AD84L3-1/N single ttt | 200-600 | 3-5 |
| +AI3P44/N @ 500 ng/mL | 2-4 | 40-45 |
| +AI3P44/N @ 100 ng/mL | 6-10 | 30-35 |
| +AI3P44/N @ 50 ng/mL | 20-30 | 12-14 |
| +AI3P44/N @ 25 ng/mL | 150-200 | 5-6 |

TABLE 5B

TDCC in Hep 3B cells

| Ab | EC50 (ng/mL)* | Emax (% max killing)* |
|---|---|---|
| AD84L3-1/N single ttt | N/A | N/A |
| +AI3P44/N @ 500 ng/mL | 3-5 | 30-35 |
| +AI3P44/N @ 100 ng/mL | 6-10 | 20-25 |
| +AI3P44/N @ 50 ng/mL | 40-50 | 10-20 |
| +AI3P44/N @ 25 ng/mL | 150-200 | 5-6 |

*in the dose range tested

The GPC3×CD28 bispecific antibodies tested (e.g. AI3P44/N) synergized with the GPC3×CD3 bispecific antibody of the present invention (e.g. AD84L3-1/N) to kill GPC3-positive Hep G2 target cells expressing 700'000 GPC3/cell. The killing induced by two different PBMC donors is shown in FIGS. 3A-3B. Compared to AD84L3-1/N single treatment, synergy of the combination can be observed as a lower EC50 and as a higher overall killing at the maximum concentration tested. Importantly, the dose of the GPC3×CD28 bispecific antibody can be adapted to better control the synergistic effect (see also Table 5A). AD84L3-1/N GPC3×CD3 in combination with 100 ng/mL to 500 ng/ml of AI3P44/N is at least as good as ERY974 single treatment (FIGS. 3A-3B). The GPC3 negative cell line, SK-HEP-1, is not killed by any treatment demonstrating the importance of engaging GPC3 to mediate TDCC (FIGS. 3C-3D).

The capacity of the GPC3×CD28 bispecific antibody (e.g. AI3P44/N) to enhance killing of GPC3-expressing tumor cells in presence of the GPC3×CD3 bispecific antibody, was tested and compared to other GPC3×CD28 bispecific antibodies of the present invention. These CD28 bispecific antibodies are sharing the same CD28 arm (e.g. AI3) but paired with different GPC3 arms, P30 or P111. The GPC3 arms P44 and P30 are targeting membrane distal regions within GPC3. The P111 GPC3 arm is binding membrane proximal like AD84L3-1/N and not competing with the GPC3 arm of the CD3 bispecific antibody for binding to GPC3. Also, the P44 and P30 arms are not competing with the GPC3 arm of the CD3 bispecific antibody. The resulting CD28 bispecific antibodies were tested in the same conditions as in FIG. 3. Combinations of AD84L3-1/N with AI3P44/N, AI3P30/N and AI3P111/N are shown in FIGS. 4A-4C respectively. Using GPC3-positive Hep G2 target cells, data show that synergistic TDCC is observed regardless of the GPC3×CD28 bispecific antibody used in the combination. Killing activity can be fine-tuned by lowering the concentration of each GPC3×CD28 bispecific antibodies (FIGS. 4A-4C). ERY974 included as reference showed equivalent maximal killing as the CD28 bispecific antibodies KA-bodies when tested at the highest concentration (0.5 or 0.1 m/mL), except for candidate AI3P111/N tested in combination (FIG. 4C), which consistently resulted in weaker activity in vitro compared to AI3P44/N (FIG. 4A) or AI3P30/N (FIG. 4B) combination. Overall, the data presented in the present invention demonstrate that GPC3× CD28 KA-bodies can boost GPC3×CD3 κλ-body (AD84L3-1/N) TDCC, to a level similar or above to ERY974 single treatment. The resulting TDCC activity can be attenuated either by decreasing CD28-KA bodies concentration or by using another GPC3 arm (e.g. P111, GPC3 membrane proximal). Importantly, if GPC3×CD3 is replaced by Y4L3-1/N (an untargeted CD3 bispecific antibody unable to deliver signal 1 to T cells), no killing is induced by any of the CD28 bispecific antibodies included in the combination, highlighting the importance of primary T cell stimulation (signal 1) for the activity of CD28-bispecific antibodies (FIGS. 4A-4C).

Figure 5A:
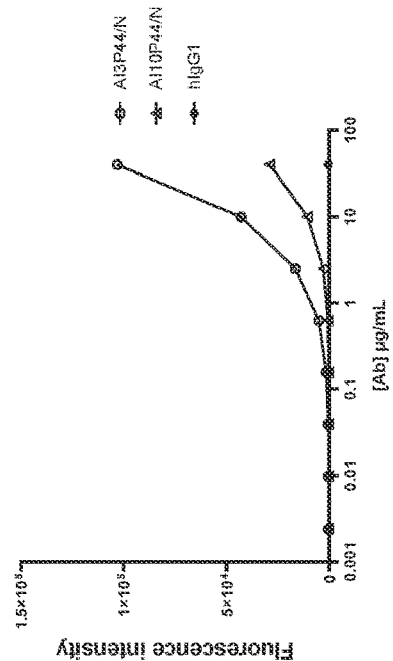
FIGS. 5A-5D are a series of graphs showing a comparison of two GPC3×CD28 biAbs generated using the same membrane distal GPC3 binding arm P44, paired to anti-CD28 arms of different binding affinities to CD28, AI3 or AI10. Concentration dependent binding of the GPC3×CD28 bsAbs of the invention (AI3P44/N and AI10P44/N) to the GPC3 expressing cell line HuH-7 (FIG. 5A) and CD28 expressing Jurkat cells (FIG. 5B). The GPC3 targeting arm demonstrated similar binding signal to GPC3 positive cells for AI3P44/N and AI10P44/N (FIG. 5A). In contrast, the CD28 binding part of the two GPC3×CD28 bsAbs show superior binding signal with AI3 compared to AI10 on CD28 positive cells (FIG. 5B). T-cell retargeted killing/lysis of the GPC3 positive cell line Hep G2 is observed (FIGS. 5C and 5D) with a dose response of the GPC3×CD3 bispecific antibody AD84L3-1/N both in monotherapy, and combined with fixed doses (0.5; 0.1 or 0.05 µg/mL) of GPC3×CD28 bsAbs of the invention, i.e. AI3P44/N (FIG. 5C) and AI10P44/N (FIG. 5D). Synergy between all combination of GPC3×CD3 bsAb and GPC3×CD28 bsAbs in killing GPC3-positive Hep G2 target cells is observed. Killing is dose-dependent regarding the concentration of the GPC3×CD28 bsAb. Based on TDCC data, affinity of the CD28 arm impacts on activity. At intermediate concentrations of GPC3×CD28 κλ-bodies, lower TDCC activity is observed for combination with AI10P44/N compared with AI3P44/N. Y4L3-1/N is an CD3 only targeting monovalent antibody which does not bridge tumor cells and T-cells and thus is used as a negative control. ERY974single treatment is used as a clinical reference comparator for activity. As for the control, no killing is observed in the absence of the GPC3×CD3 bsAb providing the GPC3-driven signal 1 (FIGS. 5C and 5D). Data are presented using a representative PBMC donor in each condition.
Figure 5C:
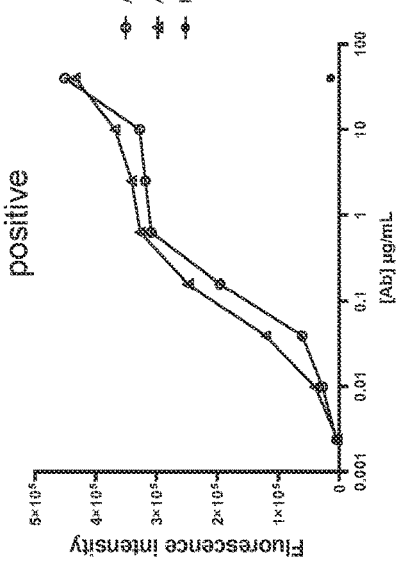
Figure 5B:
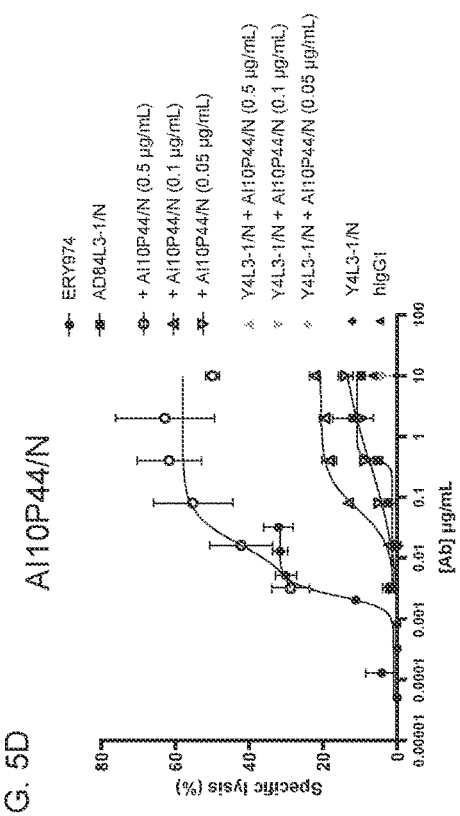
Figure 5D:
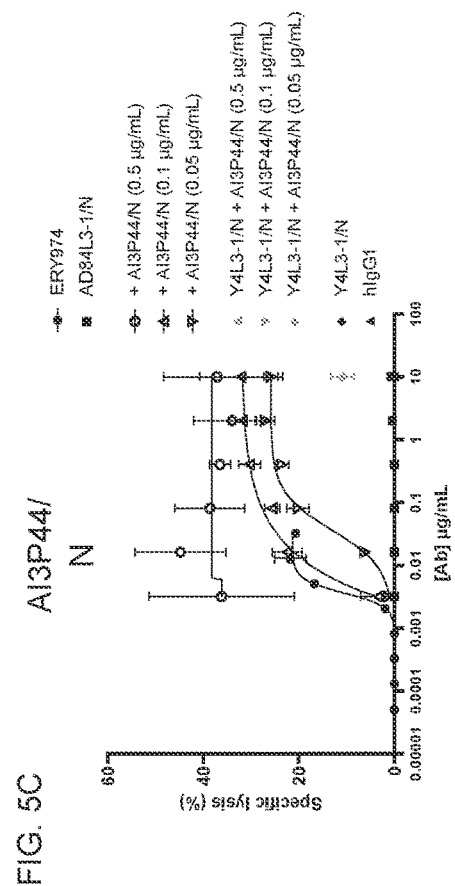

Another set of TDCC experiments were conducted to evaluate the effect of a lower anti-CD28 arm (e.g. AI10) on TDCC activity, when paired with one of the GPC3 binding arm of the present invention (e.g. P44). Data show that both CD28 bispecific antibodies (AI3P44/N and AI10P44/N) bind similarly to GPC3 positive cells, with all P44-containing antibodies displaying equivalent dose-range profiles (FIG. 5A). Data showing binding range with the AI3-containing bispecific antibody demonstrates high binding signal on CD28 positive cells (Jurkat) compared to the AI10-containing bispecific antibody (FIG. 5B). This data demonstrates a lower binding affinity of the CD28 AI10 binding arm compared to the AI3 binding arm. Antibody combinations were then tested using the optimized dose range fixed previously. Using the GPC3 expressing cell line Hep G2, TDCC data suggests that activity reflect the affinity of the CD28 arm. At the intermediate concentrations of GPC3×CD28 KA-bodies, higher TDCC activity were observed for AI3P44/N compared to AI10P44/N combination (FIGS. 5C and 5D, respectively). Nevertheless, increasing the concentration of the lower affinity CD28 bispecific antibody (e.g. AI10P44/N) can further boost synergistic killing activity above the level of ERY974 single treatment (FIG. 5D).

Figure 6A:
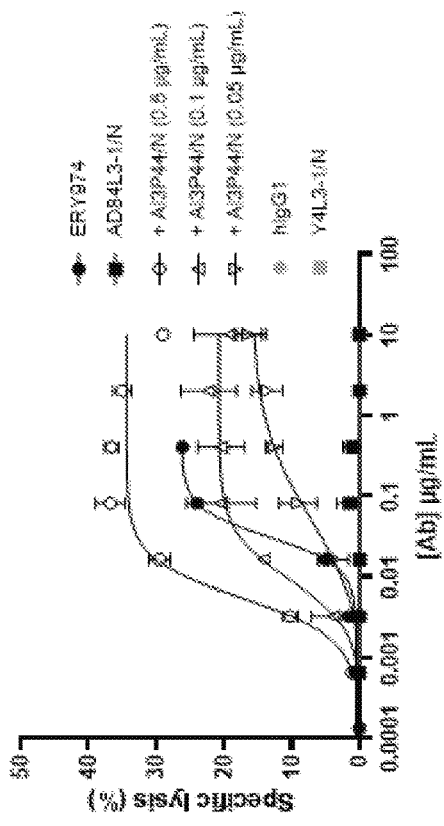
FIGS. 6A-6E a series of graphs showing T-cell retargeted killing/lysis of GPC3-expressing cell line Hep 3B by the GPC3×CD3 bsAb (AD84L3-1/N) in combination with the GPC3×CD28 bispecific antibodies of the invention: AI3P30/N (1 PBMC donor) (FIG. 6A), AI3P44/N (three different PBMC donors) (FIG. 6B, 6C, 6D) and AI10P44/N (FIG. 6E). No or only minimal killing by the GPC3×CD3
Figure 6B:
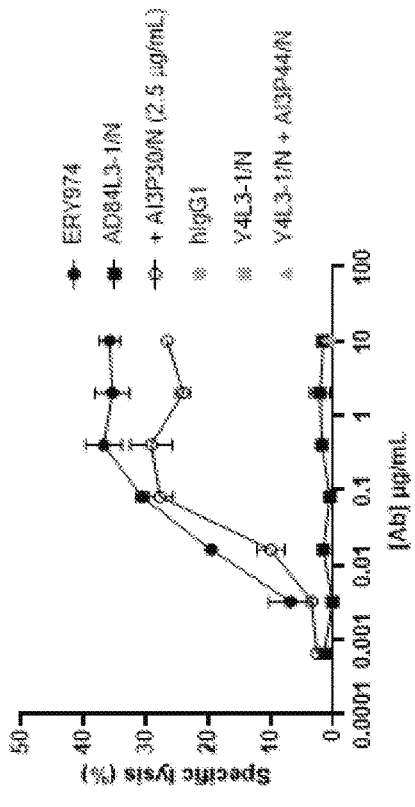
Figure 6C:
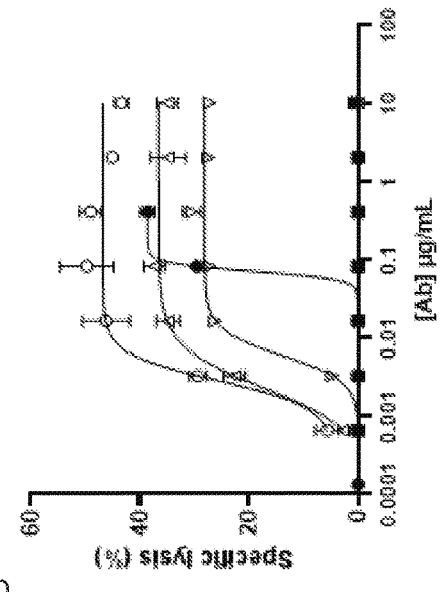
Figure 6D:
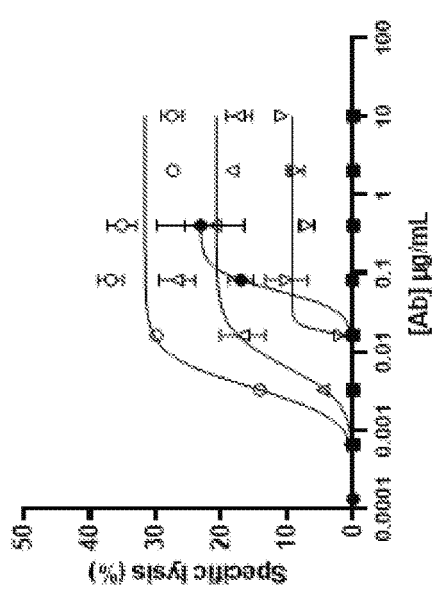
Figure 6E:
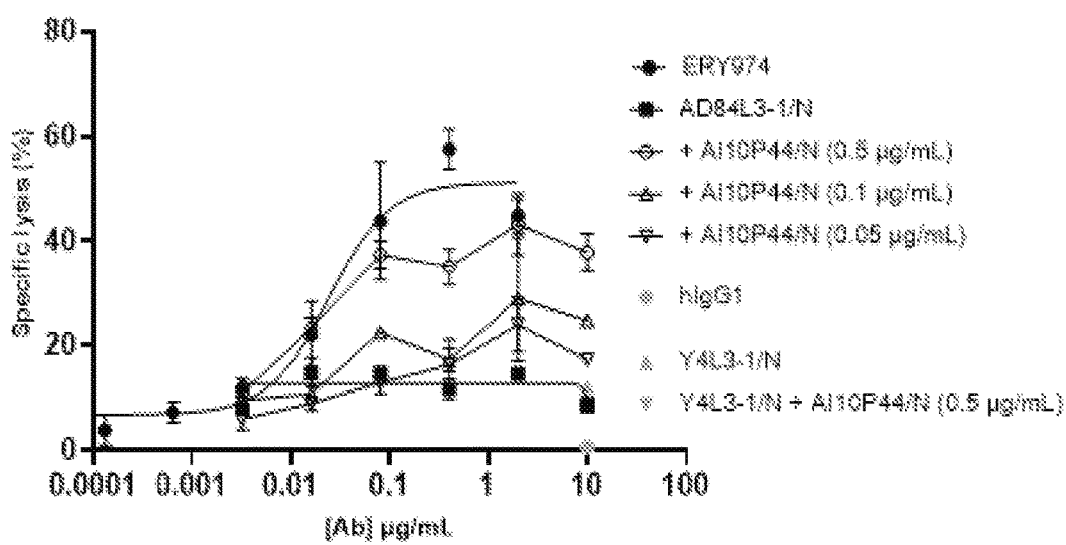

To further assess the killing synergy, we included a GPC3 cell line with lower expression of the target. The synergy between CD3-bispecific antibody and CD28-bispecific antibody is not cell line specific, as the Hep 3B cell line (expressing 60'000 GPC3/cell, ATCC Hep 3B2.1-7) was also killed more efficiently by the CD3 and CD28-bispecific antibody combination than by the GPC3×CD3 bispecific antibody alone. Increased killing is found for all CD28-bispecific antibody claimed in this application. Combination of AD84L3-1/N with AI3P30/N at 2.5 µg/mL demonstrates similar or slightly lower killing as ERY974 single treatment (FIG. 6A). As shown in FIGS. 6B, 6C and 6D effector cells from three independent PBMC donors all induced superior killing with AI3P44/N at 0.5 µg/mL compared to ERY974 single agent. As observed with HepG2 cells, also with Hep 3B cells synergistic killing activity can be fine-tuned by lowering the concentration of the GPC3×CD28 bispecific antibody (FIGS. 6B-6D, Table 5B). Combining CD3-bispecific antibody to a CD28-bispecific antibody, pairing the lower affinity CD28 arm (AI10) to a GPC3 arm (P44) is also enhancing killing of Hep 3B cells compared to CD3-bispecific antibody alone. Efficacy in this case is comparable to ERY974 single treatment (FIG. 6E).

Example 11: Cytokines Released in the Supernatant Upon Enhanced Killing of GPC3-Expressing Tumor Cells by CD28 Costimulation with GPC3×CD28

Bispecific Antibodies

ERY974 single agent treatment was demonstrated to induce severe Cytokine Release Syndrome CRS in a clinical trial. Such CRS could be driven by an overactivation of T cells. Indeed, T cell activation leads to the release of effector cytokines which may compromise the therapeutic window in patients.

The capacity of the CD28 bispecific antibodies of this invention to enhance the release of cytokines by T-cells upon killing of GPC3-expressing tumor cells in presence of GPC3×CD3 was assessed by quantifying selected cytokines in the supernatant at the end of a TDCC assay. Cytokine levels were compared to those induced by ERY974 single agent treatment.

Following the co-culture of GPC3 positive target cells and T cell-containing PBMCs as described in Example 10, the culture supernatants were harvested by centrifugation and stored frozen at −80° until further analysis. Cytokines (IL-2, IL-6, TNF-α and IFN-γ) were quantified using the Mesoscale Discovery Platform by using multiplex kits.

Results of an experiment where Hep G2 cells were co-cultured with PBMC at a ET ratio of 20:1 for 48 h with a dose range of the GPC3×CD3 and different fixed doses of a GPC3×CD28 bispecific antibody (AI3P44/N) are shown in FIGS. 7A-7D. Resulting TDCC is shown in FIG. 7A with IFN-g, IL-6 and TNF-α levels depicted in FIGS. 7B, FIG. 7C and FIG. 7D respectively. Single agent treatment with the GPC3×CD3 (AD84L3-1/N) resulted in very low level of cytokines released by T cells, while combination treatment with the tested GPC3×CD28 bispecific antibody substantially increased all measured cytokines, reflecting the better activation of T cells as suggested by the previously described increased TDCC activity. By lowering the concentration of the CD28-bispecific antibody, resulting cytokine levels can be decreased, below the ones obtained with ERY974 single treatment and, importantly, without compromising statistically significantly the maximal killing activity afforded by the combination (FIGS. 7A-7D). As illustrated in FIGS. 7A-7D, at 0.1 mg/mL, the maximum AI3P44/N killing/TDCCis above the maximum achieved with ERY974; However, the release of IFN-g, IL-6 and TNF-α is below the release observed with ERY974. Similar data were generated by using another CD28-bispecific antibody pairing the same CD28 arm (e.g. AI3) to another GPC3 arm (e.g. P30).

Killing activity and cytokine release can both be fine-tuned by lowering the concentration of the CD28 module (FIGS. 8A-8D). Decrease of maximal killing is less than the reduction of cytokine release if the concentration of AI3P30 is decreased from 500 ng/ml to 100 or 50 ng/ml (FIGS. 8A-8D). At 0.5 mg/mL of AI3P30/N, the maximal killing achieved is close to the maximal killing achieved with ERY974, but cytokine release is below, especially for IL-6 and TNF-α. In addition, data in FIGS. 9E-9H show much lower cytokine release by the combination of AD84L3-1/N with 100 ng/mL AI10P44 (lower affinity CD28 arm) compared to ERY974 single agent application, but maximal efficacy/killing of GPC3 expressing cancer cells is approx. 30% with ERY974 and still approx. 20% with the combination (FIGS. 9E-9F). The GPC3×CD3 and GPC3×CD28 bispecific antibodies of this invention enable the ability to modify the ratio of tumor cell killing to cytokine release. This allows the ability to reduce CRS, which is advantageous over current therapies such as "ERY974", which failed to achieve clinical efficacy at low doses and induced high CRS (Results of a phase 1 dose escalation study of ERY974, an anti-glypican 3 (GPC3)/CD3 bispecific antibody, in patients with advanced solid tumors. Safran et al. Cancer Res (2021) 81 (13_Supplement): CT111).

Figure 10E:
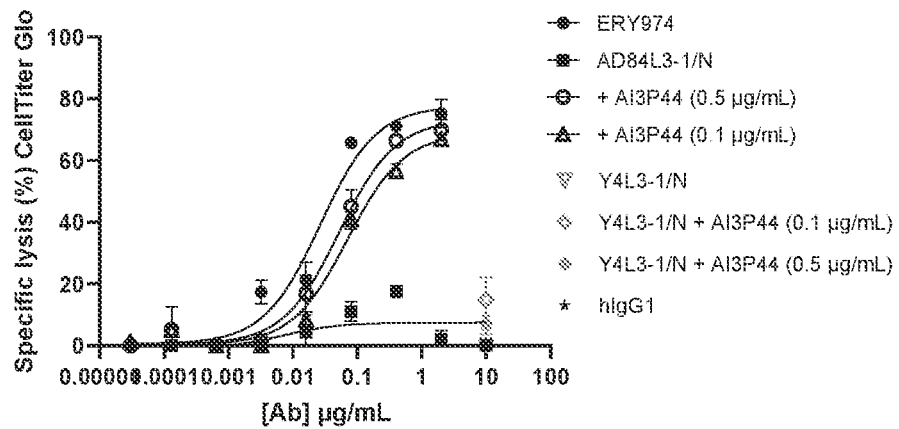
Figure 10F:
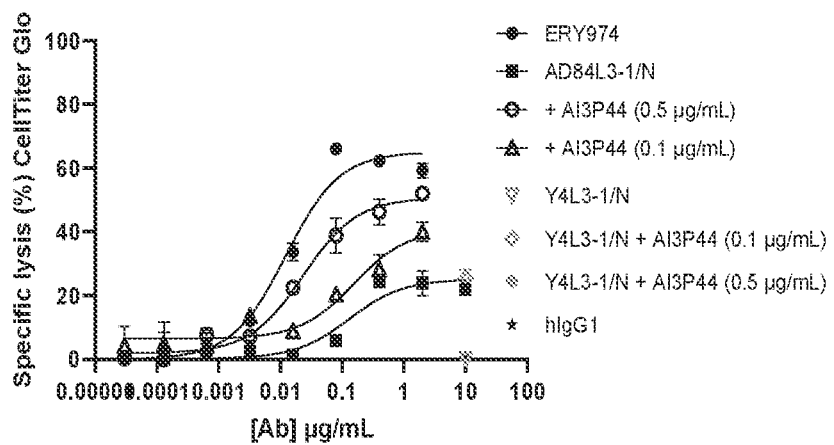

Finally, TDCC activity of the combination is shown using the CellTiter-Glo readout. Contrary to the LDH release assay which relies on dead cells for quantification of TDCC, CellTiter-Glo assay format quantifies the ATP level in the remaining live cells, which better reflects the TDCC induced by bispecific antibodies in presence of effector cells and is recognized to be more sensitive (Choosing the right cell-based assay for your research. Riss, T. et al. Promega Cell Note, Issue 6 (2003)). Concentration-dependent killing is shown of three different GPC3-expressing cancer cell lines with a large expression of GPC3, including Hep G2 (700'000 GPC3/cell), Hep 3B (60'000 GPC3/cell), and HuH-7 (18'000 GPC3/cell). As observed with Hep G2 cells, the combination of AD84L3-1/N and AI3P44/N (0.5 or 0.1 mg/mL) enhances killing of cancer cells up to 80% with an efficacy comparable to ERY974 single treatment (FIGS. 10A-10B). Strong, synergistic killing effect of the combination is also observed using Hep 3B cells (up to 80% of maximal killing). FIGS. 10A-10F show that the efficacy of the combination can even be driven to higher potency for tumor cell killing than achieved with ERY974 (FIGS. 10C-10D). Using HuH-7 cells, AI3P44/N (tested at 0.5 mg/mL) can boost AD84L3-1/N mediated killing/TDCC, to a level close to ERY974 single agent treatment with a maximal killing of 60-80% of malignant cells (FIGS. 10E-10F).

Overall, data in the present invention demonstrate that GPC3×CD28 κλ-bodies can boost GPC3×CD3 κλ-body (AD84L3-1/N) mediated killing/TDCC, to a level close to or higher than ERY974 single agent treatment, especially in tumor cells with low expression of GPC3. TDCC and related cytokine production can be attenuated by decreasing CD28-κλ bodies concentration, CD28 affinity or using another GPC3 arm (e.g. P30) or CD28 arm (e.g. A110), while maintaining efficacy. Additionally, at similar or equal efficacy/TDCC, cytokine release induced by the combination of bispecific antibodies of the present invention is significantly lower when compared to ERY974 (FIGS. 9A-9H).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

Additional embodiments of the disclosure include the following:

Embodiment 1. A bispecific antibody comprising:
  a. a first antigen binding domain that binds to CD3; wherein the first antigen binding domain comprises:
    i. a first heavy chain variable region having a complementarity determining region 1 (CDR1) comprising the amino acid sequence of (SEQ ID NO: 6); a complementarity determining region 2 (CDR2) comprising the amino acid sequence of (SEQ ID NO: 7); and a complementarity determining region 3 (CDR3) comprising the amino acid sequence of (SEQ ID NO:8); and ii. a first light chain variable region having:
1. a CDR1 comprising the amino acid sequence of SEQ ID NO: 11; a CDR2 comprising the amino acid sequence of SEQ ID NO: 12; and a CDR3 comprising the amino acid sequence of SEQ ID NO: 13; and
b. a second antigen binding domain that bind GPC3, wherein the second antigen binding domain comprises:
i. a second heavy chain variable region having a CDR1 comprising the amino acid sequence of SEQ ID NO: 6; a CDR2 comprising the amino acid sequence of SEQ ID NO: 7; and a CDR3 comprising the amino acid sequence of SEQ ID NO: 8; and
ii. second light chain variable region having:
1. a CDR1 comprising the amino acid sequence of SEQ ID NO: 16; a CDR2 comprising the amino acid sequence of SEQ ID NO: 17; and a CDR3 comprising the amino acid sequence of SEQ ID NO: 18; or
2. a CDR1 comprising the amino acid sequence of SEQ ID NO: 21; a CDR2 comprising the amino acid sequence of SEQ ID NO: 22; and a CDR3 comprising the amino acid sequence of SEQ ID NO: 23

Embodiment 2. A bispecific antibody comprising:
c. a first antigen binding domain that binds to CD28; wherein the first antigen binding domain comprises:
i. a first heavy chain variable region having a complementarity determining region 1 (CDR1) comprising the amino acid sequence of (SEQ ID NO: 1); a complementarity determining region 2 (CDR2) comprising the amino acid sequence of (SEQ ID NO: 2); and a complementarity determining region 3 (CDR3) comprising the amino acid sequence of (SEQ ID NO:3); and
ii. a first light chain variable region having:
1. a CDR1 comprising the amino acid sequence of SEQ ID NO: 41; a CDR2 comprising the amino acid sequence of SEQ ID NO: 42; and a CDR3 comprising the amino acid sequence of SEQ ID NO: 43; or
2. a CDR1 comprising the amino acid sequence of SEQ ID NO: 46; a CDR2 comprising the amino acid sequence of SEQ ID NO: 47; and a CDR3 comprising the amino acid sequence of SEQ ID NO: 48; or
3. a CDR1 comprising the amino acid sequence of SEQ ID NO: 51; a CDR2 comprising the amino acid sequence of SEQ ID NO: 52; and a CDR3 comprising the amino acid sequence of SEQ ID NO: 53
d. a second antigen binding domain that binds GPC3, wherein the second antigen binding domain comprises:
i. a second heavy chain variable region having a CDR1 comprising the amino acid sequence of SEQ ID NO: 1; a CDR2 comprising the amino acid sequence of SEQ ID NO: 2; and a CDR3 comprising the amino acid sequence of SEQ ID NO: 3; and
ii. second light chain variable region having:
1. a CDR1 comprising the amino acid sequence of SEQ ID NO: 26; a CDR2 comprising the amino acid sequence of SEQ ID NO: 27 and a CDR3 comprising the amino acid sequence of SEQ ID NO: 28; or
2. a CDR1 comprising the amino acid sequence of SEQ ID NO: 31; a CDR2 comprising the amino acid sequence of SEQ ID NO: 32 and a CDR3 comprising the amino acid sequence of SEQ ID NO: 33; or
3. a CDR1 comprising the amino acid sequence of SEQ ID NO: 36; a CDR2 comprising the amino acid sequence of SEQ ID NO: 37 and a CDR3 comprising the amino acid sequence of SEQ ID NO: 38.

Embodiment 3. The bispecific antibody of embodiment 2, wherein the first and second heavy chain variable region comprises the amino acid sequence of SEQ ID NO: 4.

Embodiment 4. The bispecific antibody of embodiment 1, wherein the first and second heavy chain comprises the amino acid sequence of SEQ ID NO: 9.

Embodiment 5. The bispecific antibody of embodiment 2, wherein the second light chain variable region of
a. part ii (1) comprises the amino acid sequence of SEQ ID NO: 29;
b. part ii (2) comprises the amino acid sequence of SEQ ID NO: 34; or
c. part ii (3) comprises the amino acid sequence of SEQ ID NO: 39.

Embodiment 6. The bispecific antibody of claim 1, wherein the second light chain variable region of
a. part ii (1) comprises the amino acid sequence of SEQ ID NO: 19; or
b. part ii (2) comprises the amino acid sequence of SEQ ID NO: 24.

Embodiment 7. The bispecific antibody of embodiment 1, wherein the first light chain variable region comprises the amino acid sequence of SEQ ID NO: 14.

Embodiment 8. The bispecific antibody of embodiment 1, wherein the first light chain comprises the amino acid sequence of SEQ ID NO: 15.

Embodiment 9. The bispecific antibody of embodiment 2, wherein the first light chain variable region of:
a. part a (ii) 1 comprises the amino acid sequence of SEQ ID NO: 44;
b. part a (ii) 2 comprises the amino acid sequence of SEQ ID NO: 49; or
c. part a (ii) 2 comprises the amino acid sequence of SEQ ID NO: 54.

Embodiment 10. The bispecific antibody of embodiment 2, wherein the first light chain of:
a. part a (ii) 1 comprises the amino acid sequence of SEQ ID NO: 45;
b. part a (ii) 2 comprises the amino acid sequence of SEQ ID NO: 50; or
c. part a (ii) 2 comprises the amino acid sequence of SEQ ID NO: 55.

Embodiment 11. The bispecific antibody of any one of the preceding embodiments wherein the first light chain is a kappa and the second light chain is a lambda.

Embodiment 12. The bispecific antibody of any one of the preceding embodiments wherein the first light chain is a lambda and the second light chain is a kappa.

Embodiment 13. The bispecific antibody of any one of the preceding embodiments, wherein the bispecific antibody comprises an Fc domain comprising one or more amino acid substitutions that reduce binding to an activating Fc receptor and/or reduce effector function.

Embodiment 14. The bispecific antibody of embodiment 13, wherein the amino acid substitution comprises a L234A and L235A substitution.

Embodiment 15. The bispecific antibody of embodiment 13 or 14, wherein the amino acid substitution comprises a L234A, a L235A and a P329A or P329G or P329R substitution.

Embodiment 16. The bispecific antibody of any one of the preceding embodiments, wherein the antibody has an IgG isotype.

Embodiment 17. The bispecific antibody of any one of the preceding embodiments, wherein the antibody is a human antibody.

Embodiment 18. The bispecific antibody of any one of the preceding embodiments, wherein the composition enables tumor-specific T cell activation.

Embodiment 19. A composition comprising the bispecific antibody of any one of the preceding embodiments.

Embodiment 20. A composition comprising the bispecific antibody of embodiment 1 and claim 2.

Embodiment 21. A method of reducing the proliferation of and/or killing a cancer cell comprising contacting the cell with the composition according to any of embodiments 19-20.

Embodiment 22. A method of treating a cancer in a subject comprising administering to the subject the composition according to any one of embodiments 19-20.

Embodiment 23. The method of embodiment 21 or 22, wherein the cancer is GPC3 positive.

We claim:

1. A bispecific antibody comprising:
   a. a first antigen binding domain that binds to CD3; wherein the first antigen binding domain comprises:
      i. a first heavy chain variable region having a complementarity determining region 1 (CDRH1) comprising the amino acid sequence of SEQ ID NO: 6; a complementarity determining region 2 (CDRH2) comprising the amino acid sequence of SEQ ID NO: 7; and a complementarity determining region 3 (CDRH3) comprising the amino acid sequence of SEQ ID NO: 8; and ii. a first light chain variable region having: a CDRL1 comprising the amino acid sequence of SEQ ID NO: 11; a CDRL2 comprising the amino acid sequence of SEQ ID NO: 12; and a CDRL3 comprising the amino acid sequence of SEQ ID NO: 13; and
b. a second antigen binding domain that binds to GPC3, wherein the second antigen binding domain comprises:
i. a second heavy chain variable region having a CDRH1 comprising the amino acid sequence of SEQ ID NO: 6; a CDRH2 comprising the amino acid sequence of SEQ ID NO: 7; and a CDRH3 comprising the amino acid sequence of SEQ ID NO: 8; and
ii. second light chain variable region having:
1. A CDRL1 comprising the amino acid sequence of SEQ ID NO: 16;
a CDRL2 comprising the amino acid sequence of SEQ ID NO: 17; and
a CDRL3 comprising the amino acid sequence of SEQ ID NO: 18; or
2. A CDRL1 comprising the amino acid sequence of SEQ ID NO: 21;
a CDRL2 comprising the amino acid sequence of SEQ ID NO: 22; and
a CDRL3 comprising the amino acid sequence of SEQ ID NO: 23.

2. The bispecific antibody of claim 1, wherein the first heavy chain variable region and the second heavy chain variable region comprises the amino acid sequence of SEQ ID NO: 9.

3. The bispecific antibody of claim 2, wherein the first heavy chain and the second heavy chain comprises the amino acid sequence of SEQ ID NO: 10.

4. The bispecific antibody of claim 3, wherein the first light chain variable region comprises the amino acid sequence of SEQ ID NO: 14.

5. The bispecific antibody of claim 4, wherein the first light chain comprises the amino acid sequence of SEQ ID NO: 15.

6. The bispecific antibody of claim 5, wherein the second light chain variable region of
a. part b. ii. 1. comprises the amino acid sequence of SEQ ID NO: 19; or
b. part b. ii. 2. comprises the amino acid sequence of SEQ ID NO: 24.

7. The bispecific antibody of claim 6, wherein the second light chain of
a. part b. ii. 1. comprises the amino acid sequence of SEQ ID NO: 20; or
b. part b. ii. 2. comprises the amino acid sequence of SEQ ID NO: 25.

8. A bispecific antibody comprising:
a. a first antigen binding domain that binds to CD28; wherein the first antigen binding domain comprises:
i. a first heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and
ii. a first light chain variable region having:
1. A CDRL1 comprising the amino acid sequence of SEQ ID NO: 41;
a CDRL2 comprising the amino acid sequence of SEQ ID NO: 42; and
a CDRL3 comprising the amino acid sequence of SEQ ID NO: 43; or
2. A CDRL1 comprising the amino acid sequence of SEQ ID NO: 46;
a CDRL2 comprising the amino acid sequence of SEQ ID NO: 47; and
a CDRL3 comprising the amino acid sequence of SEQ ID NO: 48; or
3. A CDRL1 comprising the amino acid sequence of SEQ ID NO: 51;
a CDRL2 comprising the amino acid sequence of SEQ ID NO: 52; and
a CDRL3 comprising the amino acid sequence of SEQ ID NO: 53; and
b. a second antigen binding domain that binds GPC3, wherein the second antigen binding domain comprises:
i. a second heavy chain variable region having a CDRH1 comprising the amino acid sequence of SEQ ID NO: 1; a CDRH2 comprising the amino acid sequence of SEQ ID NO: 2; and a CDRH3 comprising the amino acid sequence of SEQ ID NO: 3; and
ii. second light chain variable region having:
1. A CDRL1 comprising the amino acid sequence of SEQ ID NO: 26;
a CDRL2 comprising the amino acid sequence of SEQ ID NO: 27; and
a CDRL3 comprising the amino acid sequence of SEQ ID NO: 28; or
2. A CDRL1 comprising the amino acid sequence of SEQ ID NO: 31;
a CDRL2 comprising the amino acid sequence of SEQ ID NO: 32; and
a CDRL3 comprising the amino acid sequence of SEQ ID NO: 33; or
3. A CDRL1 comprising the amino acid sequence of SEQ ID NO: 36;
a CDRL2 comprising the amino acid sequence of SEQ ID NO: 37; and
a CDRL3 comprising the amino acid sequence of SEQ ID NO: 38.

9. The bispecific antibody of claim 8, wherein the first heavy chain variable region and the second heavy chain variable region comprises the amino acid sequence of SEQ ID NO: 4.

10. The bispecific antibody of claim 9, wherein the first heavy chain and the second heavy chain comprises the amino acid sequence of SEQ ID NO: 5.

11. The bispecific antibody of claim 10, wherein the first light chain variable region of:
a. part a. ii. 1. comprises the amino acid sequence of SEQ ID NO: 44;
b. part a. ii. 2. comprises the amino acid sequence of SEQ ID NO: 49; or
c. part a. ii. 3. comprises the amino acid sequence of SEQ ID NO: 54.

12. The bispecific antibody of claim 11, wherein the first light chain of:
a. part a. ii. 1. comprises the amino acid sequence of SEQ ID NO: 45;
b. part a. ii. 2. comprises the amino acid sequence of SEQ ID NO: 50; or
c. part a. ii. 3. comprises the amino acid sequence of SEQ ID NO: 55.

13. The bispecific antibody of claim 12, wherein the second light chain variable region of
a. part b. ii. 1. comprises the amino acid sequence of SEQ ID NO: 29;
b. part b. ii. 2. comprises the amino acid sequence of SEQ ID NO: 34; or
c. part b. ii. 3. comprises the amino acid sequence of SEQ ID NO: 39.

14. The bispecific antibody of claim 13, wherein the second light chain of:
- a. part b. ii. 1. comprises the amino acid sequence of SEQ ID NO: 30;
- b. part b. ii. 2. comprises the amino acid sequence of SEQ ID NO: 35; or
- c. part b. ii. 3. comprises the amino acid sequence of SEQ ID NO: 40.

15. The bispecific antibody of claim 7 or 14, wherein the first light chain is a kappa and the second light chain is a lambda.

16. The bispecific antibody of claim 7 or 14, wherein the first light chain is a lambda and the second light chain is a kappa.

17. The bispecific antibody of claim 15, wherein the bispecific antibody comprises an Fc domain comprising one or more amino acid substitutions that reduce binding to an activating Fc receptor and/or reduce effector function.

18. The bispecific antibody of claim 17, wherein the amino acid substitution comprises a L234A and L235A substitution.

19. The bispecific antibody of claim 18, wherein the amino acid substitution comprises i) a L234A substitution;
- ii) a L235A substitution; and
- iii) a P329A, P329G or P329R substitution.

20. The bispecific antibody of claim 19, wherein the antibody has an IgG isotype.

21. The bispecific antibody of claim 20, wherein the antibody is a human antibody.

22. A composition comprising the bispecific antibody of claim 21.

23. A composition comprising a first bispecific antibody and a second bispecific antibody, wherein:
- a. the first bispecific antibody comprises a first antigen binding domain that binds to CD3 and a second antigen binding domain that binds to GPC3, wherein:
  - i. the first antigen binding domain comprises:
    1. a first heavy chain variable region having a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; and
    2. a first light chain variable region having a CDRL1 comprising the amino acid sequence of SEQ ID NO: 11, a CDRL2 comprising the amino acid sequence of SEQ ID NO: 12, and a CDRL3 comprising the amino acid sequence of SEQ ID NO: 13; and
  - ii. the second antigen binding domain comprises:
    1. a second heavy chain variable region having a CDRH1 comprising the amino acid sequence of SEQ ID NO: 6, a CDRH2 comprising the amino acid sequence of SEQ ID NO: 7, and a CDRH3 comprising the amino acid sequence of SEQ ID NO: 8; and
    2. a second light chain variable region having a CDRL1 comprising the amino acid sequence of SEQ ID NO: 16, a CDRL2 comprising the amino acid sequence of SEQ ID NO: 17, and a CDRL3 comprising the amino acid sequence of SEQ ID NO: 18; or a CDRL1 comprising the amino acid sequence of SEQ ID NO: 21, a CDRL2 comprising the amino acid sequence of SEQ ID NO: 22, and a CDRL3 comprising the amino acid sequence of SEQ ID NO: 23; and
- b. the second bispecific antibody comprises a first antigen binding domain that binds to CD28 and a second antigen binding domain that binds to GPC3, wherein:
  - i. the first antigen binding domain comprises:
    1. a first heavy chain variable region having a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; and
    2. a first light chain variable region having a CDRL1 comprising the amino acid sequence of SEQ ID NO: 41, a CDRL2 comprising the amino acid sequence of SEQ ID NO: 42, and a CDRL3 comprising the amino acid sequence of SEQ ID NO: 43; or a CDRL1 comprising the amino acid sequence of SEQ ID NO: 46, a CDRL2 comprising the amino acid sequence of SEQ ID NO: 47, and a CDRL3 comprising the amino acid sequence of SEQ ID NO: 48; or a CDRL1 comprising the amino acid sequence of SEQ ID NO: 51, a CDRL2 comprising the amino acid sequence of SEQ ID NO: 52, and a CDRL3 comprising the amino acid sequence of SEQ ID NO: 53; and
  - ii. the second antigen binding domain comprises:
    1. a second heavy chain variable region having a CDRH1 comprising the amino acid sequence of SEQ ID NO: 1, a CDRH2 comprising the amino acid sequence of SEQ ID NO: 2, and a CDRH3 comprising the amino acid sequence of SEQ ID NO: 3; and
    2. a second light chain variable region having a CDRL1 comprising the amino acid sequence of SEQ ID NO: 26, a CDRL2 comprising the amino acid sequence of SEQ ID NO: 27, and a CDRL3 comprising the amino acid sequence of SEQ ID NO: 28; or a CDRL1 comprising the amino acid sequence of SEQ ID NO: 31, a CDRL2 comprising the amino acid sequence of SEQ ID NO: 32, and a CDRL3 comprising the amino acid sequence of SEQ ID NO: 33; or a CDRL1 comprising the amino acid sequence of SEQ ID NO: 36, a CDRL2 comprising the amino acid sequence of SEQ ID NO: 37, and a CDRL3 comprising the amino acid sequence of SEQ ID NO: 38.

24. The composition of claim 23, wherein the composition enables tumor-specific T cell activation.

25. A method of reducing the proliferation of a cancer cell and/or killing a cancer cell comprising contacting the cell with the composition according to claim 23.

26. A method of treating a cancer in a subject comprising administering to the subject the composition according to claim 23.

27. The method of claim 25, wherein the cancer cell is GPC3 positive.

28. The bispecific antibody of claim 16, wherein the bispecific antibody comprises an Fc domain comprising one or more amino acid substitutions that reduce binding to an activating Fc receptor and/or reduce effector function.

29. The bispecific antibody of claim 28, wherein the amino acid substitution comprises a L234A and L235A substitution.

30. The bispecific antibody of claim 29, wherein the amino acid substitution comprises i) a L234A substitution;
- ii) a L235A substitution; and
- iii) a P329A, P329G or P329R substitution.

31. The bispecific antibody of claim 30, wherein the antibody has an IgG isotype.

32. The bispecific antibody of claim 31, wherein the antibody is a human antibody.

33. A composition comprising the bispecific antibody of claim 32.

34. The method of claim 26, wherein the cancer is GPC3 positive.

* * * * *